United States Patent
Gunic et al.

(10) Patent No.: US 9,296,709 B2
(45) Date of Patent: Mar. 29, 2016

(54) MANUFACTURE OF 2-(5-BROMO-4-(4-CYCLOPROPYLNAPHTHALEN-1-YL)-4H-1,2,4-TRIAZOL-3-YLTHIO)ACETIC ACID

(71) Applicant: ARDEA BIOSCIENCES, INC., San Diego, CA (US)

(72) Inventors: Esmir Gunic, San Diego, CA (US); Gabriel Galvin, San Diego, CA (US)

(73) Assignee: ARDEA BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 14/409,806

(22) PCT Filed: Jul. 2, 2013

(86) PCT No.: PCT/US2013/049135
§ 371 (c)(1),
(2) Date: Dec. 19, 2014

(87) PCT Pub. No.: WO2014/008295
PCT Pub. Date: Jan. 9, 2014

(65) Prior Publication Data
US 2015/0252010 A1    Sep. 10, 2015

Related U.S. Application Data

(60) Provisional application No. 61/667,922, filed on Jul. 3, 2012.

(51) Int. Cl.
*C07D 249/12* (2006.01)

(52) U.S. Cl.
CPC ..................................... *C07D 249/12* (2013.01)

(58) Field of Classification Search
CPC .................................................... C07D 249/12
See application file for complete search history.

(56) References Cited

U.S. PATENT DOCUMENTS

| | | | |
|---|---|---|---|
| 7,435,752 B2 | 10/2008 | Girardet et al. |
| 7,683,087 B2 | 3/2010 | Girardet et al. |
| 7,947,721 B2 | 5/2011 | Girardet et al. |
| 8,003,681 B2 | 8/2011 | Girardet et al. |
| 8,084,483 B2 | 12/2011 | Quart et al. |
| 8,106,205 B2 | 1/2012 | Girardet et al. |
| 8,173,690 B2 | 5/2012 | Gunic et al. |
| 8,193,234 B2 | 6/2012 | Gunic et al. |
| 8,242,154 B2 | 8/2012 | Gunic et al. |
| 8,252,828 B2 | 8/2012 | Girardet et al. |
| 8,283,369 B2 | 10/2012 | Quart |
| 8,344,012 B2 | 1/2013 | Gunic et al. |
| 8,357,713 B2 | 1/2013 | Quart |
| 8,481,581 B2 | 7/2013 | Girardet et al. |
| 8,524,754 B2 | 9/2013 | Zamansky et al. |
| 8,546,436 B2 | 10/2013 | Galvin et al. |
| 8,546,437 B2 | 10/2013 | Quart |
| 8,552,043 B2 | 10/2013 | Girardet et al. |
| 8,633,232 B2 | 1/2014 | Gunic et al. |
| 2006/0135556 A1 | 6/2006 | Girardet et al. |
| 2006/0270725 A1 | 11/2006 | Girardet et al. |
| 2008/0176850 A1 | 7/2008 | Girardet et al. |
| 2008/0249131 A1 | 10/2008 | Girardet et al. |
| 2008/0319201 A1 | 12/2008 | Girardet et al. |
| 2009/0197825 A1 | 8/2009 | Quart et al. |
| 2010/0056464 A1 | 3/2010 | Gunic et al. |
| 2010/0056465 A1 | 3/2010 | Gunic et al. |
| 2010/0056542 A1 | 3/2010 | Gunic et al. |
| 2010/0056593 A1 | 3/2010 | Gunic et al. |
| 2010/0069645 A1 | 3/2010 | Girardet et al. |
| 2010/0081827 A1 | 4/2010 | Girardet et al. |
| 2010/0137590 A1 | 6/2010 | Girardet et al. |
| 2011/0190491 A1 | 8/2011 | Girardet et al. |
| 2011/0268801 A1 | 11/2011 | Quart |
| 2011/0293719 A1 | 12/2011 | Quart |
| 2011/0313157 A1 | 12/2011 | Girardet et al. |
| 2012/0077981 A1 | 3/2012 | Girardet et al. |
| 2012/0129903 A1 | 5/2012 | Zamansky et al. |

(Continued)

FOREIGN PATENT DOCUMENTS

| | | |
|---|---|---|
| WO | WO2004/030611 | 4/2004 |
| WO | WO2006/026356 | 3/2006 |
| WO | WO2009/070740 | 6/2009 |
| WO | WO2010/028189 | 3/2010 |
| WO | WO2010/028190 | 3/2010 |
| WO | WO2011/085009 | 7/2011 |
| WO | WO2011/126852 | 10/2011 |

(Continued)

OTHER PUBLICATIONS

U.S. Appl. No. 14/559,803, filed Dec. 3, 2014, Girardet et al.

(Continued)

*Primary Examiner* — Michael Barker
*Assistant Examiner* — Karen Cheng
(74) *Attorney, Agent, or Firm* — Wilson Sonsini Goodrich & Rosati

(57) ABSTRACT

Described herein are certain processes for the synthesis of compounds of Formula (I):

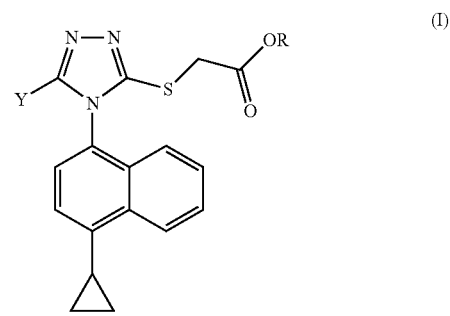

9 Claims, 20 Drawing Sheets

(56) References Cited

U.S. PATENT DOCUMENTS

| | | | |
|---|---|---|---|
| 2012/0164222 A1 | 6/2012 | Quart |
| 2012/0172405 A1 | 7/2012 | Galvin et al. |
| 2012/0283301 A1 | 11/2012 | Girardet et al. |
| 2013/0040907 A1 | 2/2013 | Gunic et al. |
| 2013/0040963 A1 | 2/2013 | Gunic et al. |
| 2013/0059868 A1 | 3/2013 | Miner et al. |
| 2013/0178484 A1 | 7/2013 | Miner et al. |
| 2013/0296345 A1 | 11/2013 | Quart |
| 2013/0331403 A1 | 12/2013 | Galvin et al. |
| 2013/0345271 A1 | 12/2013 | Zamansky et al. |
| 2014/0005136 A1 | 1/2014 | Quart |
| 2014/0128338 A1 | 5/2014 | Gunic et al. |

FOREIGN PATENT DOCUMENTS

| | | |
|---|---|---|
| WO | WO2011/159732 | 12/2011 |
| WO | WO2012/050589 | 4/2012 |
| WO | WO2012/092395 | 7/2012 |
| WO | WO2014/008295 | 1/2014 |

OTHER PUBLICATIONS

U.S. Appl. No. 14/577,129, filed Dec. 19, 2014, Galvin et al.
Bundgaard. Design and Application of Prodrugs. A Textbook of Drug Design and Development, Krosgaard-Larsen and Bundgaard, Ed., 1991, Chapter 5, pp. 113-191.
Fleishmann et al. "Lesinurad (RDEA594), a Novel Uricosuric Agent, in Combination with Febuxostat Shows Significant Additive Urate Lowering Effects . . . " (May 25-28, 2011).
Furniss et al. Vogel's Encyclopedia of Practical Organic Chemistry, $5^{th}$ Supp., Longman Scientific and Technical Ltd., Essex, 1991, pp. 809-816.
Heller. Electrical Wiring of Redox Enzymes. Acc. Chem. Res. 23:128-134 (1990).
Kerr et al. "Pharmacokinetics and Serum Urate Lowering Effect of RDEA594, a Novel URAT1 Inhibitor, in Gout Patients and Subjects with Varying . . . " (Mar. 2-5, 2011).
Kerr et al. "Pharmacokinetics, Efficacy and Safety of Lesinurad, a Novel URAT1 Inhibitor, in Individuals with Mild to Moderate Renal Impairment " (Nov. 5-9, 2011).
Lasko et al. "RDEA594, a Novel Uricosuric Agent, Significantly Reduced Serum Urate Levels and Was Well Tolerated in a Phase 2a Pilot Study in . . . " (Oct. 16-21, 2009).
PCT/US2013/049135 International Search Report and Written Opinion dated Nov. 1, 2013.
Perez-Ruiz et al. "Efficacy and Safety of a Range of Doses RDEA594, a Novel Uricosuric Agent, as Monotherapy in Gout Patients: Randomized, . . . " (Jun. 16-19, 2010).
Perez-Ruiz et al. "Efficacy and Safety of Lesinurad (RDEA594), a Novel Uricosuric Agent, Given in Combination with Allopurinol in Allopurinol-Refractory Gout Patients: Preliminary Results, . . . " (May 25-28, 2011).
Perez-Ruiz, F., et al. "Efficacy and Safety of Lesinurad (RDEA594), a Novel Uricosuric Agent, in Combination with Allopurinol in Gout Patients with Inadequate Response to Allopurinol: Results, . . . " (Jun. 6-9, 2012).
Saulnier et al. An Efficient Method for the Synthesis of Guanidino Prodrugs. Bioorganic and Medicinal Chemistry Letters 4(16):1985-18900 (1994).
Shen et al. "A RDEA594, a Novel Uricosuric Agent, Shows Significant Additive Activity in Combination with Allopurinol in Gout Patients" (Mar. 2-5, 2011).
Sundy et al. "Efficacy and Safety of Lesinurad (RDEA594), a Novel Uricosuric Agent, Given in Combination with Allopurinol in Allopurinol-Refractory Gout Patients: Preliminary Results, . . . " (Nov. 9-11, 2011).
Tan et al. "Lesinurad (RDEA594), a Investigational Uricosuric Agent for Hyperuricemia and Gout, Blocks OAT4 Transport, Mechanism of . . . " (May 25-28, 2011).
Yang et al. "Evaluation of Drug-Drug Interaction Potential Between RDEA594, Allopurinol and Febuxostat in Preclinical Species" (Oct. 16-21, 2009).
Yeh et al. "A Novel URAT1 Inhibitor, Shows Significant Additive Urate Lowering Effects in Combination with Febuxostat in Both Healthy Subjects and . . . " (Mar. 2-5, 2011).
Yeh et al. "Mode of Action of RDEA594 as a Uric Acid Lowering Agent in Humans Following Multiple Doses of its Prodrug, RDEA806" (Jun. 11-14, 2008).
Yeh et al. "RDEA594, a Novel Uricosuric Agent, Shows Impressive Reductions in Serum Urate Levels as a Monotherapy and Substantial Additive Activity . . . " (Jun. 16-19, 2010).
Yeh et al. "RDEA594, a Potential Uric Acid Lowering Agent through Inhibition of Uric Acid Reuptake, Shows Better Pharmacokinetics than its . . . " (Oct. 24-29, 2008).
Yeh et al. "RDEA594:A Potent URAT1 Inhibitor Without Affecting Other Important Renal Transporters, OAT1 and OAT3" (Jun. 10-13, 2009).
Yeh et al. "Safety, Pharmacokinetics, and Serum Uric Acid Lowering Effect of RDEA594, a Novel, Uricosuric Agent, in Healthy Volunteers" (Jun. 10-13, 2009).
Yeh et al. "Lesinurad (RDEA594), a Novel URAT1 Inhibitor, Shows Additive Serum Urate Lowering Effects in Combination with Xanthine Oxidase Inhibitor Febuxostat." (Apr. 22-25, 2011).
Yamada et a. Bleaching Activity of 4-Pheny 1-3-(substituted benzylthio)-4H-1,2,4-triazoles. Biosci Biotechnol Biochem 66(8):1671-1676 (2002).
Zibinsky et al. Reactivity of N-(1,2,4-triazolyl)-substituted 1,2,3-triazoles. Organic Letters 13:4870-4872 (2011).

Sodium 2-(5-bromo-4-(4-cyclopropylnaphthalen-1-yl)-4H-1,2,4-triazol-3-ylthio)acetate, Polymorph Form A: X-ray Powder Diffraction Pattern Sodium 2-(5-bromo-4-(4-cyclopropylnaphthalen-1-yl)-4H-1,2,4-triazol-3-ylthio)acetate, Polymorph Form B: X-ray Powder Diffraction Pattern Sodium 2-(5-bromo-4-(4-cyclopropylnaphthalen-1-yl)-4H-1,2,4-triazol-3-ylthio)acetate, Polymorph Form B': X-ray Powder Diffraction Pattern

MANUFACTURE OF 2-(5-BROMO-4-(4-CYCLOPROPYLNAPHTHALEN-1-YL)-4H-1,2,4-TRIAZOL-3-YLTHIO)ACETIC ACID

BACKGROUND OF THE INVENTION

Uric acid is the result of the oxidation of xanthine. Disorders of uric acid metabolism include, but are not limited to, polycythemia, myeloid metaplasia, gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis.

SUMMARY OF THE INVENTION

Efficient synthetic procedures are often required for large scale pilot plant syntheses of chemical compounds. Provided herein are certain scalable processes and methods for the synthesis of compounds of Formula (I):

Formula (I)

wherein

R is H, —$C_1$-$C_{20}$ alkyl, —$C_1$-$C_{20}$ alkenyl, —$C_3$-$C_{10}$ cycloalkyl, —$C_3$-$C_{10}$ cycloalkenyl, or R is a counter ion; and Y is H, OH, $NH_2$, F, Cl, Br, or I.

The compounds of Formula (I) described herein are useful for the treatment of disorders of uric acid metabolism.

In one aspect, provided herein is a process (Process 1) for preparing:

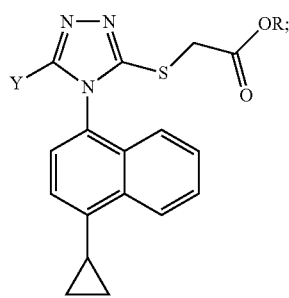

(Compound 1)

or (Compound 4)

comprising contacting a compound of Formula (II), or a salt thereof,

Formula (II)

wherein R is H, —$C_1$-$C_{20}$ alkyl, —$C_1$-$C_{20}$ alkenyl, —$C_3$-$C_{10}$ cycloalkyl, or —$C_3$-$C_{10}$ cycloalkenyl, with N-bromosuccinimide (NBS) and a solvent to provide a compound of structure:

Formula (III)

In some embodiments of the process described above, R is —$C_1$-$C_{20}$ alkyl, —$C_1$-$C_{20}$ alkenyl, —$C_3$-$C_{10}$ cycloalkyl, or —$C_3$-$C_{10}$ cycloalkenyl. In some embodiments of the process described above, R is methyl, ethyl, propyl, isopropyl, butyl, isobutyl, tert-butyl, isoamyl, pentyl, hexyl, heptyl, octyl, nonyl, terpenyl, bornyl, allyl, linalyl or geranyl.

In certain embodiments of the process described above, R is methyl or ethyl. In some specific embodiments of the process described above, R is methyl.

In some embodiments of the process described above, the reaction mixture is stirred for at least 12 hours at a temperature of between about room temperature and about 32° C.

In some embodiments of the process described above, the reaction mixture assay shows ≤1.5% area by HPLC of the compound of Formula (II).

In some embodiments of the process described above, the reaction mixture assay shows ≤0.2% area by HPLC of the compound of Formula (II).

In one embodiment of the process described above, the process further comprises
(i) contacting the compound of Formula (III) with a sodium hydroxide solution to provide Compound 4; and
(ii) optionally contacting Compound 4 with an acid to provide Compound 1.

In further embodiments of the process described above, step (i) further comprises optionally crystallizing Compound 4 from an aqueous sodium hydroxide solution.

In some embodiments of the process described above, the process further comprises
(a) dissolving Compound 4 in water and adding ethyl acetate to the mixture;
(b) contacting the biphasic mixture of step (a) with an acid and separating the organic phase to provide Compound 1.

In certain embodiments, the acid of step (b) is hydrochloric acid, hydrobromic acid, acetic acid, sulfuric acid, or phosphoric acid. In some specific embodiments, the acid of step (b) is hydrobromic acid.

In some embodiments of the process described above, the process further comprises recrystallization of Compound 1 from ethyl acetate. In such an embodiment, the process further comprises optionally adding n-heptane to the mixture.

Provided herein is Compound 3, obtainable by the process described above, and having the structure:

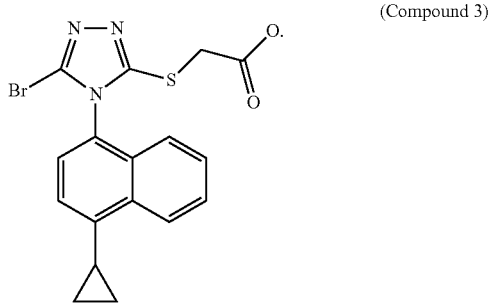

(Compound 3)

Provided herein is Compound 3-A, obtainable by the process described above, and having the structure:

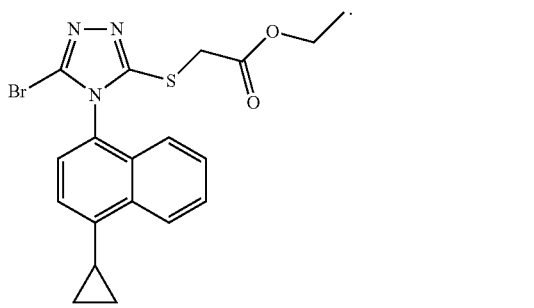

(Compound 3-A)

Provided herein is Compound 4, obtainable by the processes described above. In some embodiments, Compound 4 is a crystalline polymorph characterized by peaks at 4.90, 9.83, and 25.29°2θ±0.1°2θ. In some embodiments, Compound 4 is crystalline polymorph form A.

Provided herein is Compound 1, obtainable by the process described above.

In one aspect, provided herein is Compound 1 having no more than 0.1% of Compound 2 by area on an HPLC assay

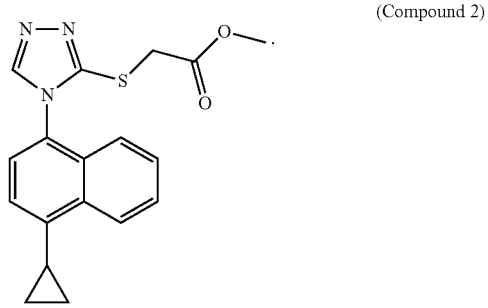 [SMILES: COC(=O)CSc1nncn1-c1ccc(C2CC2)c2ccccc12]

(Compound 2)

In one embodiment, Compound 1 having no more than 0.1% of Compound 2 is obtained by the processes described above.

In another aspect, provided herein is Compound 1, having no more than 0.1% of Compound 3 by area on an HPLC assay.

In one embodiment, Compound 1 having no more than 0.1% of Compound 3 is obtained by the processes described above.

In a further aspect, provided herein is Compound 1, having no more than 0.1% of Compound 2, and no more than 0.1% of Compound 3 by area on an HPLC assay.

In some embodiments, Compound 1 is a crystalline polymorph characterized by peaks at 10.32, 18.84, and 20.75°2θ±0.1°2θ. In certain embodiments, Compound 1 is crystalline polymorph form 1. In other embodiments, Compound 1 is a crystalline polymorph characterized by peaks at 10.46, 18.76, and 19.83°2θ±0.1°2θ. In certain embodiments, Compound 1 is crystalline polymorph form 2.

Provided herein in some embodiments is a reaction mixture comprising a compound of Formula (II), or a salt thereof

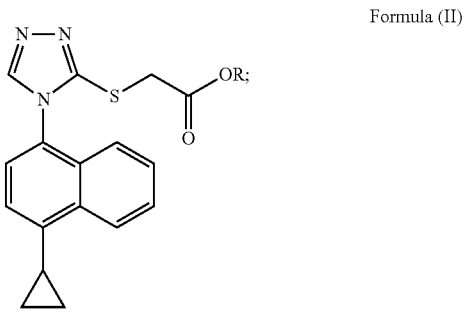

Formula (II)

wherein R is H, —$C_1$-$C_{20}$ alkyl, —$C_1$-$C_{20}$ alkenyl, —$C_3$-$C_{10}$ cycloalkyl, or —$C_3$-$C_{10}$ cycloalkenyl;
a brominating agent; and a solvent.

In some embodiments of the reaction mixture described above, R is —$C_1$-$C_{20}$ alkyl, —$C_1$-$C_{20}$ alkenyl, —$C_3$-$C_{10}$ cycloalkyl, or —$C_3$-$C_{10}$ cycloalkenyl. In certain embodiments, the brominating agent is N-bromosuccinimide (NBS). In some embodiments, the solvent is THF, DMF, acetonitrile, or MTBE. In certain embodiments, the solvent is THF. In further or additional embodiments of the reaction mixture described above, a compound of formula (III) is produced.

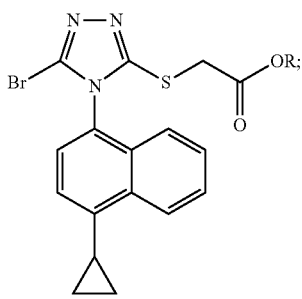

Formula (III)

wherein R is H, —$C_1$-$C_{20}$ alkyl, —$C_1$-$C_{20}$ alkenyl, —$C_3$-$C_{10}$ cycloalkyl, or —$C_3$-$C_{10}$ cycloalkenyl;

a solvent; and a base.

In some embodiments, a compound of formula (III) is produced, wherein R is —$C_1$-$C_{20}$ alkyl, —$C_1$-$C_{20}$ alkenyl, —$C_3$-$C_{10}$ cycloalkyl, or —$C_3$-$C_{10}$ cycloalkenyl.

Some embodiments provided herein describe a reaction mixture comprising a compound of formula (III)

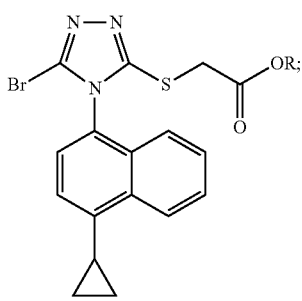

Formula (III)

wherein R is H, —$C_1$-$C_{20}$ alkyl, —$C_1$-$C_{20}$ alkenyl, —$C_3$-$C_{10}$ cycloalkyl, or —$C_3$-$C_{10}$ cycloalkenyl;

In some embodiments of the reaction mixture described above, R is —$C_1$-$C_{20}$ alkyl, —$C_1$-$C_{20}$ alkenyl, —$C_3$-$C_{10}$ cycloalkyl, or —$C_3$-$C_{10}$ cycloalkenyl. In some embodiments, the solvent is water. In further or additional embodiments, the acid is hydrobromic acid. In further or additional embodiments of the reaction mixture described above, Compound 4 is produced.

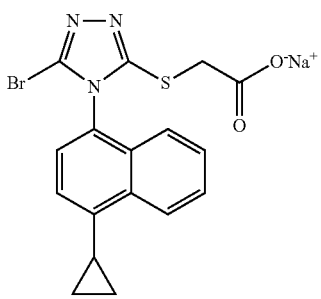

(Compound 4)

Other embodiments provided herein describe a reaction mixture comprising Compound 4 a solvent; and an acid.

In some embodiments of the reaction mixture described above, the acid is hydrobromic acid. In some embodiments, the solvent is water. In further or additional embodiments of the reaction mixture described above, Compound 1 is produced.

(Compound 1)

Br—[triazole-naphthyl-cyclopropyl]—S—CH$_2$—C(=O)—OH

In one aspect, a compound of Formula (II), used in Process 1 above, is prepared by a process (Process 2) comprising contacting a compound of structure:

(Compound 5)

[triazole-SH, naphthyl-cyclopropyl]

with a base, a solvent and a compound of Formula (IV):

Formula (IV)

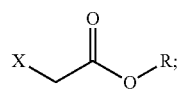

wherein X is halo, tosylate, mesylate, triflate, or besylate, and R is —$C_1$-$C_{20}$ alkyl, —$C_1$-$C_{20}$ alkenyl, —$C_3$-$C_{10}$ cycloalkyl, or —$C_3$-$C_{10}$ cycloalkenyl;

to provide a compound of Formula (II):

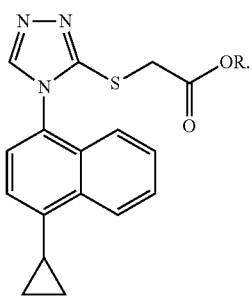

Formula (II)

In some embodiments of the process described above, the compound of Formula (IV) is selected from methyl bromoacetate, ethyl bromoacetate, methyl chloroacetate, and ethyl chloroacetate.

In some embodiments of the process described above, the process further comprises stirring the reaction mixture at a temperature between about 25° C. and about 40° C. for at least one hour.

In some embodiments of the process described above, the crude reaction product comprising a compound of Formula (II) is washed with a cooled mixture of Ethyl Acetate (EtOAc) and isopropanol.

Provided herein is a compound of structure:

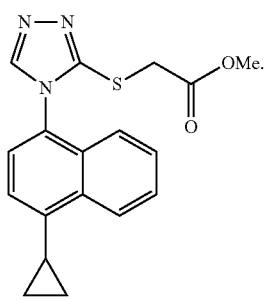

(Compound 2)

Provided herein is Compound 2, having an HPLC purity of at least 98%. Provided herein is Compound 2, having an HPLC purity of at least 99%.

In one embodiment, Compound 2, Compound 2 having an HPLC purity of at least 98%, or Compound 2 having an HPLC purity of at least 99%, is obtained by the processes described above.

Provided herein is a compound of structure:

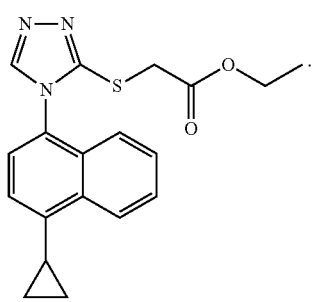

(Compound 2-A)

In one embodiment, Compound 2-A is obtained by the process described above.

Provided herein in some embodiments is a reaction mixture comprising a compound of formula (IV):

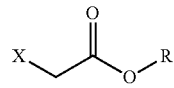

wherein X is a leaving group; R is H, —$C_1$-$C_{20}$ alkyl, —$C_1$-$C_{20}$ alkenyl, —$C_3$-$C_{10}$ cycloalkyl, or —$C_3$-$C_{10}$ cycloalkenyl; Compound 5; a base; and a solvent. In some embodiments of the reaction mixture described above, the compound of formula (IV) is methyl bromoacetate, ethyl bromoacetate, methylchloroacetate, or ethyl chloroacetate. In certain embodiments, a compound of formula (II)

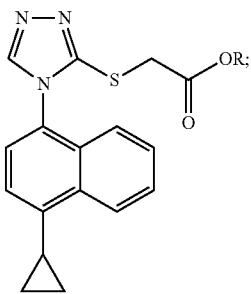

Formula (II)

wherein R is H, —$C_1$-$C_{20}$ alkyl, —$C_1$-$C_{20}$ alkenyl, —$C_3$-$C_{10}$ cycloalkyl, or —$C_3$-$C_{10}$ cycloalkenyl is produced in the reaction mixture described above. In certain embodiments, a Compound 2 or 2-A is produced in the reaction mixture described above.

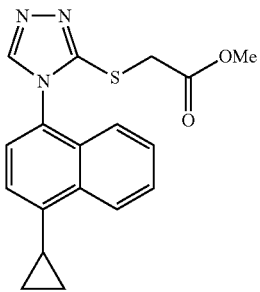

(Compound 2)

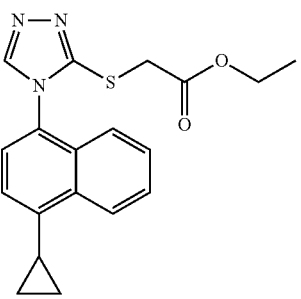

(Compound 2-A)

In one aspect, Compound 5, used in Process 2 described above is prepared by a process (Process 3) comprising (5-i) contacting a compound of structure:

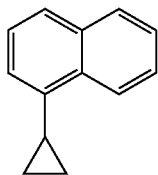
(Compound 6)

with nitric acid, water and a solvent to provide a compound of structure:

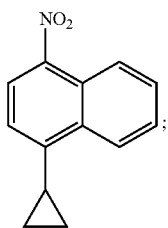
(Compound 7)

(5-ii) contacting Compound 7 with hydrogen, palladium on charcoal, and one or more solvents to provide a compound of structure:

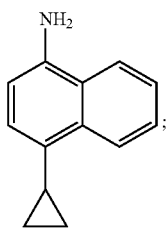
(Compound 8)

(5-iii) contacting Compound 8 with an acid to provide a salt of Compound 8;

(5-iv) contacting the salt of Compound 8 of step (5-iii) with a base, thiophosgene and a solvent and stirring the mixture at about 5° C. to provide a compound of structure:

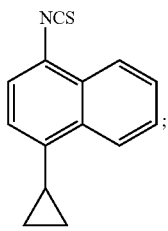
(Compound 9)

(5-v) contacting Compound 9 with formyl hydrazine and a solvent to provide a compound of structure:

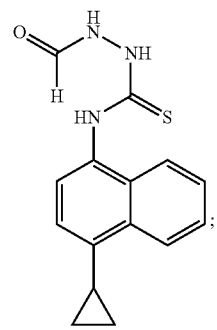
(Compound 10)

and (5-vi) contacting Compound 10 with a base, water and a solvent to provide Compound 5:

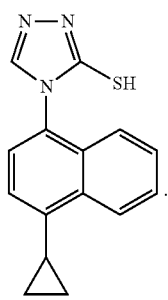
(Compound 5)

In some embodiments of the process described above, the acid in step (5-iii) is selected from hydrochloric acid, oxalic acid and tartaric acid. In a specific embodiment of the process described above, the acid in step (5-iii) is oxalic acid.

In one embodiment of the process described above, the salt of compound 8 in step (5-iv) is an oxalate salt.

Provided herein is Compound 8 oxalate salt, and having the structure:

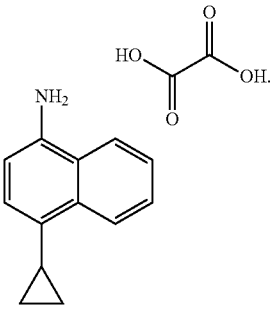
(Compound 8-A)

In one case, Compound 8-A is obtained by the processes described above.

Provided herein in some embodiments is a reaction mixture comprising Compound 9, a nucleophile and a solvent.

(Compound 9)

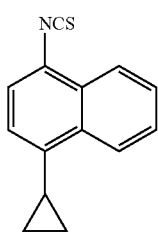

In some embodiments of the reaction mixture described above, the nucleophile is formyl hydrazine. In certain embodiments, Compound 10 is produced in the reaction mixture described above.

(Compound 10)

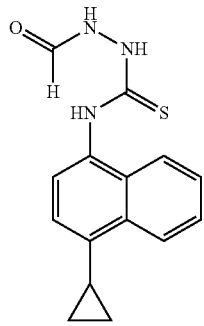

Also provided herein is a reaction mixture comprising Compound 10, a base and a solvent. In some embodiments, the base is potassium bicarbonate, potassium carbonate, sodium bicarbonate, sodium carbonate, or cesium carbonate. In certain embodiments, Compound 5 is produced in the reaction mixture described herein.

(Compound 5)

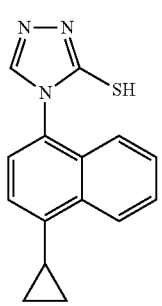

In one aspect, Compound 5, used in Process 2 described above is prepared by a process (Process 4) comprising (5-i) contacting a compound of structure:

(Compound 6)

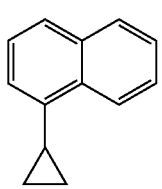

with nitric acid, water and a solvent to provide a compound of structure:

(Compound 7)

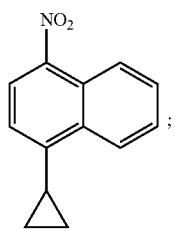

(5-ii) contacting Compound 7 with hydrogen, palladium on charcoal, and one or more solvents to provide a compound of structure:

(Compound 8)

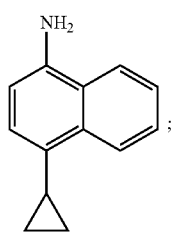

(5-iii-A) contacting Compound 8 with sodium thiocyanate, water and a solvent, and heating the mixture at a temperature of at least 130° C. to provide a compound of structure:

(Compound 9)

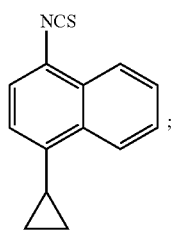

(5-iv-A) contacting Compound 9 of step (5-iii-A) with formyl hydrazine and a solvent to provide a compound of structure:

(Compound 10)

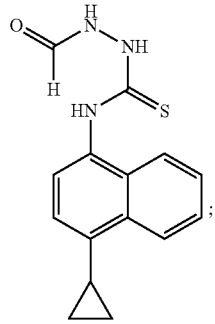

and
(5-vi) contacting Compound 10 of step (5-iv-A) with a base, water and a solvent to provide Compound 5:

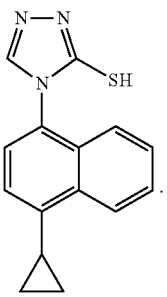
(Compound 5)

Provided herein is a compound of structure:

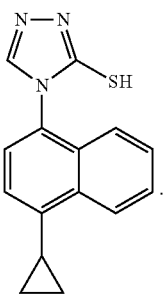
(Compound 5)

Provided herein is Compound 5, obtainable by Process 3 or Process 4 described above.

Provided herein is Compound 9, obtainable by Process 3 or Process 4 described above.

Provided herein is Compound 10, obtainable by Process 3 or Process 4 described above.

Provided herein is Compound 1, having at least 98% purity by area on an HPLC assay.

Provided herein is Compound 1, having at least 98% purity by area on an HPLC assay and which is obtained by the processes described above. In one embodiment, Compound 1 is prepared using Process 1, Process 2 and Process 3 described above. In another embodiment, Compound 1 is prepared using Process 1, Process 2 and Process 4 described above.

In one aspect, provided herein is a process (Process 5) for preparing

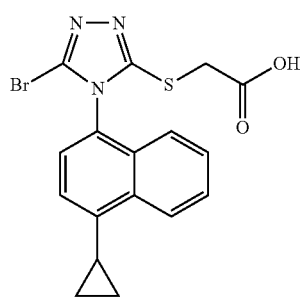
(Compound 1)

or

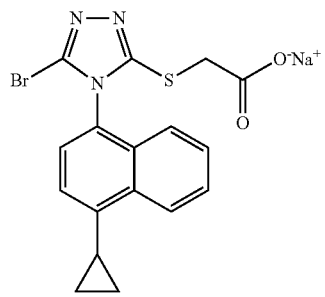
(Compound 4)

comprising:

(i) contacting a compound of structure

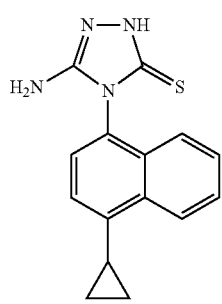
(Compound 11)

with a base, a solvent and a compound of Formula (IV):

$$\underset{X}{\overset{O}{\bigvee}}\underset{O}{\overset{}{\bigvee}}R;$$
Formula (IV)

wherein X is halo, tosylate, mesylate, triflate, or besylate, and R is —$C_1$-$C_{20}$ alkyl, —$C_1$-$C_{20}$ alkenyl, —$C_3$-$C_{10}$ cycloalkyl, or —$C_3$-$C_{10}$ cycloalkenyl;

to provide a compound of Formula (II):

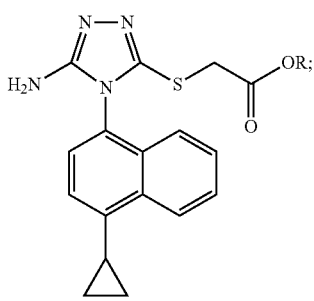
Formula (V)

(ii) contacting the compound of Formula (V) with copper (II) bromide, potassium nitrite and a solvent at a temperature between about 14° C. and about 22° C. to provide a compound of structure:

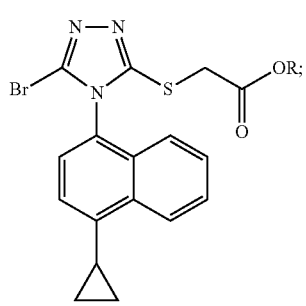

Formula (III)

(iii) contacting a solution of the compound of Formula (III) of step (ii) in a solvent with aqueous sodium hydroxide solution to provide a compound of structure:

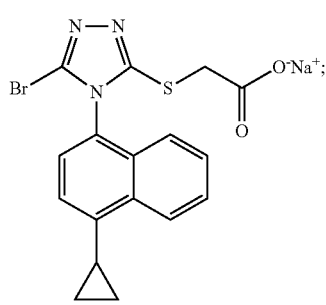

(Compound 4)

and (iv) optionally contacting an aqueous solution of Compound 4, of step (iii), with an acid to provide a mixture comprising Compound 1.

In some embodiments of the process described above, R is methyl, ethyl, propyl, isopropyl, butyl, isobutyl, tert-butyl, isoamyl, pentyl, hexyl, heptyl, octyl, nonyl, terpenyl, bornyl, allyl, linalyl or geranyl.

In certain embodiments of the process described above R is methyl or ethyl. In some specific embodiments of the process described above, R is methyl.

In some embodiments of the process described above, the compound of Formula (IV) of step (i) is selected from methyl bromoacetate, ethyl bromoacetate, methyl chloroacetate, and ethyl chloroacetate.

In some embodiments of the process described above, the acid of step (iv) is hydrochloric acid, hydrobromic acid, acetic acid, sulfuric acid, or phosphoric acid. In some specific embodiments of the process described above the acid of step (iv) is hydrobromic acid.

In some embodiments of the process described above, the process further comprises filtering the mixture of step (iv) to provide Compound 1 as a solid.

In some embodiments of the process described above, the process further comprises extracting the mixture of step (iv) with Ethyl Acetate and removing Ethyl Acetate to provide Compound 1 as a solid.

In some embodiments of the process described above, the process further comprises recrystallizing Compound 1 from Ethyl Acetate.

Provided herein is Compound 1, obtainable by the process described above.

Provided herein is Compound 3, obtainable by the process described above, and having the structure:

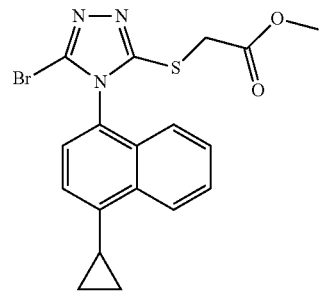

(Compound 3)

Provided herein is Compound 3-A, obtainable by the process described above, and having the structure:

(Compound 3-A)

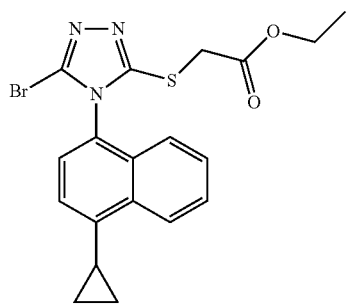

Provided herein is Compound 4, obtainable by the process described above.

Provided herein is Compound 12, obtainable by the process described above, and having the structure:

(Compound 12)

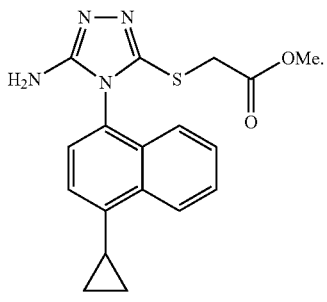

Provided herein is Compound 12-A, obtainable by the process described above, and having the structure:

(Compound 12-A)

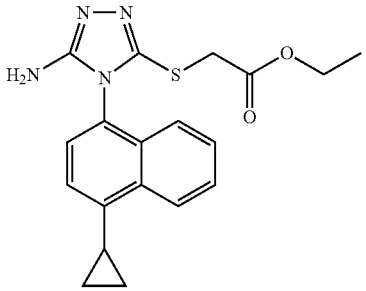

In a further aspect, any of the processes described above are suitable for synthesis of any compound of Formula (I).

In one aspect, provided herein is a process (Process 1a) for preparing a compound of formula (III):

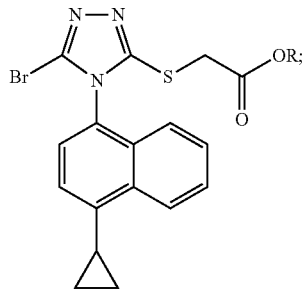

Formula (III)

comprising contacting a compound of Formula (II):

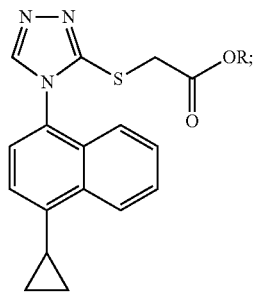

Formula (II)

wherein R is —$C_1$-$C_{20}$ alkyl, —$C_1$-$C_{20}$ alkenyl, —$C_3$-$C_{10}$ cycloalkyl, or —$C_3$-$C_{10}$ cycloalkenyl; with N-bromosuccinimide (NBS) and a solvent. In some embodiments, R is methyl, ethyl, propyl, isopropyl, butyl, isobutyl, tert-butyl, isoamyl, pentyl, hexyl, heptyl, octyl, nonyl, terpenyl, bornyl, allyl, linalyl or geranyl. In certain embodiments, R is methyl or ethyl. In some embodiments, the compound of Formula (II), the NBS and the solvent are stirred for at least 12 hours, and at a temperature of between about room temperature and about 32° C.

In some embodiments of the Process 1a described above, further comprises contacting the compound of Formula (III) with a sodium hydroxide solution to provide Compound 4:

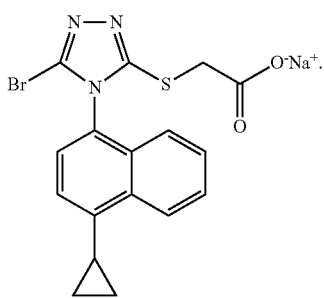

(Compound 4)

In certain embodiments, the process comprises crystallizing Compound 4 from the aqueous sodium hydroxide solution. In alternative embodiments, the process further comprises contacting Compound 4 with an acid to provide Compound 1:

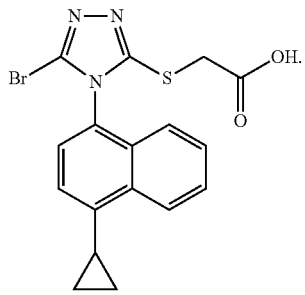

(Compound 1)

In certain embodiments the acid is hydrobromic acid. In another alternative embodiment, the process further comprises (a) dissolving Compound 4 in water and adding ethyl acetate to the mixture; and (b) contacting the biphasic mixture of step (a) with an acid and separating the organic phase to provide Compound 1.

Provided herein is a Compound 3 or Compound 3-A:

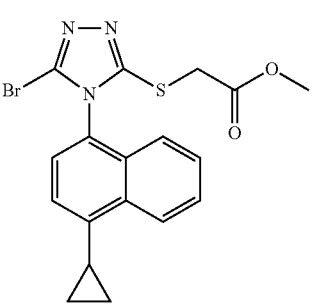

(Compound 3)

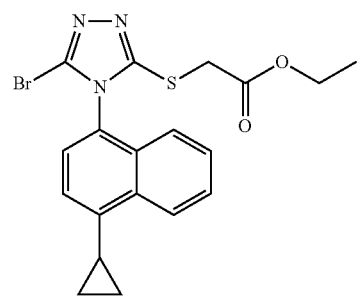

(Compound 3-A)

obtained by the processes according to Process 1a described above.

Provided here is a Compound 4:

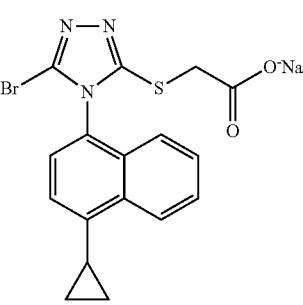

(Compound 4)

obtained by the processes according to Process 1a described above.

Provided here is a Compound 1:

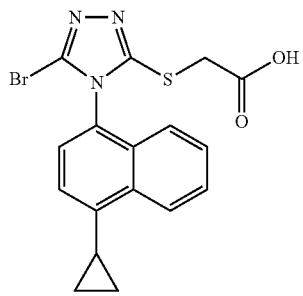

(Compound 1)

obtained by the processes according to Process 1a described above. In some embodiments, Compound 1 is a crystalline polymorph characterized by peaks at 10.46, 18.76, and 19.83°2θ±0.1°2θ. In certain embodiments, Compound 1 is the crystalline polymorph form 2.

In another aspect, provided here is a reaction mixture comprising a compound of Formula (II):

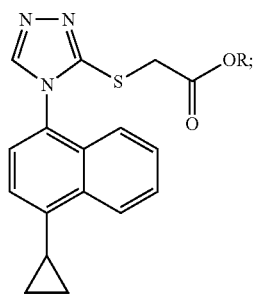

Formula (II)

wherein R is —$C_1$-$C_{20}$ alkyl, —$C_1$-$C_{20}$ alkenyl, —$C_3$-$C_{10}$ cycloalkyl, or —$C_3$-$C_{10}$ cycloalkenyl; a brominating agent; and a solvent. In some embodiments, the brominating agent is N-bromosuccinimide (NBS).

In a further aspect, provided herein is a reaction mixture comprising a compound of formula (III)

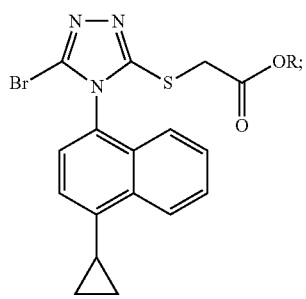

Formula (III)

wherein R is —$C_1$-$C_{20}$ alkyl, —$C_1$-$C_{20}$ alkenyl, —$C_3$-$C_{10}$ cycloalkyl, or —$C_3$-$C_{10}$ cycloalkenyl; a base; and a solvent. In some embodiments, the base is sodium hydroxide.

In another aspect, provided herein is a reaction mixture comprising Compound 4:

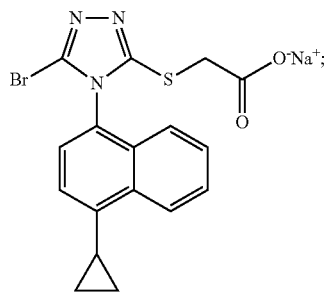

(Compound 4)

an acid; and a solvent. In some embodiments, the acid is hydrobromic acid.

In one aspect, provided herein is a process (Process 2a) wherein the compound of Formula (II), used in Process 1a above, is prepared by a process comprising contacting compound 5:

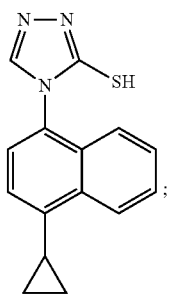

(Compound 5)

with a base, a solvent, and a compound of Formula (IV):
wherein:

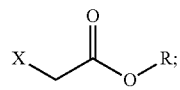

Formula (IV)

X is halo, tosylate, mesylate, triflate, or besylate; and
R is —$C_1$-$C_{20}$ alkyl, —$C_1$-$C_{20}$ alkenyl, —$C_3$-$C_{10}$ cycloalkyl, or —$C_3$-$C_{10}$ cycloalkenyl.

In some embodiments, the compound of Formula (IV) is selected from methyl bromoacetate, ethyl bromoacetate, methyl chloroacetate, and ethyl chloroacetate. In certain embodiments, a crude reaction product comprising a compound of Formula (II) is washed with a cooled mixture of ethyl acetate and isopropanol.

Also provided herein is a Compound 2 or Compound 2-A:

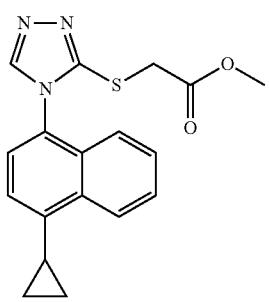
(Compound 2)

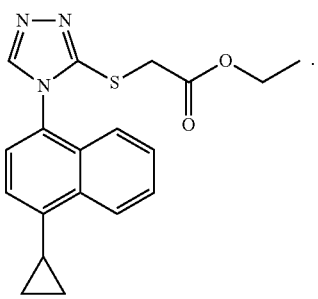
(Compound 2-A)

In certain embodiments, the Compound 2 or Compound 2-A are obtained by the processes according to Process 2a described above.

In another aspect, provided herein is a reaction mixture comprising Compound 5:

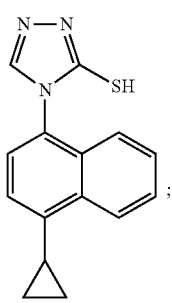
(Compound 5)

a compound of Formula (IV):

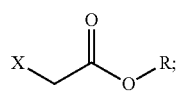
Formula (IV)

wherein:

X is a leaving group; and

R is —$C_1$-$C_{20}$ alkyl, —$C_1$-$C_{20}$ alkenyl, —$C_3$-$C_{10}$ cycloalkyl or —$C_3$-$C_{10}$ cycloalkenyl;

a base; and a solvent. In some embodiments, the compound of Formula (IV) is methyl bromoacetate, ethyl bromoacetate, methyl chloroacetate, or ethyl chloroacetate.

In another aspect, provided herein is a process (Process 3a) wherein Compound 5, used in Process 2a above, is prepared by a process comprising:

(5-i) contacting Compound 6:

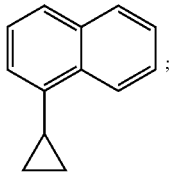
(Compound 6)

with nitric acid, water and a solvent to provide compound 7:

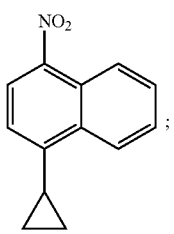
(Compound 7)

(5-ii) contacting Compound 7 with hydrogen, palladium on charcoal, and one or more solvents to provide Compound 8:

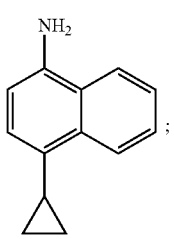
(Compound 8)

(5-iii) contacting Compound 8 with an acid to provide a salt of Compound 8;

(5-iv) contacting the salt of Compound 8 of step (5-iii) with a base, thiophosgene and a solvent to provide Compound 9:

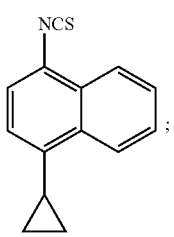
(Compound 9)

(5-v) contacting Compound 9 with formyl hydrazine and a solvent to provide Compound 10:

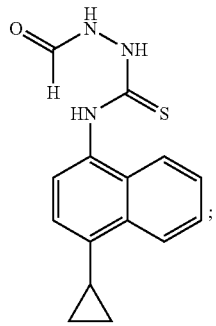
(Compound 10)

and (5-vi) contacting Compound 10 with a base, water and a solvent to provide Compound 5:

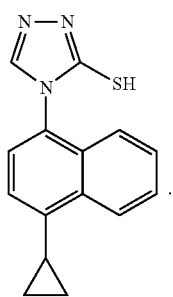
(Compound 5)

Also provided herein is a compound selected from Compounds I-X: 2-(4-(4-cyclopropylnaphthalen-1-yl)-4H-1,2,4-triazol-3-ylthio)acetic acid (Compound I); 2-(4-(4-cyclopropylnaphthalen-1-yl)-5-hydroxy-4H-1,2,4-triazol-3-ylthio)acetic acid (Compound II); 2-(5-amino-4-(4-cyclopropylnaphthalen-1-yl)-4H-1,2,4-triazol-3-ylthio)acetic acid (Compound III); 2-(5-bromo-4-(1-cyclopropylnaphthalen-2-yl)-4H-1,2,4-triazol-3-ylthio)acetic acid (Compound IV); 2-(5-bromo-4-(4-methylnaphthalen-1-yl)-4H-1,2,4-triazol-3-ylthio)acetic acid (Compound V); 2-(5-bromo-4-(4-propylnaphthalen-1-yl)-4H-1,2,4-triazol-3-ylthio)acetic acid (Compound VI); 2-(5-bromo-4-(5-cyclopropylnaphthalen-1-yl)-4H-1,2,4-triazol-3-ylthio)acetic acid (Compound VII); 2-(5-bromo-4-(naphthalen-1-yl)-4H-1,2,4-triazol-3-ylthio)acetic acid (Compound VIII); 2-(5-chloro-4-(4-cyclopropylnaphthalen-1-yl)-4H-1,2,4-triazol-3-ylthio)acetic acid (Compound IX); and 4-(5-(carboxymethylthio)-4-(4-cyclopropylnaphthalen-1-yl)-4H-1,2,4-triazol-3-ylamino)-4-oxobutanoic acid (Compound X). In some embodiments, a sample of 2-(5-bromo-4-(4-cyclopropylnaphthalen-1-yl)-4H-1,2,4-triazol-3-ylthio)acetic acid comprises less than about 2%, less than about 1.5%, less than about 1.0%, less than about 0.5%, less than about 0.4%, less than about 0.3%, less than about 0.2%, less than about 0.1%, less than about 0.05%, less than 0.02% of any one of Compounds I-X. In preferred embodiments, a sample of 2-(5-bromo-4-(4-cyclopropylnaphthalen-1-yl)-4H-1,2,4-triazol-3-ylthio)acetic acid comprises less than about 0.5% of any one of Compounds I-X.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
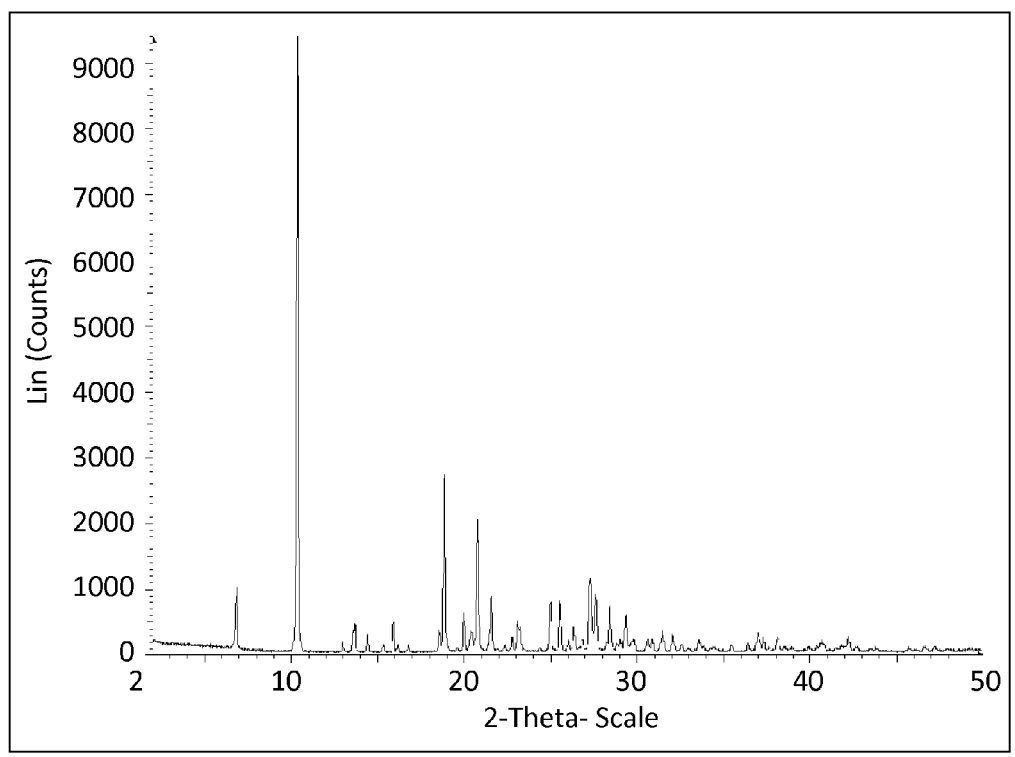
FIG. 1 represents an illustrative X-ray Powder Diffraction Pattern of Polymorph form 1 (Raw Data).

Good manufacturing practices are usually required for large scale manufacture of clinically useful drug candidates. Provided herein are certain processes and methods for the manufacture of compounds of Formula (I):

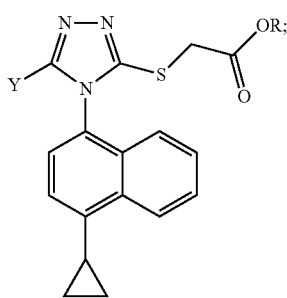

Formula (I)

wherein
R is H, —C$_1$-C$_{20}$ alkyl, —C$_1$-C$_{20}$ alkenyl, —C$_3$-C$_{10}$ cycloalkyl, —C$_3$-C$_{10}$ cycloalkenyl, or R is a counter ion; and Y is H, OH, NH$_2$, F, Cl, Br, or I.

The processes and methods of syntheses provided herein overcome certain manufacturing drawbacks and allow for synthesis of high purity compounds while reducing waste and/or by-products, and reducing the use of corrosive materials. The improved processes and methods of synthesis of compounds of Formula (I) described herein allow for large-scale production compliant with good manufacturing practice (GMP) guidelines.

Certain Chemical Terminology

Unless defined otherwise, all technical and scientific terms used herein have the same meaning as is commonly understood by one of skill in the art to which the claimed subject matter belongs. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed herein are the standard definitions. Standard techniques can be used for chemical syntheses, chemical analyses, pharmaceutical preparation, formulation, and delivery, and treatment of individuals. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, —CH$_2$O— is equivalent to —OCH$_2$—.

Unless otherwise noted, the use of general chemical terms, such as though not limited to "alkyl," "amine," "aryl," are equivalent to their optionally substituted forms. For example, "alkyl," as used herein, includes optionally substituted alkyl.

In some embodiments, the compounds presented herein possess one or more stereocenters. In some embodiments, the stereocenter is in the R configuration, the S configuration, or combinations thereof. In some embodiments, the compounds presented herein possess one or more double bonds. In some embodiments, the compounds presented herein possess one or more double bonds wherein each double bond exists in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Techniques for inverting or leaving unchanged a particular stereocenter, and those for resolving mixtures of stereoisomers are found, for example, Furniss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, *Acc. Chem. Res.* 1990, 23, 128.

The terms "moiety", "chemical moiety", "group" and "chemical group", as used herein refer to a specific segment or functional group of a molecule. Chemical moieties are often recognized chemical entities embedded in or appended to a molecule.

The term "reactant," as used herein, refers to a nucleophile or electrophile used to create covalent linkages.

The term "bond" or "single bond" refers to a chemical bond between two atoms, or two moieties when the atoms joined by the bond are considered to be part of larger substructure.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "alkylene" as used herein, alone or in combination, refers to a diradical derived from the above-defined monoradical, alkyl. Examples include, but are not limited to methylene (—$CH_2$—), ethylene (—$CH_2CH_2$—), propylene (—$CH_2CH_2CH_2$—), isopropylene (—$CH(CH_3)CH_2$—) and the like.

The term "alkenyl" as used herein, alone or in combination, refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" or "$C_{2-6}$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated.

The term "alkenylene" as used herein, alone or in combination, refers to a diradical derived from the above-defined monoradical alkenyl. Examples include, but are not limited to ethenylene (—CH=CH—), the propenylene isomers (e.g., —$CH_2$CH=CH— and —C($CH_3$)=CH—) and the like.

The term "aliphatic" as used herein, alone or in combination, refers to an optionally substituted, straight-chain or branched-chain, non-cyclic, saturated, partially unsaturated, or fully unsaturated nonaromatic hydrocarbon. Thus, the term collectively includes alkyl, alkenyl and alkynyl groups.

The term "carbon chain" as used herein, alone or in combination, refers to any alkyl, alkenyl, alkynyl, heteroalkyl, heteroalkenyl or heteroalkynyl group, which is linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "fused" as used herein, alone or in combination, refers to cyclic structures in which two or more rings share one or more bonds.

The term "cycloalkyl" as used herein, alone or in combination, refers to an optionally substituted, saturated, hydrocarbon monoradical ring, containing from three to about fifteen ring carbon atoms or from three to about ten ring carbon atoms, though may include additional, non-ring carbon atoms as substituents (e.g. methylcyclopropyl). Whenever it appears herein, a numerical range such as "$C_3$-$C_6$ cycloalkyl" or "$C_{3-6}$ cycloalkyl", means that the cycloalkyl group may consist of 3 carbon atoms, 4 carbon atoms, 5 carbon atoms or 6 carbon atoms, i.e., is cyclopropyl, cyclobutyl, cyclopentyl or cycloheptyl, although the present definition also covers the occurrence of the term "cycloalkyl" where no numerical range is designated. The term includes fused, non-fused, bridged and spiro radicals. A fused cycloalkyl may contain from two to four fused rings where the ring of attachment is a cycloalkyl ring, and the other individual rings may be alicyclic, heterocyclic, aromatic, heteroaromatic or any combination thereof. Examples include, but are not limited to cyclopropyl, cyclopentyl, cyclohexyl, decalinyl, and bicyclo[2.2.1]heptyl and adamantyl ring systems. Illustrative examples include, but are not limited to the following moieties:

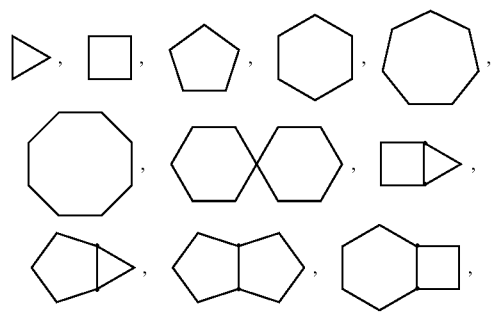

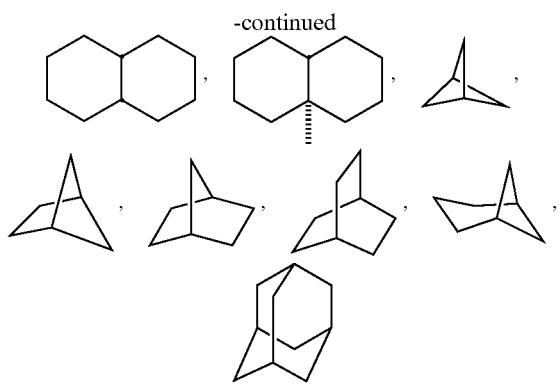

and the like.

The term "cycloalkenyl" as used herein, alone or in combination, refers to an optionally substituted hydrocarbon non-aromatic, monoradical ring, having one or more carbon-carbon double-bonds and from three to about twenty ring carbon atoms, three to about twelve ring carbon atoms, or from three to about ten ring carbon atoms. The term includes fused, non-fused, bridged and spiro radicals. A fused cycloalkenyl may contain from two to four fused rings where the ring of attachment is a cycloalkenyl ring, and the other individual rings may be alicyclic, heterocyclic, aromatic, heteroaromatic or any combination thereof. Fused ring systems may be fused across a bond that is a carbon-carbon single bond or a carbon-carbon double bond. Examples of cycloalkenyls include, but are not limited to cyclohexenyl, cyclopentadienyl and bicyclo[2.2.1]hept-2-ene ring systems. Illustrative examples include, but are not limited to the following moieties:

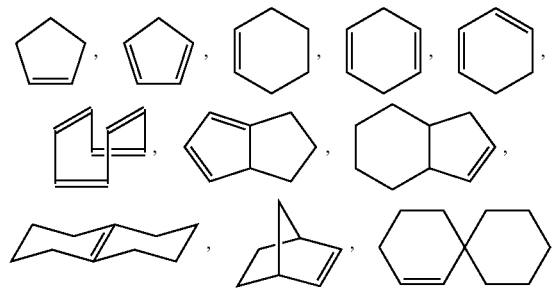

and the like.

The terms "alicyclyl" or "alicyclic" as used herein, alone or in combination, refer to an optionally substituted, saturated, partially unsaturated, or fully unsaturated nonaromatic hydrocarbon ring systems containing from three to about twenty ring carbon atoms, three to about twelve ring carbon atoms, or from three to about ten ring carbon atoms. Thus, the terms collectively include cycloalkyl and cycloalkenyl groups.

The term "carbocyclyl" as used herein, alone or in combination, refers collectively to alicyclyl and aryl groups; i.e. all carbon, covalently closed ring structures, which may be saturated, partially unsaturated, fully unsaturated or aromatic. Carbocyclic rings can be formed by three, four, five, six, seven, eight, nine, or more than nine carbon atoms. Carbocycles can be optionally substituted. The term distinguishes carbocyclic from heterocyclic rings in which the ring backbone contains at least one atom which is different from carbon.

The terms "halogen", "halo" or "halide" as used herein, alone or in combination refer to fluoro, chloro, bromo and iodo.

The term "hydroxy" as used herein, alone or in combination, refers to the monoradical —OH.

The terms "carboxy" or "carboxyl" as used herein, alone or in combination, refer to the moiety —C(O)OH, which may also be written as —COOH. A "carboxylate anion" is a deprotonated carboxyl moiety and is written as —COO or —COO⁻.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

As used herein, "3,5-disubstituted 4-(4-$R^C$-naphthalen-1-yl)-4H-1,2,4-triazole" refers to:

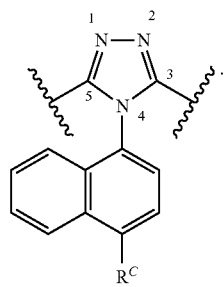

As used herein, "3-substituted-5-bromo-4-(4-cyclopropyl-naphthalen-1-yl)-4H-1,2,4-triazole" refers to:

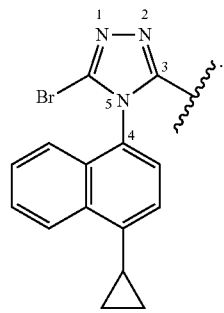 [SMILES: *c1nnc(Br)n1-c1ccc(C2CC2)c2ccccc12]

Figure 2:
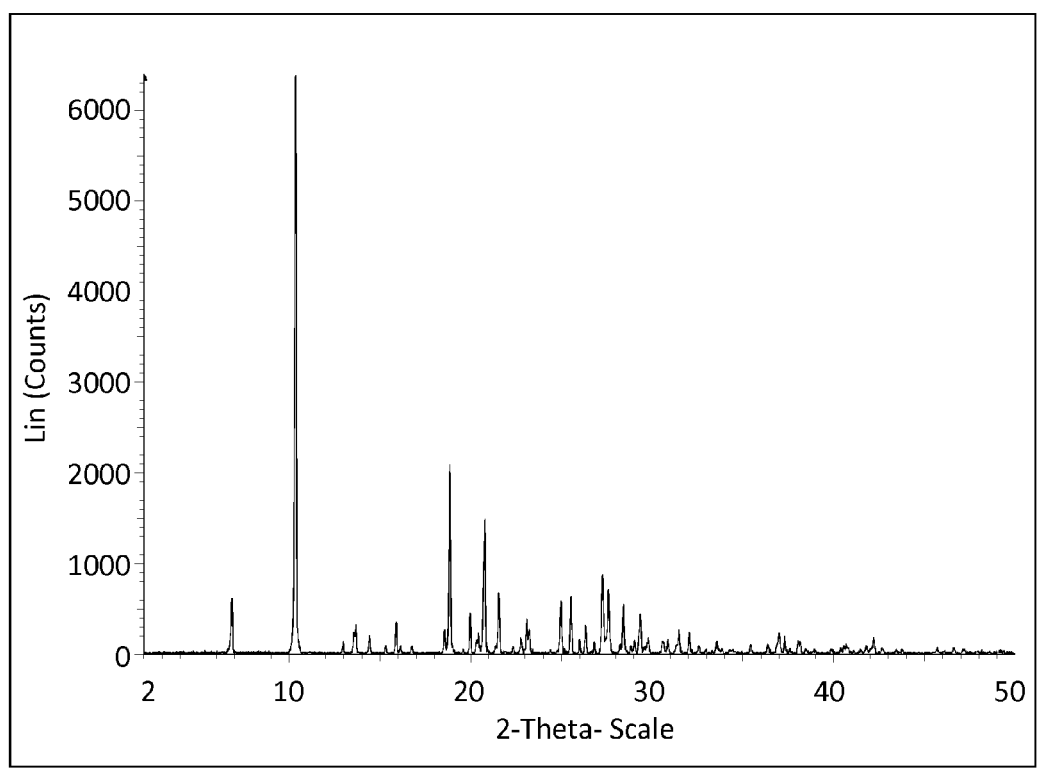
FIG. 2 represents an illustrative X-ray Powder Diffraction Pattern of Polymorph form 1 (Background Subtracted and Kα2 Stripped).
Figure 3:
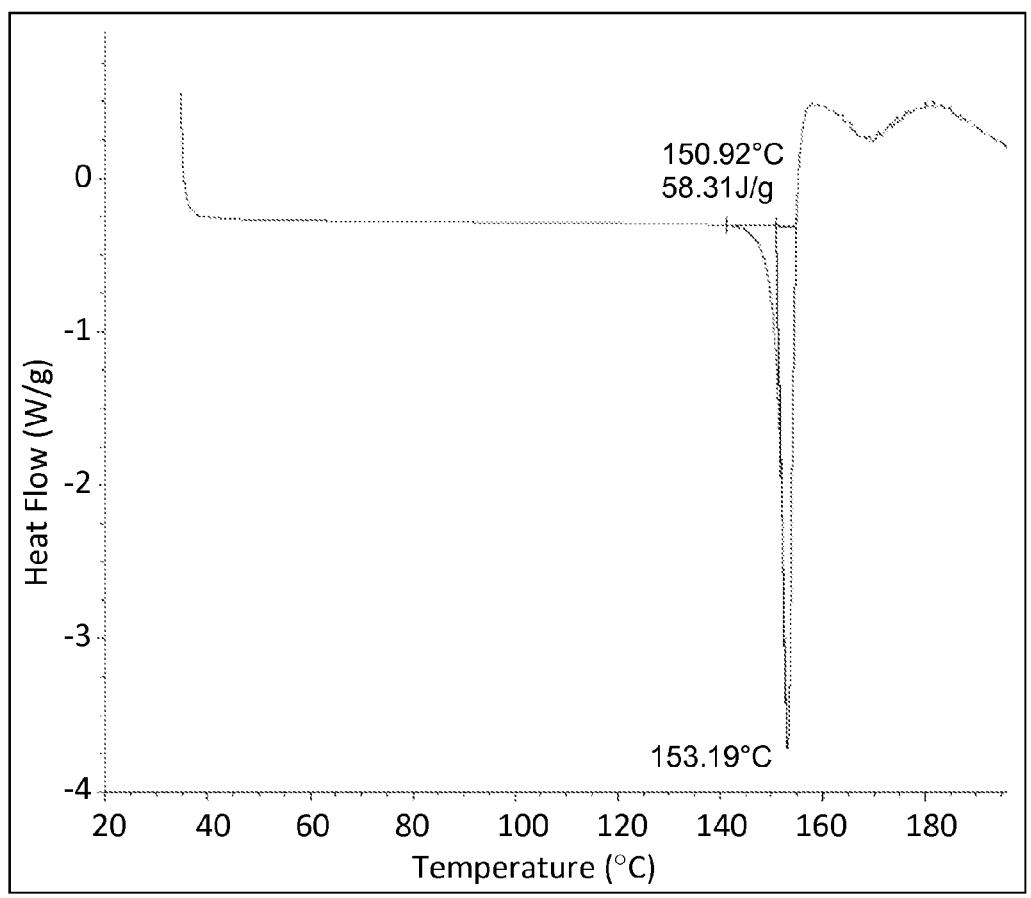
FIG. 3 represents an illustrative Differential Scanning calorimetry pattern of Polymorph form 1.

The term "polymorph form 1" refers to a crystalline form of 2-(5-bromo-4-(4-cyclopropyl naphthalen-1-yl)-4H-1,2,4-triazol-3-ylthio)acetic acid that exhibits an x-ray powder diffraction pattern substantially the same as that shown in FIG. 1, and/or FIG. 2 and/or a differential scanning calorimetry profile substantially the same as that shown in FIG. 3.

Figure 5:
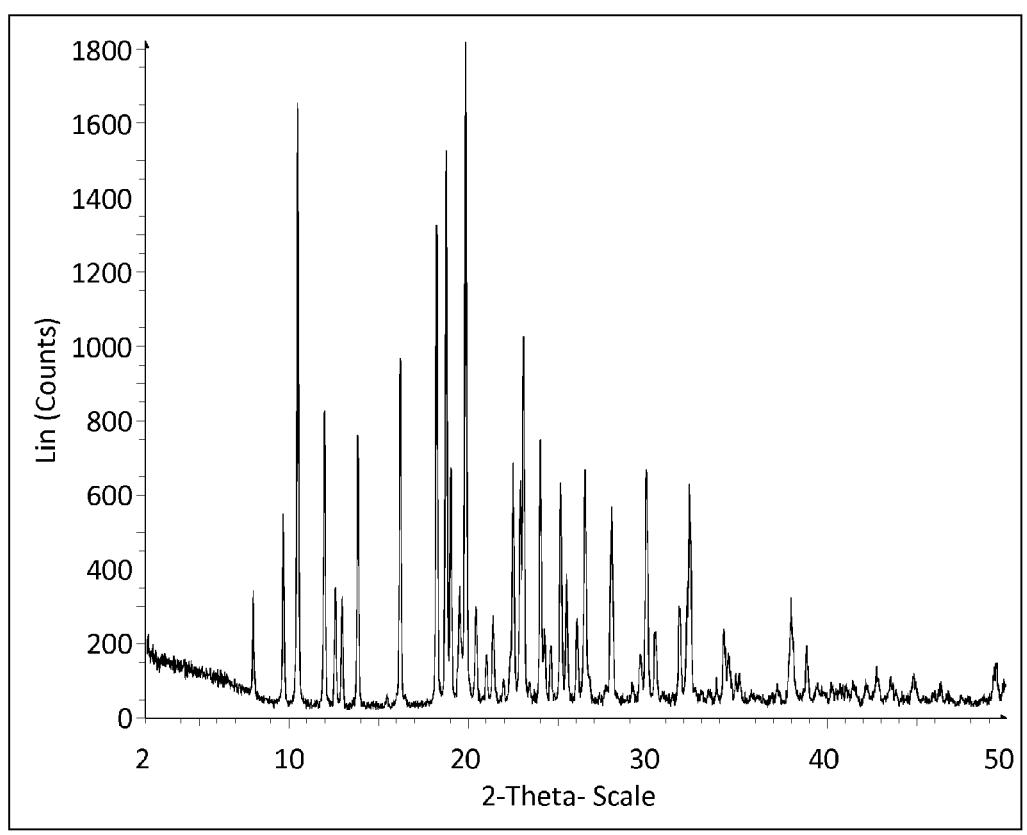
FIG. 5 represents an illustrative X-ray Powder Diffraction Pattern of Polymorph form 2 (Raw Data).
Figure 6:
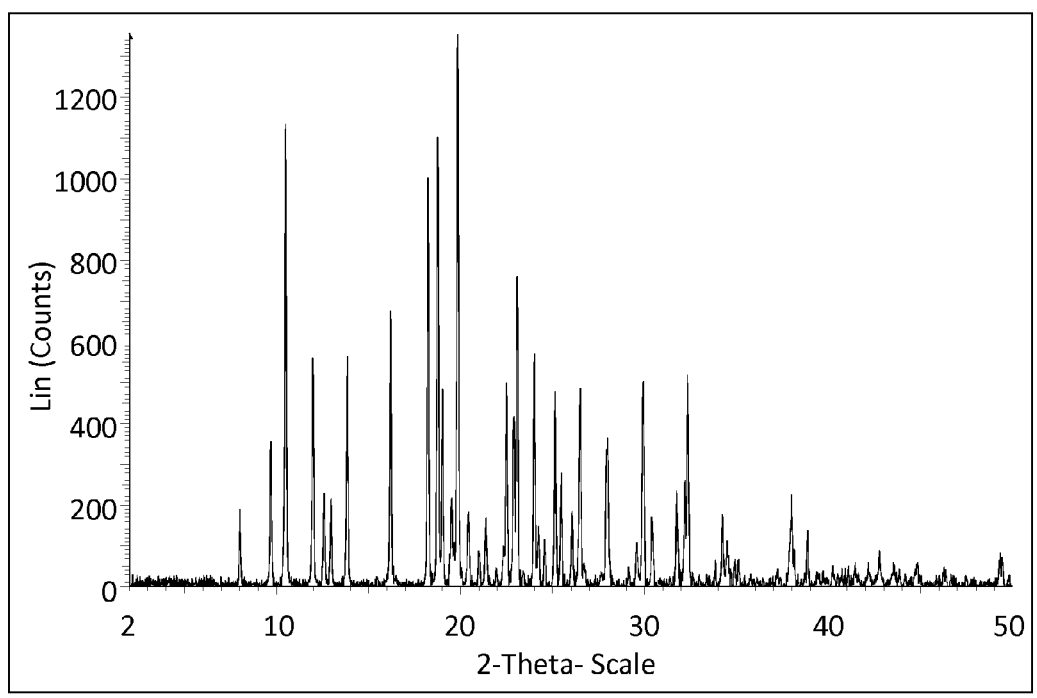
FIG. 6 represents an illustrative X-ray Powder Diffraction Pattern of Polymorph form 2 (Background Subtracted and Kα2 Stripped).
Figure 8:
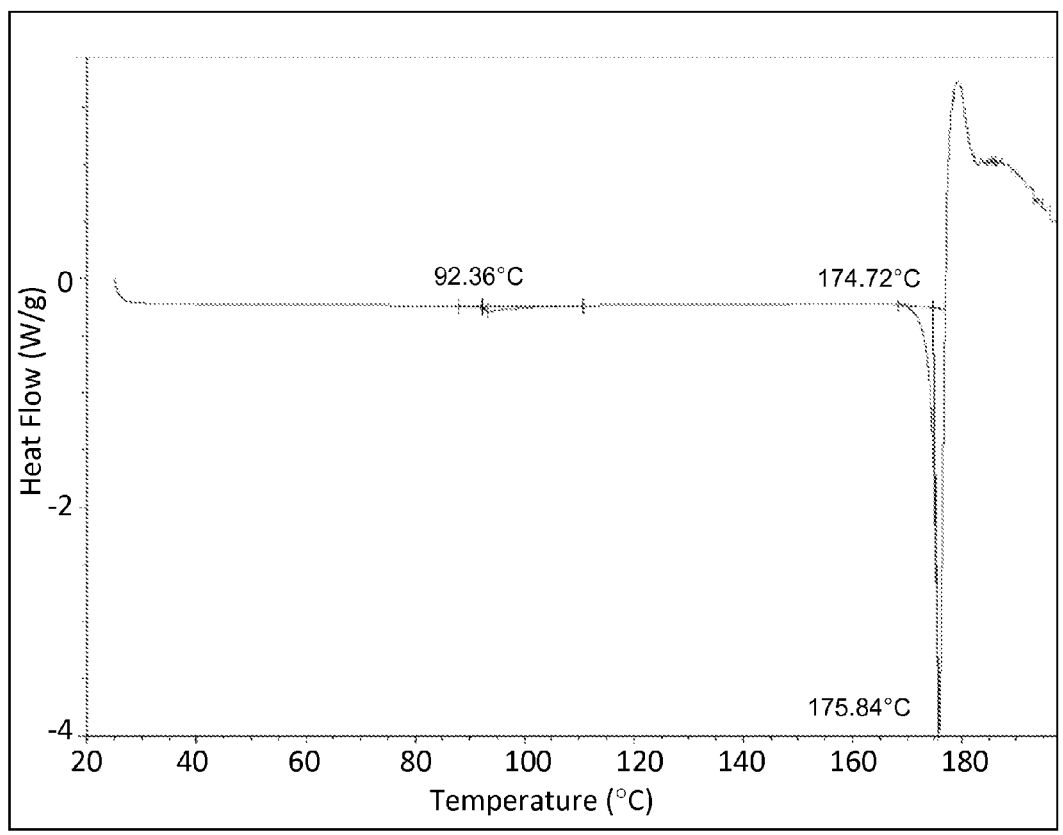
FIG. 8 represents an illustrative Differential Scanning calorimetry pattern of Polymorph form 2.

The term "polymorph form 2" refers to a crystalline form of 2-(5-bromo-4-(4-cyclopropyl naphthalen-1-yl)-4H-1,2,4-triazol-3-ylthio)acetic acid that exhibits an x-ray powder diffraction pattern substantially the same as that shown in FIG. 5, and/or FIG. 6 and/or a differential scanning calorimetry profile substantially the same as that shown in FIG. 8.

Figure 13:
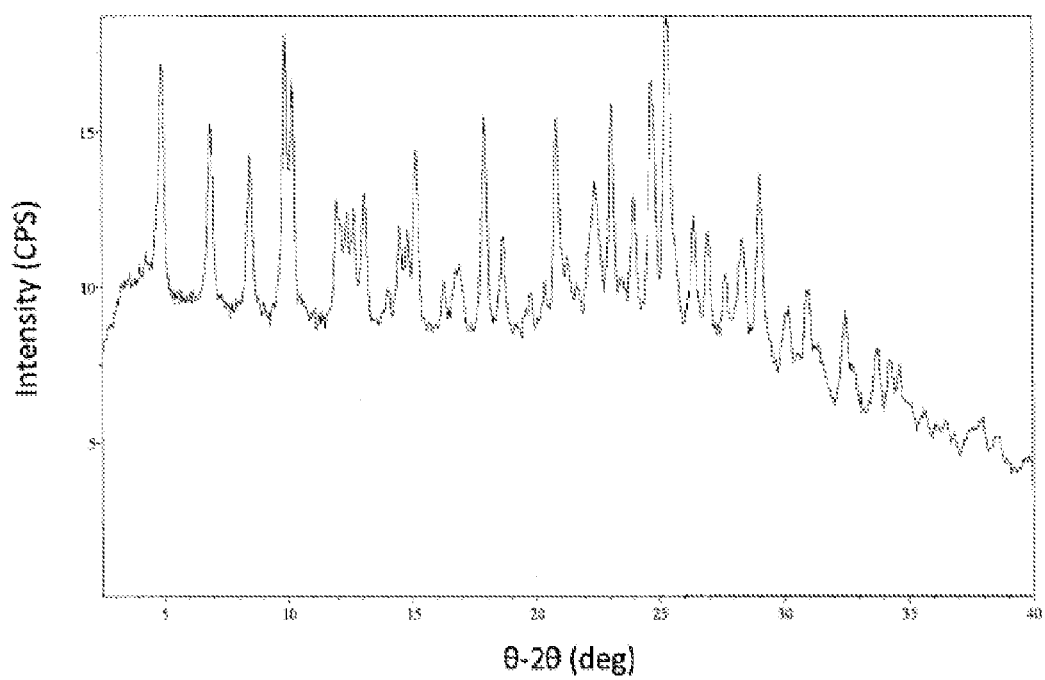
FIG. 13 represents an illustrative X-ray Powder Diffraction Pattern of Polymorph Form A.
Figure 14:
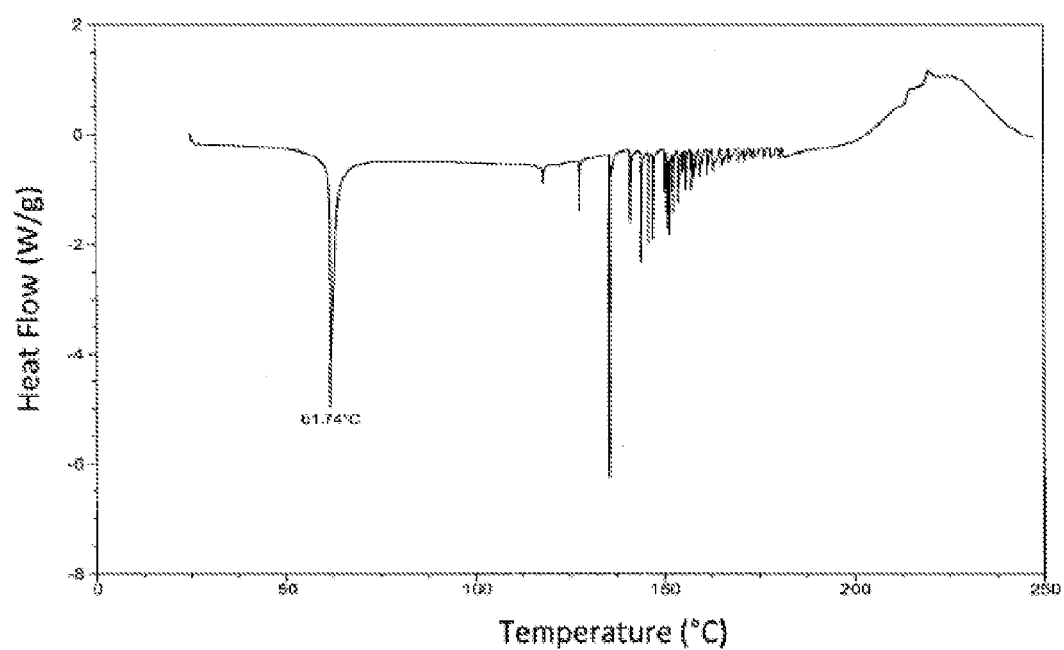
FIG. 14 represents an illustrative Differential Scanning calorimetry pattern of Polymorph Form A.

The term "polymorph form A" refers to a crystalline form of sodium 2-(5-bromo-4-(4-cyclopropylnaphthalen-1-yl)-4H-1,2,4-triazol-3-ylthio)acetate that exhibits an x-ray powder diffraction pattern substantially the same as that shown in FIG. 13, and/or a differential scanning calorimetry profile substantially the same as that shown in FIG. 14.

Figure 17:
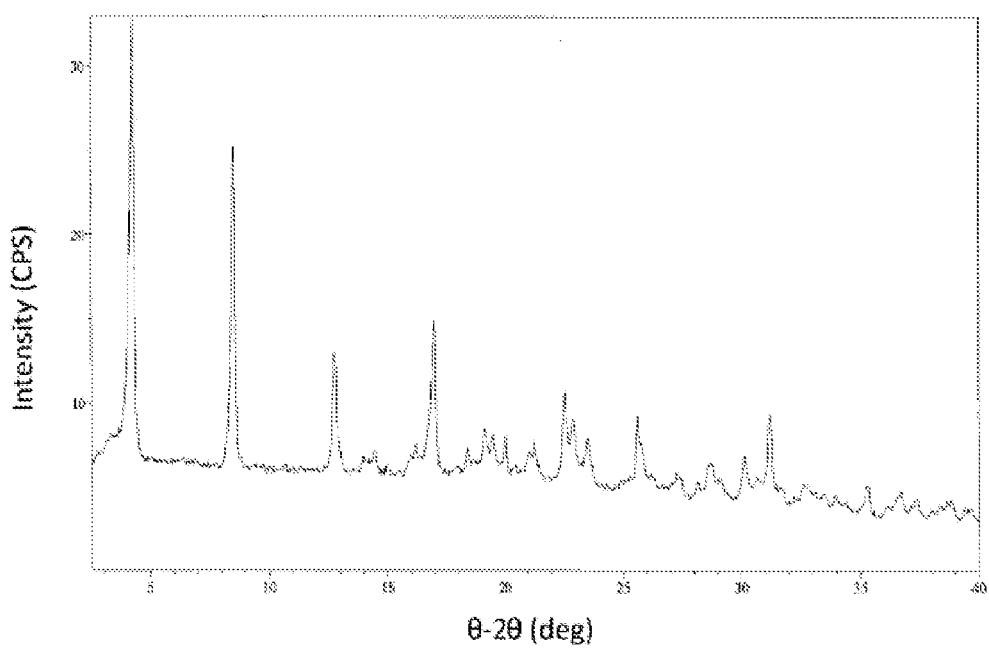
FIG. 17 represents an illustrative X-ray Powder Diffraction Pattern of Polymorph Form B.
Figure 18:
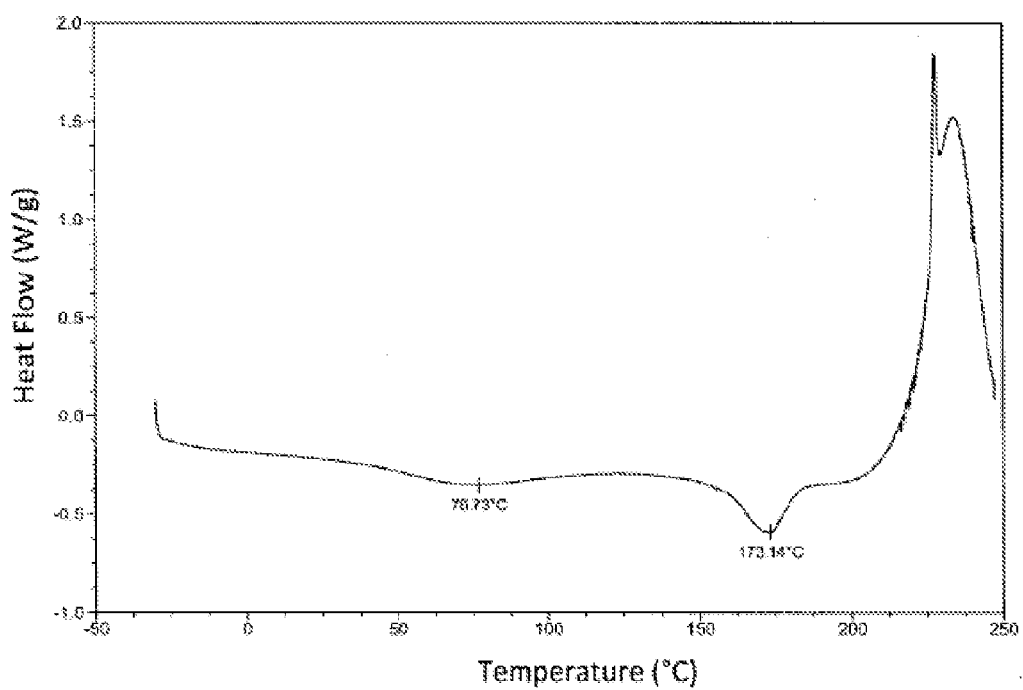
FIG. 18 represents an illustrative Differential Scanning calorimetry pattern of Polymorph Form B.

The term "polymorph form B" refers to a crystalline form of sodium 2-(5-bromo-4-(4-cyclopropylnaphthalen-1-yl)-4H-1,2,4-triazol-3-ylthio)acetate that exhibits an x-ray powder diffraction pattern substantially the same as that shown in FIG. 17, and/or a differential scanning calorimetry profile substantially the same as that shown in FIG. 18.

Figure 19:
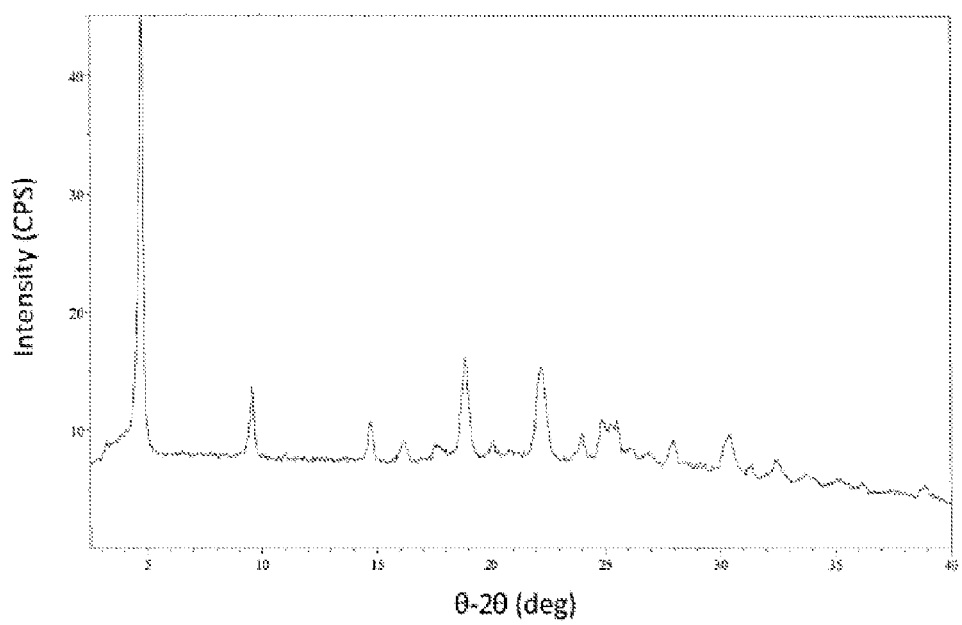
FIG. 19 represents an illustrative X-ray Powder Diffraction Pattern of Polymorph Form B'.
Figure 20:
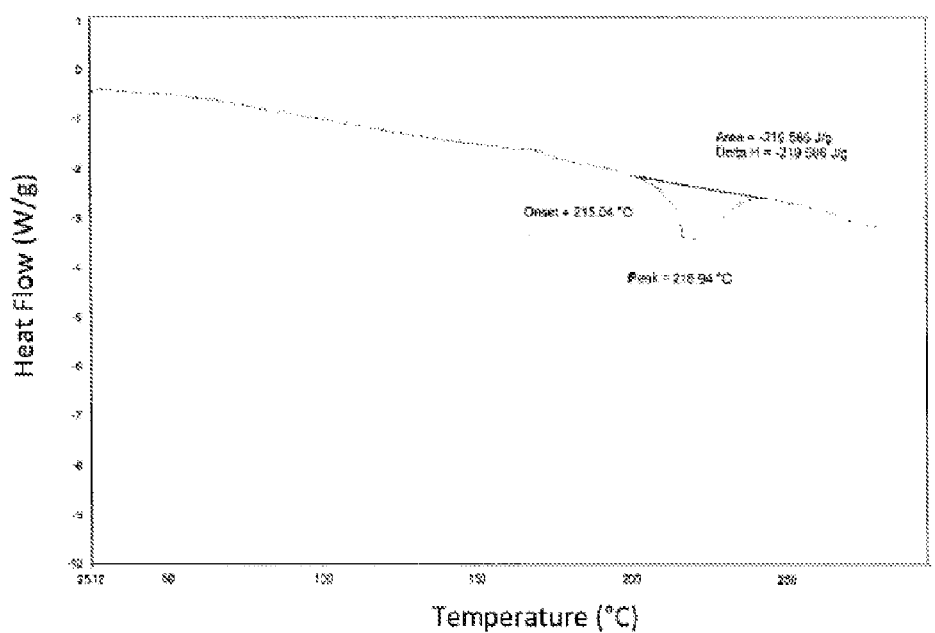
FIG. 20 represents an illustrative Differential Scanning calorimetry pattern of Polymorph Form B'.

The term "polymorph form B'" refers to a crystalline form of sodium 2-(5-bromo-4-(4-cyclopropylnaphthalen-1-yl)-4H-1,2,4-triazol-3-ylthio)acetate that exhibits an x-ray powder diffraction pattern substantially the same as that shown in FIG. 19, and/or a differential scanning calorimetry profile substantially the same as that shown in FIG. 20.

As used herein, a "counter ion" is an ion the presence of which allows the formation of an overall neutrally charged species. Accordingly, in one instance, a counter ion is a positively charged ion, e.g., for a compound of Formula (I), which balances the negative charge associated with a carboxylate anion of a compound of Formula (I) and allows the formation of an overall neutrally charged species. Examples of counter ions for compounds of Formula (I) include and are not limited to Na+, K+, Li+, Cs+, Mg++, Fe+++, Al+++, or any other pharmaceutically acceptable organic or inorganic cation. Where the cation has more than one unit charge (e.g., a Mg++), it is understood that one or more carboxylate anionic moieties (e.g., carboxylate moieties of compounds of Formula (I)) will be needed to form an overall neutrally charged species. In another instance, a counter ion is a negatively charged ion. For example, for Compound 8, a negatively charged counter ion balances the positive charge associated with a protonated form of Compound 8. Examples of such negatively charged counter ions include and are not limited to oxalate, citrate, tartarate, acetate, chloride, bromide, fluoride, or any other pharmaceutically acceptable organic or inorganic anion.

Initial Attempts

Initial efforts for identification of optimal conditions for synthesis of compounds of Formula (I) including e.g., Compound 1 and Compound 4, focused on Compound 11 (3-amino-4-(4-cyclopropylnaphthalen-1-yl)-1H-1,2,4-triazole-5 (4H)-thione) as the starting material. Scheme 1 shows an exemplary synthesis of Compound 1 and Compound 4.

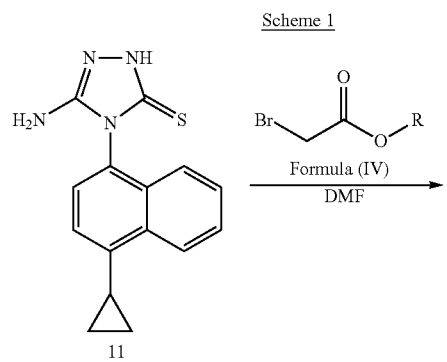

Scheme 1

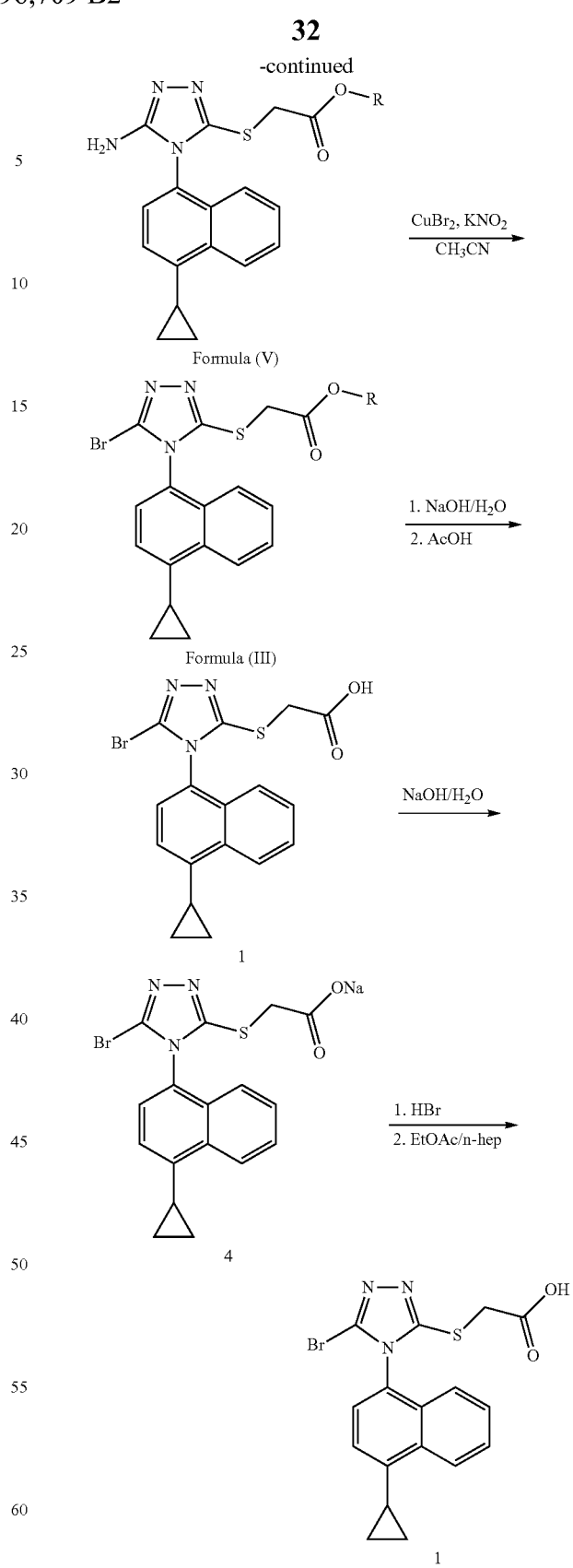

Starting with Compound 11, a reaction with a compound of Formula (IV) in the presence of DMF as a solvent provides a compound of Formula (V). Any reagent of Formula (IV) may be used. In one embodiment, the reaction of Compound 11 is carried out with bromo methyl acetate

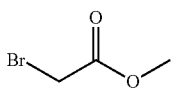

or chloro methyl acetate

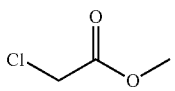

to provide a compound of Formula (V) wherein R is methyl (Compound 2). In a different embodiment, the reaction of Compound 11 is carried out with bromo ethyl acetate

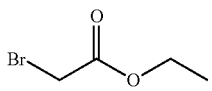

or chloroethyl acetate

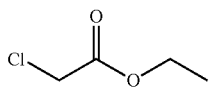

to provide a compound of Formula (V) wherein R is ethyl (Compound 2-A). In another embodiment, the reaction of Compound 11 is carried out with bromoacetic acid

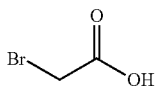

to provide a compound of Formula (V) wherein R is H. Any suitable solvent is used. In one embodiment, the solvent is DMF. In alternate embodiments, the solvent is dioxane, acetonitrile, chloroform, dichloromethane, tetrahydrofuran (THF), N-methyl pyrrolidone (NMP), dimethylsulfoxide (DMSO) and the like.

The compound of Formula (V) is then subjected to a reaction with Copper (II) bromide in the presence of potassium nitrite and a solvent and the reaction temperature is maintained at about room temperature or below, to provide a compound of Formula (III). In some embodiments, the compound of formula (V) is subjected to $CuCl_2/KNO_2$, $CuCl_2/NaNO_2$, $CuBr_2/NaNO_2$, $pTsOH/NaNO_2/KBr$, or $Br_2$. In one embodiment, the reaction temperature is between about 14° C. and about 22° C. In another embodiment, the reaction temperature is between about 12° C. and about 25° C. Any suitable solvent is used. In one embodiment, the solvent is acetonitrile. In a different embodiment, the solvent is dichloromethane, NMP, dioxane, THF and the like. In one embodiment, the reaction provides a compound of Formula (III) which is Compound 3. In another embodiment, the reaction provides a compound of Formula (III) which is Compound 3-A. In another embodiment wherein R is H, the reaction provides Compound 1.

Contemplated within the scope of compounds of Formula (III) are ester compounds that are prodrugs of Compound 1. Examples of such esters include and are not limited to methyl, ethyl, propyl, isopropyl, butyl, isobutyl, tert-butyl, isoamyl, pentyl, hexyl, heptyl, octyl, nonyl, terpenyl, bornyl, allyl, linalyl and/or geranyl esters.

The ester group in the compound of Formula (III) is hydrolyzed using any suitable acid including and not limited to acetic, trifluoroacetic, sulfuric, nitric, phosphoric, hydrochloric or hydrobromic acid to provide Compound 1.

Compound 1 is then converted to a salt. In one embodiment, Compound 1 is stirred in aqueous sodium hydroxide to provide Compound 4. In some embodiments, Compound 4 is a crystalline polymorph characterized by peaks at 4.90, 9.83, and $25.29°2\theta\pm0.1°2\theta$. In some embodiments, Compound 4 is crystalline polymorph form A. In alternate embodiments, Compound 1 is stirred in aqueous potassium hydroxide, lithium hydroxide, cesium hydroxide or any other suitable basic solution to provide a compound of Formula (I) where in R is a counter ion. In some of such embodiments, an alcohol (e.g., methanol, ethanol, isopropanol) is used as a co-solvent for the reaction step comprising conversion of Compound 1 to a salt.

An aqueous solution of Compound 4 (or the compound of Formula (I) in which R is a counter ion) is acidified using a suitable acid such as hydrobromic acid. Other acids that are suitable for this step include and are not limited to acetic, trifluoroacetic, sulfuric, nitric, phosphoric, hydrochloric acid, and the like. The mixture is extracted with a suitable organic solvent such as Ethyl acetate. Other solvents suitable for extraction include and are not limited to dichloromethane, tert butyl methyl ether, tert-butanol and the like. Compound 1 is then optionally recrystallized from EtOAc. In some embodiments, Compound 1 is recrystallized from Ethyl Acetate and using n-heptanes as a counter solvent. It will be appreciated that any other suitable solvent or combination of solvents may be used for recrystallization of Compound 1.

In some embodiments, Compound 1 is a crystalline polymorph characterized by peaks at 10.32, 18.84, and $20.75°2\theta\pm0.1°2\theta$. In certain embodiments, Compound 1 is crystalline polymorph form 1. In other embodiments, Compound 1 is a crystalline polymorph characterized by peaks at 10.46, 18.76, and $19.83°2\theta\pm0.1°2\theta$. In certain embodiments, Compound 1 is crystalline polymorph form 2.

Synthesis of Compound 11—First Method

The synthesis of Compound 11, described in Scheme 1, was achieved, in one exemplary embodiment, using the sequence of reactions described in Scheme 2.

Scheme 2

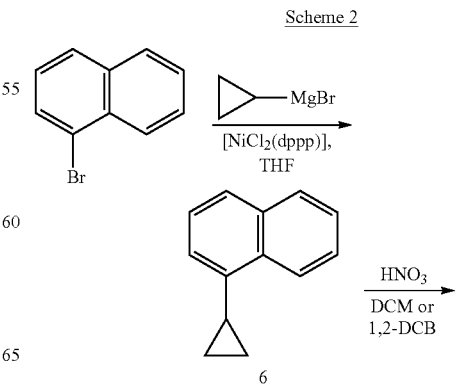

-continued

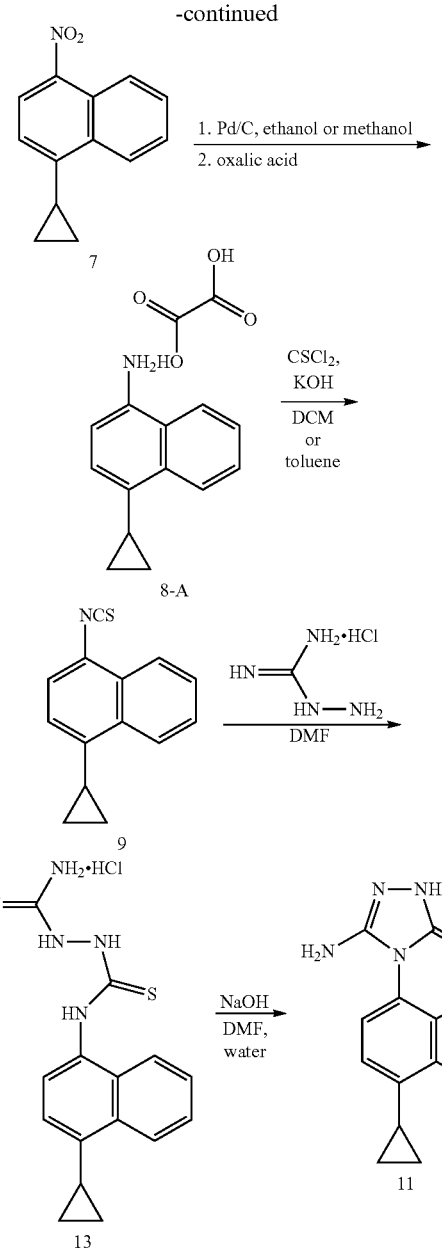

Starting with 1-bromonaphthalene, a reaction with a suitable Grignard reagent provides Compound 6.

Compound 11 is then prepared by a process (Process 6) comprising
(11-i) contacting Compound 7 with hydrogen, palladium on charcoal, in one or more suitable solvents to provide a compound of structure:

(Compound 8)

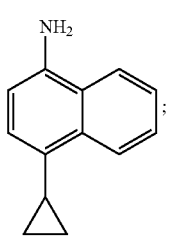

(11-ii) contacting Compound 8 with oxalic acid to provide an oxalate salt of Compound 8;
(11-iii) contacting the oxalate salt of Compound 8, of step (11-i), with a base, thiophosgene and a solvent and stirring the mixture at a temperature below room temperature to provide a compound of structure:

(Compound 9)

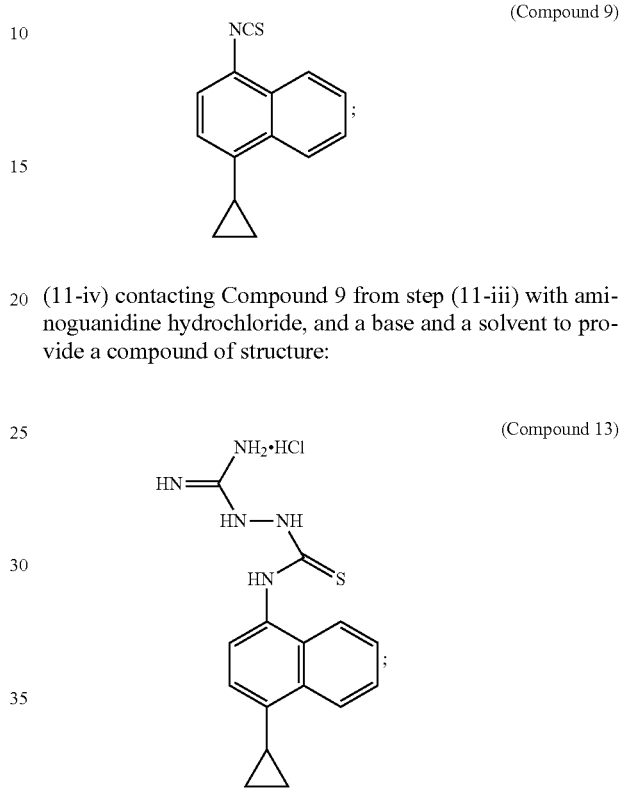

(11-iv) contacting Compound 9 from step (11-iii) with aminoguanidine hydrochloride, and a base and a solvent to provide a compound of structure:

(Compound 13)

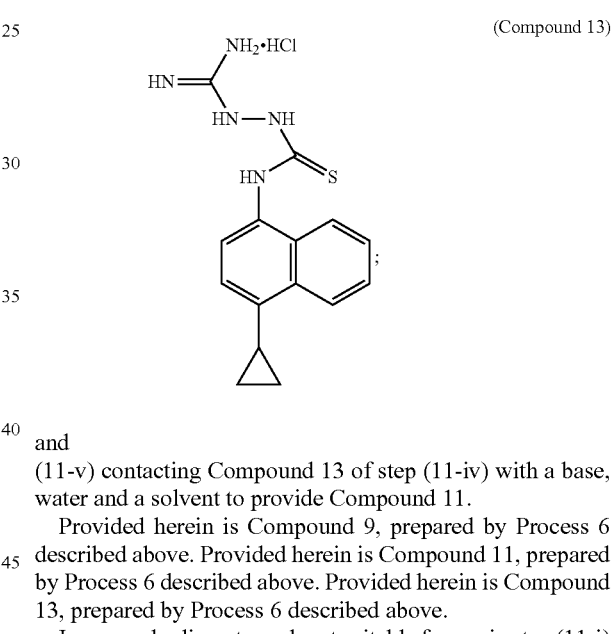

and
(11-v) contacting Compound 13 of step (11-iv) with a base, water and a solvent to provide Compound 11.

Provided herein is Compound 9, prepared by Process 6 described above. Provided herein is Compound 11, prepared by Process 6 described above. Provided herein is Compound 13, prepared by Process 6 described above.

In one embodiment, a solvent suitable for use in step (11-i) of Process 6 described above is methanol, ethanol, or dichlorobenzene, or any combination thereof. In one embodiment, a solvent suitable for use in step (11-i) of Process 6 is methanol. In another embodiment, a solvent suitable for use in step (11-i) of Process 6 is ethanol. Alternate solvents such as, for example, THF are also contemplated within the scope of embodiments presented herein.

Contemplated within the scope of embodiments presented herein is the use of other acids and/or acid salts in step (11-ii) and (11-iii) of Process 6 described above, including and not limited to the use of citric acid, tartaric acid, acetic acid, hydrochloric acid and the like for preparation of corresponding acid salts of Compound 8.

In one embodiment, a solvent suitable for use in step (11-iii) of Process 6 is toluene. In alternate embodiments, a solvent suitable for use in step (11-iii) of Process 6 is dichlorobenzene, dichloromethane, xylenes, or any other suitable solvent. In some cases the reaction mixture of step (11-iii) of Process 6 is stirred at a temperature of between about 0° C.

and about 10° C., between about 5° C. and about 15° C., or between about 5° C. and about 25° C. In some cases, the reaction mixture of step (11-iii) of Process 6 is stirred at about 5° C. In some cases, the reaction mixture of step (11-iii) of Process 6 is stirred at about room temperature.

In further embodiments, a base suitable for the reaction in step (11-iii) of Process 6 is selected from potassium hydroxide, sodium hydroxide, lithium hydroxide, potassium carbonate, cesium carbonate, potassium phosphate or any other suitable base. In some embodiments, a base suitable for the reaction in step (11-iii) of Process 6 is potassium hydroxide.

In further embodiments, a base suitable for the reaction in step (11-iv) of Process 6 is an organic or an inorganic base. Non limiting examples include triethylamine, diisopropyl amine, diisopropylethyl amine, potassium hydroxide, sodium hydroxide, lithium hydroxide, potassium carbonate, cesium carbonate, potassium phosphate or any other suitable base. In one embodiment, the reaction of step (11-iv) of Process 6 described above is carried out in the presence of diisopropylethyl amine (DIEA) or sodium hydroxide. Any suitable solvent is selected for the reaction in step (11-iv) of Process 6 including, for example, DMF, THF, acetonitrile, dioxane, NMP or the like. In one embodiment, the reaction in step (11-iv) of Process 6 is carried out in DMF.

In one embodiment, a solvent suitable for use in step (11-v) of Process 6 is DMF. In alternate embodiments, a solvent suitable for use in step (11-v) of Process 6 is toluene, dichlorobenzene, xylenes, NMP, acetonitrile, dioxane, or any other suitable solvent. In further embodiments, a base suitable for the reaction in step (11-v) of Process 6 is selected from potassium hydroxide, sodium hydroxide, lithium hydroxide, potassium carbonate, cesium carbonate, potassium phosphate or any other suitable base. In some embodiments, a base suitable for the reaction in step (11-v) of Process 6 is sodium hydroxide.

Synthesis of Compound 11—Second Method

In a different exemplary embodiment, the synthesis of Compound 11, described in Scheme 1, was achieved using the sequence of reactions described in Scheme 3.

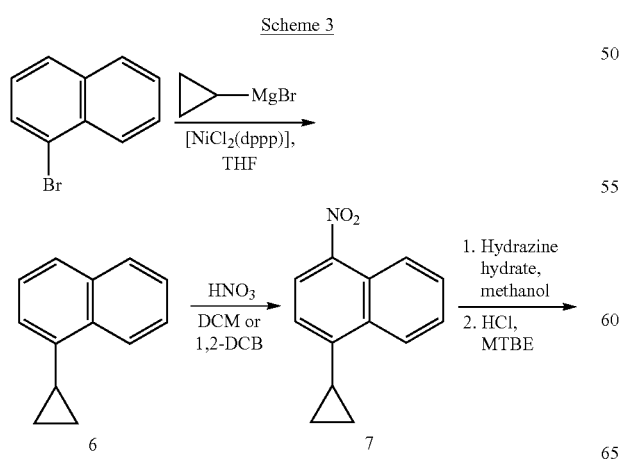

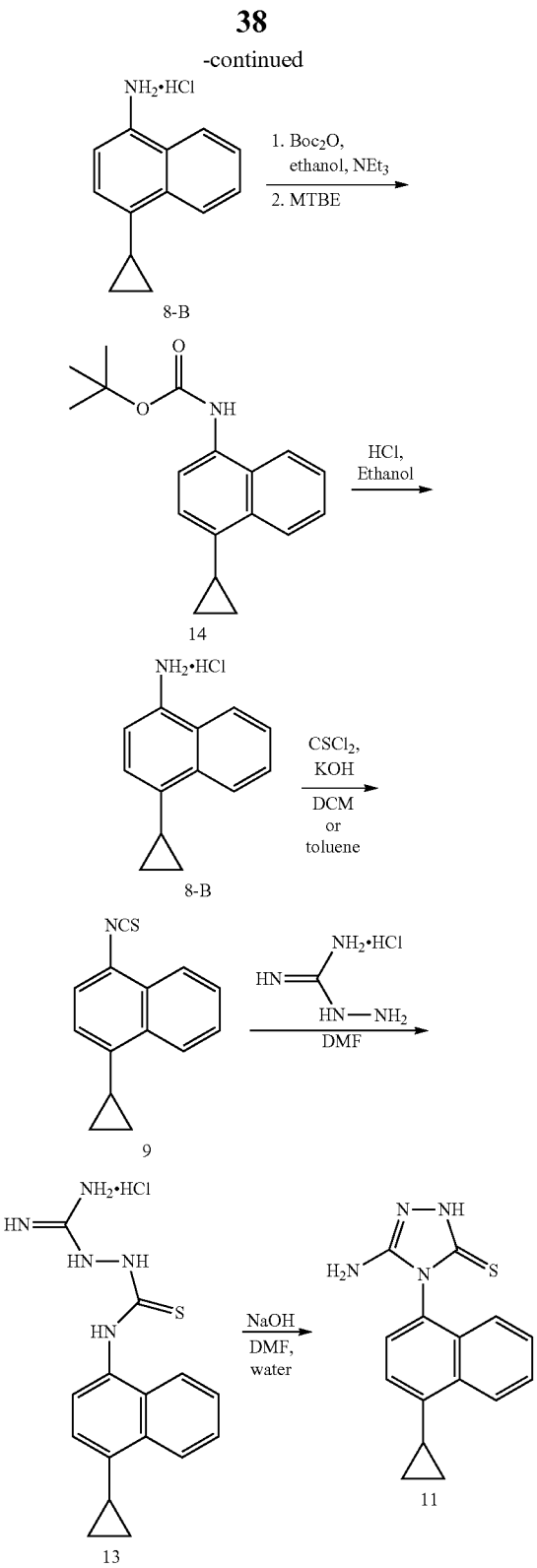

Starting with 1-bromonaphthalene, a reaction with a suitable Grignard reagent provides Compound 6.

Compound 11 is then prepared by a process (Process 7) comprising (11-i-A) contacting Compound 7 with hydrazine hydrate and a solvent to provide a compound of structure:

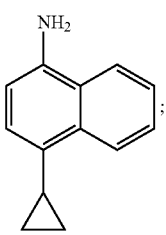
(Compound 8)

(11-ii-A) contacting Compound 8 with hydrochloric acid and a solvent to provide a hydrochloride salt of Compound 8;
(11-iii-A) protecting the amine group in the salt of step (11-ii-A) with to provide a compound of structure:

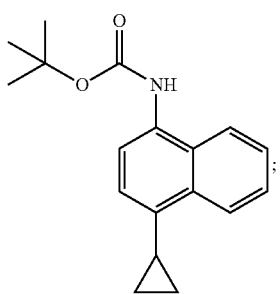
(Compound 14)

(11-iv-A) contacting Compound 14 with hydrochloric acid and ethanol to provide a hydrochloride salt of Compound 8;
(11-v-A) contacting the hydrochloride salt of Compound 8 from step (11-iv-A) with a base, thiophosgene and a solvent to provide a compound of structure:

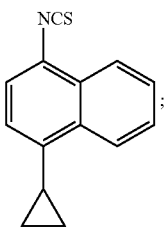
(Compound 9)

(11-vi-A) contacting Compound 9 from step (11-v-A) with aminoguanidine hydrochloride, a base, and a solvent to provide a compound of structure:

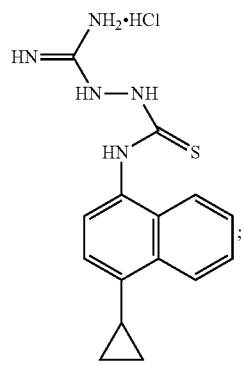
(Compound 13)

and
(11-vii-A) contacting Compound 13 from step (11-vi-A) with a base, water and a solvent to provide Compound 11.

Provided herein is Compound 9, prepared by Process 7 described above. Provided herein is Compound 11, prepared by Process 7 described above. Provided herein is Compound 13, prepared by Process 7 described above. Provided herein is Compound 14, prepared by Process 7 described above.

Provided herein is a Hydrogen chloride salt of Compound 8, obtainable by Process 7 described above and having the structure:

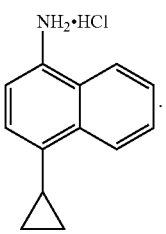
(Compound 8-B)

In one embodiment, a solvent suitable for use in step (11-i-A) of Process 7 described above is methanol, ethanol, or dichlorobenzene, or any combination thereof. In one embodiment, a solvent suitable for use in step (11-i-A) of Process 7 is methanol. In another embodiment, a solvent suitable for use in step (11-i-A) of Process 7 is ethanol. Alternate solvents such as, for example, THF are also contemplated within the scope of embodiments presented herein.

Contemplated within the scope of embodiments presented herein is the use of other acids and/or acid salts in step (11-ii-A), (11-iii-A) and (11-v-A) of Process 7 described above, including and not limited to the use of citric acid, tartaric acid, acetic acid, hydrochloric acid and the like for preparation of corresponding acid salts of Compound 8. Contemplated within the scope of embodiments presented herein is the use of a suitable solvent in step (11-ii-A) of Process 7 including THF, dioxane, diethyl ether, methy tert butyl ether (MTBE) or the like. In one embodiment, a solvent used in step (11-ii-A) of Process 7 is MTBE.

In one embodiment, a protecting group used in step (11-iii-A) of Process 7 is tert butyloxy carbonyl. Any other suitable amine protecting group may be used. In one embodiment, the reaction in step (11-iii-A) of Process 7 is carried out in the presence of Butyloxycarbonyl anhydride, ethanol, triethyl amine, and MTBE to provide Compound 14.

In one embodiment, a solvent suitable for use in step (11-v-A) of Process 7 is dichloromethane. In alternate embodiments, a solvent suitable for use in step (11-v-A) of Process 7 is toluene, dichlorobenzene, xylenes, or any other suitable solvent. In some cases the reaction mixture of step (11-v-A) of Process 7 is stirred at a temperature of between about 0° C. and about 10° C., between about 5° C. and about 15° C., or between about 5° C. and about 25° C. In some cases, the reaction mixture of step (11-v-A) of Process 7 is stirred at about 5° C. In some cases, the reaction mixture of step (11-v-A) of Process 7 is stirred at about room temperature.

In further embodiments, a base suitable for the reaction in step (11-v-A) of Process 7 is selected from potassium hydroxide, sodium hydroxide, lithium hydroxide, potassium carbonate, cesium carbonate, potassium phosphate or any other suitable base. In some embodiments, a base suitable for the reaction in step (11-v-A) of Process 7 is potassium hydroxide.

In further embodiments, a base suitable for the reaction in step (11-vi-A) of Process 7 is an organic or an inorganic base.

Non limiting examples include triethylamine, diisopropyl amine, diisopropylethyl amine, potassium hydroxide, sodium hydroxide, lithium hydroxide, potassium carbonate, cesium carbonate, potassium phosphate or any other suitable base. In one embodiment, the reaction of step (11-vi-A) of Process 7 described above is carried out in the presence of diisopropylethyl amine (DIEA) or sodium hydroxide. Any suitable solvent is selected for the reaction in step (11-vi-A) of Process 7 including, for example, DMF, THF, acetonitrile, dioxane, NMP or the like. In one embodiment, the reaction in step (11-vi-A) of Process 7 is carried out in DMF.

In one embodiment, a solvent suitable for use in step (11-vii-A) of Process 7 is DMF. In alternate embodiments, a solvent suitable for use in step (11-vii-A) of Process 7 is toluene, dichlorobenzene, xylenes, NMP, acetonitrile, dioxane, or any other suitable solvent. In further embodiments, a base suitable for the reaction in step (11-vii-A) of Process 7 is selected from potassium hydroxide, sodium hydroxide, lithium hydroxide, potassium carbonate, cesium carbonate, potassium phosphate or any other suitable base. In some embodiments, a base suitable for the reaction in step (11-vii-A) of Process 7 is sodium hydroxide.

Drawbacks in Initial Attempts

The sequence of reactions described in Scheme 1 requires the use of copper (II) bromide which generates waste material and requires additional expense for disposal of the waste. An additional drawback of this procedure is that Compound 1 is isolated twice to achieve the desired levels of purity.

Further, the synthesis of Compound 11 requires a lengthy sequence of steps as described in Scheme 2 and Scheme 3 above, and the use of aminoguanidine hydrochloride. The removal of Compound 13 also requires additional purification steps. In addition, as shown in Scheme 3, Compound 8-B is isolated twice in order to achieve the desired levels of purity for Compound 11.

Improved Processes

In order to avoid the drawbacks of the procedures described above and in Schemes 1-3, alternate procedures for the synthesis of compound of Formula (I), including Compound 1 and Compound 4, were investigated. The improved procedures described below have certain advantages. The improved procedures reduce the number of steps required for the manufacture of compounds of Formula (I), including Compound 1 or Compound 4. The improved processes allow for easier purification of the target compounds and do not require duplicative isolations of the same compound. The improved processes avoid the use of aminoguanidine hydrochloride and the consequent additional purification steps required for removal of Compound 13. Further, the improved processes described below avoid the use of corrosive chemicals and reduce waste such as the waste from the copper bromide reaction described in Scheme 1 above.

Accordingly, certain new processes for the synthesis of compounds of Formula (I), including Compound 1 and Compound 4, were designed as described below and in the summary of the invention section. The improvement in the new processes is the use of a compound of Formula (II) as an intermediate for the synthesis of compounds of Formula (I). An additional improvement in the new process is the use of formyl hydrazine, instead of aminoguanidine, for the synthesis of a triazole. The employment of formyl hydrazine avoids the formation of semicarbazides such as Compound 13 of the old process and reduces the purification steps required for removal of the intermediate semicarbazides such as Compound 13 of the old process.

Synthesis of Compounds of Formula (II)

In one embodiment, Scheme 4 below describes an exemplary synthesis of compounds of Formula (II).

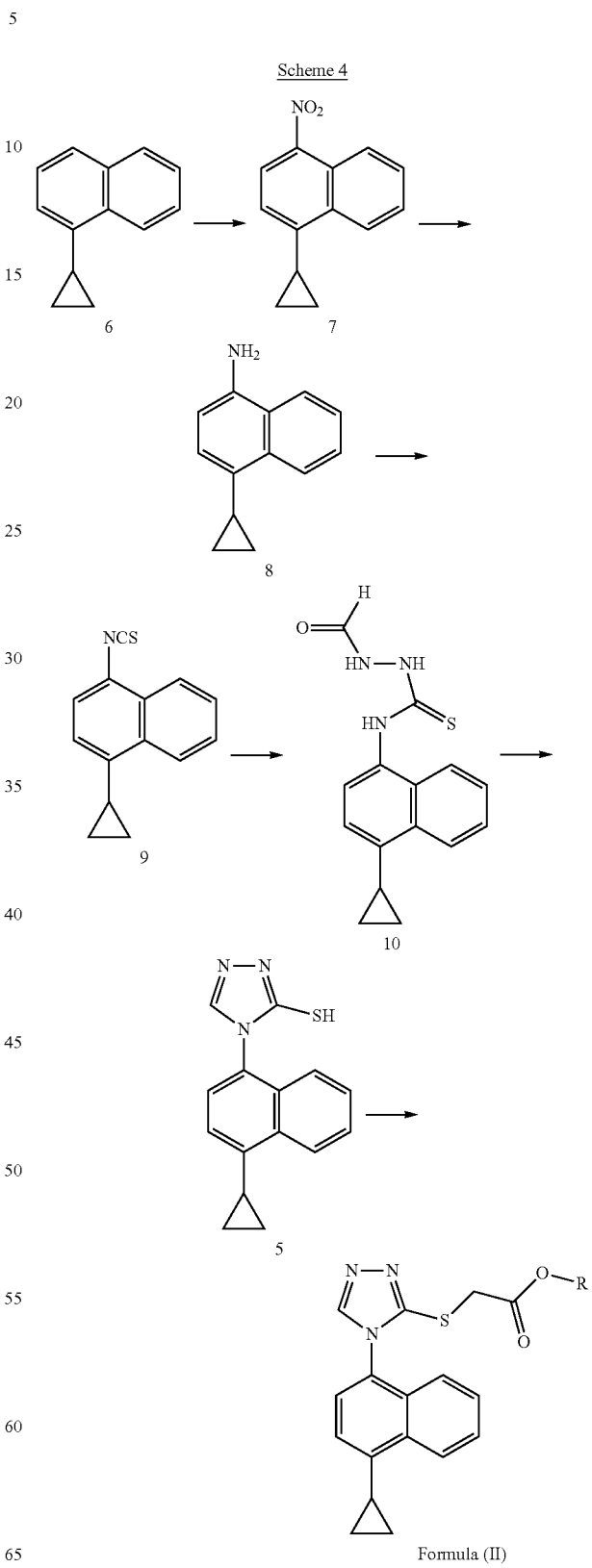

Provided herein in some embodiments is a process to synthesize compounds of formula (II). In some embodiments, Compound 6 is transformed to a compound of formula (II) (e.g., Compound 2). In some embodiments, Compound 6 is transformed to Compound 7. In some embodiments, Compound 7 is transformed to Compound 8. In further and additional embodiments, Compound 8 is transformed to Compound 9. In further and additional embodiments, Compound 9 is transformed to Compound 10. In further or additional embodiments, Compound 10 is transformed to Compound 5. In some embodiments, Compound 5 is transformed to a compound of formula (II).

In some embodiments, Compound 6 is transformed to Compound 7 in the presence of one or more nitrating agents. Non-limiting examples of suitable nitrating include $HNO_3$, $HNO_3$ with acid (e.g., $H_2SO_4$), $NH_4NO_3$/trifluoroacetic acid, isoamyl nitrate/$BF_3.Et_2O$, isoamyl nitrate/TfOH, $Cu(NO_3)$/TFAA, $AgNO_3/Tf_2O$, and $Hg(NO_3)_2/HNO_3$. Any suitable solvent is used for the nitration reaction. In some embodiments, a suitable solvent used for the reaction is halobenzene (e.g., 1,2-dichlorobenzene), toluene, water, ionic liquids, or combinations thereof.

In some embodiments, Compound 7 is reduced to provide Compound 8 in the presence of one or more reducing agents. In some embodiments, suitable reducing agents include palladium (e.g., palladium on carbon, 5% palladium on carbon, 10% palladium on carbon, palladium on barium sulfate, palladium chloride on carbon), platinum oxide, Raney nickel, iron metal in acetic acid (e.g., Fe/HCl in aqueous ethanol), $FeCl_3$/HCl, tin (II) chloride in acid, zinc metal, sodium dithionite, lithium aluminum hydride, diisobutylaluminum hydride, super hydride, samarium diiodide, samarium metal (e.g., Sm (4 equiv)/$NH_4Cl$ in methanol), sodium sulfide (e.g., sodium sulfide/$NH_4Cl$ in aqueous $NH_4OH$), hydrogen sulfide/base, titanium (III) chloride or any other suitable reduction method. Any suitable solvent may be used for the reduction. In some embodiments, the solvent is water, acetonitrile, DMF, THF, toluene, xylenes, dioxane, butanol, methanol, ethanol, diethyl ether, acetone, hexane, pentane, heptane, ethyl acetate, dichloromethane, dichloroethane, dichlorobenzene, NMP or combinations thereof.

In one embodiment, Compound 8 comprising an amino group, is optionally converted to an acid salt. Non-limiting examples of acids that are employable for synthesis of acid salts of Compound 8 include oxalic acid, tartaric acid, citric acid, formic acid, malonic acid, maleic acid, adipic acid, formic acid, chloroacetic acid, dichloroacetic acid, trichloroacetic acid, trifluoroacetic acid, benzoic acid, hydrochloric acid or any other suitable acid. In some embodiments, the free amine of Compound 8 is used in further steps.

In some embodiments, Compound 8 is transformed to Compound 9 in the presence of a thionyl transfer reagent. In some embodiments, the thionyl transfer reagent is thiophosgene. In some embodiments, Compound 8, or an acid salt thereof, is converted to a thioisocyanate in the presence of thiophosgene and a suitable base. In some embodiments, the base is potassium bicarbonate, potassium carbonate, potassium acetate, potassium hydroxide, sodium acetate, sodium benzoate, sodium bicarbonate, sodium carbonate, sodium hydroxide, sodium metasilicate, sodium sesquicarbonate, trisodium phosphate, calcium carbonate, calcium hydroxide, ferrous hydroxide, lithium hydroxide, barium hydroxide, cesium hydroxide, strontium hydroxide, rubidium hydroxide, cesium carbonate, potassium t-butoxide, or potassium phosphate. In certain embodiments, the base is butyl lithium, lithium diisopropylamide, lithium diethylamide, sodium amide, sodium hydride, sodium lithium bis(trimethylsilyl)amide, lithium bis(trimethylsilyl)amide. In other embodiments, the base is ammonia, triethylamine, propylamine, methylamine, dimethylamine, trimethylamine, methyldiethylamine, diisopropylethylamine, aniline, piperidine, pyridine, 1,8-diazabicyclo[5.4.0]undec-7-ene (DBU), or pyrrolidine. Any suitable solvent may be used for the nucleophilic addition transformation.

In some embodiments, the thionyl transfer reagent is carbon disulfide, sodium thiocyanate, thiocarbonyl diimidazole, potassium thiocyante, zinc thiocyanate, silver thiocyanate, or ammonium thiocyanate. In some instances, Compound 8, or a salt thereof, is converted to a thioisocyanate in the presence of carbon disulfide ($CS_2$). In further or additional embodiments, the reaction further comprises aqueous $NH_4OH$, followed by the addition of lead nitrate ($Pb(NO_3)_2$). In alternative embodiments, the reaction of Compound 8 or an acid salt thereof and $CS_2$ further comprises a base and a solvent (e.g., THF) followed by TsCl. In alternative embodiments, Compound 8, or an acid salt thereof (e.g., Compound 8-A), is converted to a thioisocyanate in the presence of thiocarbonyl diimidazole and a solvent (e.g., DMF). In other embodiments, Compound 8, or a salt thereof, is converted to a thioisocyanate in the presence of a thiocyanate (e.g., sodium thiocyanate). In certain embodiments, the reaction of Compound 8 with a thiocyanate (e.g., sodium thiocyanate) provides a thiourea intermediate. In further or additional embodiments, elimination of ammonia from the thiourea intermediate provides Compound 9. In certain embodiments, the thiourea intermediate is heated to high temperatures (e.g., 100° C., 110° C., 120° C., 130° C., 140° C., 150° C., 160° C., 170° C., 180° C., 190° C., or 200° C.) to provide Compound 9. In some embodiments, the solvent used for any transformation of Compound 8 to Compound 9 is acetonitrile, DMF, THF, toluene, xylenes, dioxane, butanol, methanol, ethanol, diethyl ether, acetone, hexane, pentane, heptane, ethyl acetate, dichloromethane, dichloroethane, dichlorobenzene, NMP or combinations thereof.

In some embodiments, Compound 9 is transformed to Compound 10 in the presence of nucleophile. In some embodiments, the nucleophile is formyl hydrazine. Any suitable solvent may be used for the nucleophilic addition transformation. In some embodiments, the solvent is water, acetonitrile, DMF, THF, toluene, xylenes, dioxane, butanol, methanol, ethanol, diethyl ether, acetone, hexane, pentane, heptane, ethyl acetate, dichloromethane, dichloroethane, dichlorobenzene, NMP or combinations thereof.

In some embodiments, Compound 10 is cyclized to provide Compound 5 in the presence of one or more bases. Any suitable base may be used in the cyclization reaction. In some embodiments, the base is potassium bicarbonate, potassium carbonate, potassium acetate, potassium hydroxide, sodium acetate, sodium benzoate, sodium bicarbonate, sodium carbonate, sodium hydroxide, sodium metasilicate, sodium sesquicarbonate, trisodium phosphate, calcium carbonate, calcium hydroxide, ferrous hydroxide, lithium hydroxide, barium hydroxide, cesium hydroxide, strontium hydroxide, rubidium hydroxide, cesium carbonate, potassium t-butoxide, or potassium phosphate. In certain embodiments, the base is butyl lithium, lithium diisopropylamide, lithium diethylamide, sodium amide, sodium hydride, sodium lithium bis(trimethylsilyl)amide, lithium bis(trimethylsilyl)amide. In other embodiments, the base is ammonia, triethylamine, propylamine, methylamine, dimethylamine, trimethylamine, methyldiethylamine, diisopropylethylamine, aniline, piperidine, pyridine, 1,8-diazabicyclo[5.4.0]undec-7-ene (DBU), or pyrrolidine. Any suitable solvent may be used for the nucleophilic addition transformation. In some embodiments, the solvent is water, acetonitrile, DMF, THF, toluene, xylenes, dioxane, butanol, methanol, ethanol, diethyl ether, acetone, hexane, pentane, heptane, ethyl acetate, dichloromethane, dichloroethane, dichlorobenzene, NMP or combinations thereof.

In some embodiments, Compound 5 undergoes a nucleophilic substitution to provide a compound of formula (II) in the presence of an electrophile. In some embodiments, the electrophile has the structure

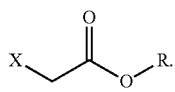

In some embodiments, X is a leaving group. In certain embodiments, X is halo (e.g., bromo, iodo, or chloro), tosylate, mesylate, besylate, triflate, nonaflates, fluorosulfonates, or OH. In some embodiments, R is alkyl. In other embodiments, R is $C_{1-20}$ alkyl, $C_{1-10}$ alkyl, $C_{1-6}$ alkyl, or $C_{1-3}$ alkyl. In some embodiments, R is methyl, ethyl, propyl, isopropyl, butyl, isobutyl, tert-butyl, isoamyl, pentyl, hexyl, heptyl, octyl, nonyl, terpenyl, bornyl, allyl, linalyl, and/or geranyl ethers. In some embodiments, R is H. Any suitable solvent may be used for the nucleophilic substitution transformation. In some embodiments, the solvent is water, acetonitrile, DMF, THF, toluene, xylenes, dioxane, butanol, methanol, ethanol, diethyl ether, acetone, hexane, pentane, heptane, ethyl acetate, dichloromethane, dichloroethane, dichlorobenzene, NMP or combinations thereof.

In some embodiments of the process discussed above (Scheme 4), the Compounds or intermediates are isolated and used in subsequent synthetic steps without any further purification steps. In certain embodiments, the Compounds or intermediates (e.g., Compound 7, 8, 9, 10, 5, or a compound of formula II) are used without intermediate isolation or purification steps. In some embodiments, the Compounds or intermediates are purified before used in further synthetic steps. In certain embodiments, the Compounds or intermediates are purified by crystallization. In some embodiments, the Compounds or intermediates are purified by distillation, column chromatography, reverse phase chromatography, preparative thin layer chromatography, or combinations thereof.

In a further embodiment, Scheme 5 below describes an alternate exemplary synthesis of compounds of Formula (II).

Scheme 5

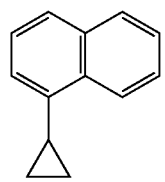

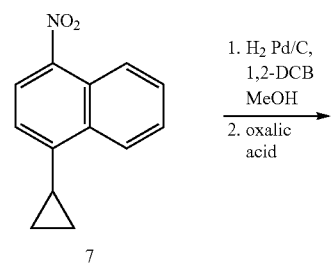

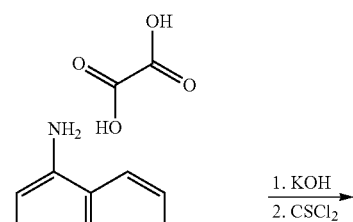

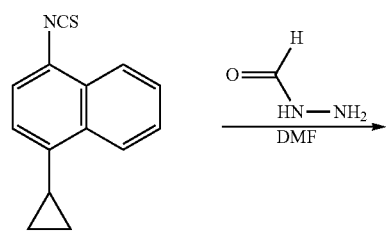

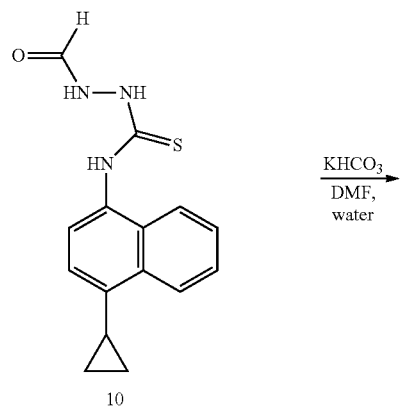

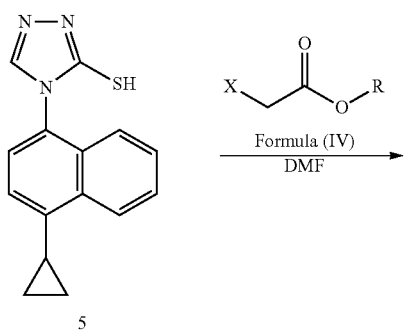

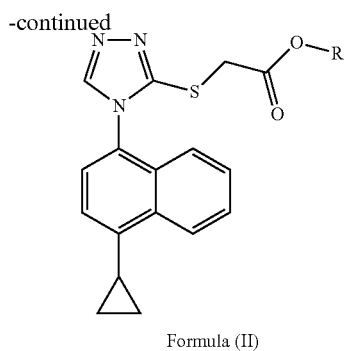

Formula (II)

Referring to Scheme 5 described above, starting with Compound 6, a nitration reaction provides Compound 7. The nitro group in Compound 7 is reduced to an amine (Compound 8) using any suitable reduction method. In one embodiment, the reduction is carried out using hydrogen gas and palladium on charcoal, in the presence of a suitable solvent. In some embodiments, a catalytic amount of palladium is used (e.g., 0.001%, 0.005%, 0.01%, 0.02%, 0.05%, 0.1%, 0.2%, 0.5%, 1%, 2%, 3%, 4%, 5% or 10%). In some embodiments, a stoichiometric amount of palladium on charcoal is used. In one embodiment, a solvent suitable for the catalytic hydrogenation is selected from methanol, ethanol, tert-butanol, THF, dichlorobenzene, or any combination thereof.

In one embodiment, Compound 8 comprising an amino group, is converted to an acid salt (e.g., oxalate salt). In one embodiment, an acid salt of the amine (Compound 8) is used in further steps (e.g., as shown in Scheme 5).

In one embodiment, as shown in Scheme 5, Compound 8, or an acid salt thereof (e.g., Compound 8-A) is converted to a thioisocyanate (Compound 9) in the presence of thiophosgene and a suitable base. In some of such embodiments, a solvent suitable for the synthesis of Compound 9 from Compound 8, or a salt thereof, is toluene. In alternate embodiments, a solvent suitable for the synthesis of Compound 9 from Compound 8, or a salt thereof, according to Scheme 4, is dichlorobenzene, xylenes, dichloromethane, or any other suitable solvent. In some cases the reaction mixture is stirred at a temperature of between about 0° C. and about 10° C., between about 5° C. and about 15° C., or between about 5° C. and about 25° C. In some cases, the reaction mixture is stirred between about 5 to about 100° C. In some cases, the reaction mixture is stirred at about 5° C. In some cases, the reaction mixture is stirred at about room temperature. In further embodiments, a base suitable for the synthesis of Compound 9 from Compound 8, or a salt thereof, is selected from potassium hydroxide, sodium hydroxide, lithium hydroxide, potassium carbonate, cesium carbonate, potassium phosphate or any other suitable base. In some embodiments, a base suitable for the synthesis of Compound 9 from Compound 8, or a salt thereof, is potassium hydroxide.

In an alternate embodiment, the free base of Compound 8 is converted to the thioisocyanate Compound 9 in the presence of sodium thiocyanate and water. In one embodiment, the solvent employed for the reaction is butanol, ethanol, water, acetonitrile, dioxane, toluene, xylenes, DCB, DMF, NMP or any other suitable solvent. In one embodiment, the reaction mixture is stirred at a temperature of at least 100° C., 110° C., 120° C., 130° C., 140° C. or 150° C. In some specific embodiments, the reaction of the free base of Compound 8 with sodium thiocyanate is carried out in the presence of water and xylenes at a temperature of at least 130° C. Also contemplated within the scope of embodiments presented herein is the use of other thiocyantes such as potassium thiocyante, zinc thiocyanate, silver thiocyante, ammonium thiocyanate, or other suitable reagents.

The thioisocyanate Compound 9 is converted to Compound 10 in the presence of formyl hydrazine and a suitable solvent. In one embodiment, the solvent is DMF. In alternate embodiments, the solvent is acetonitrile, THF, dioxane, dichloromethane, dichlorobenzene, NMP or any other suitable solvent. Advantageously, this step avoids the formation of Compound 13 as described above in Scheme 2 and Scheme 3.

Compound 10 is cyclized to Compound 5 using a suitable base, water and a solvent. In one embodiment, the base is potassium bicarbonate. In alternate embodiments, the base is selected from potassium hydroxide, sodium hydroxide, sodium bicarbonate, lithium hydroxide, potassium carbonate, cesium carbonate, potassium phosphate or any other suitable base. In one embodiment the solvent employed for the conversion of Compound 10 to Compound 5 is DMF. In other embodiments, the solvent employed for the conversion of Compound 10 to Compound 5 is THF, acetonitrile, DCM, DCB, ethanol, methanol, dioxane, NMP or any other suitable solvent.

Compound 5 is converted to a compound of Formula (II) in the presence of any suitable base and an acetate ester of Formula (IV) comprising a leaving group. In one embodiment, the reaction of Compound 5 with bromo methyl acetate

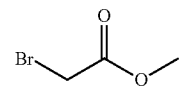

or chloro methyl acetate

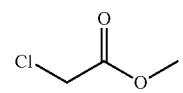

provides a compound of Formula (II) wherein R is methyl (Compound 2). In a different embodiment, the reaction of Compound 5 is carried out with bromo ethyl acetate

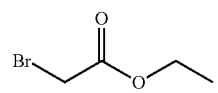

or chloroethyl acetate

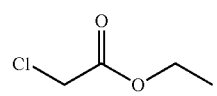

to provide a compound of Formula (II) wherein R is ethyl (Compound 2-A). Any suitable solvent is used. In one embodiment the solvent is DMF. In alternate embodiments, the solvent is dioxane, acetonitrile, chloroform, dichloromethane, tetrahydrofuran (THF), N-methyl pyrrolidone (NMP), dimethylsulfoxide (DMSO) and the like. In one embodiment, a compound of Formula (II) is isolated as a wet cake which is optionally washed with cooled ethyl acetate and isopropanol and/or a combination thereof.

Synthesis of Compounds of Formula (I) from Compounds of Formula (II)

Scheme 6a describes an exemplary synthesis of compounds of Formula (I).

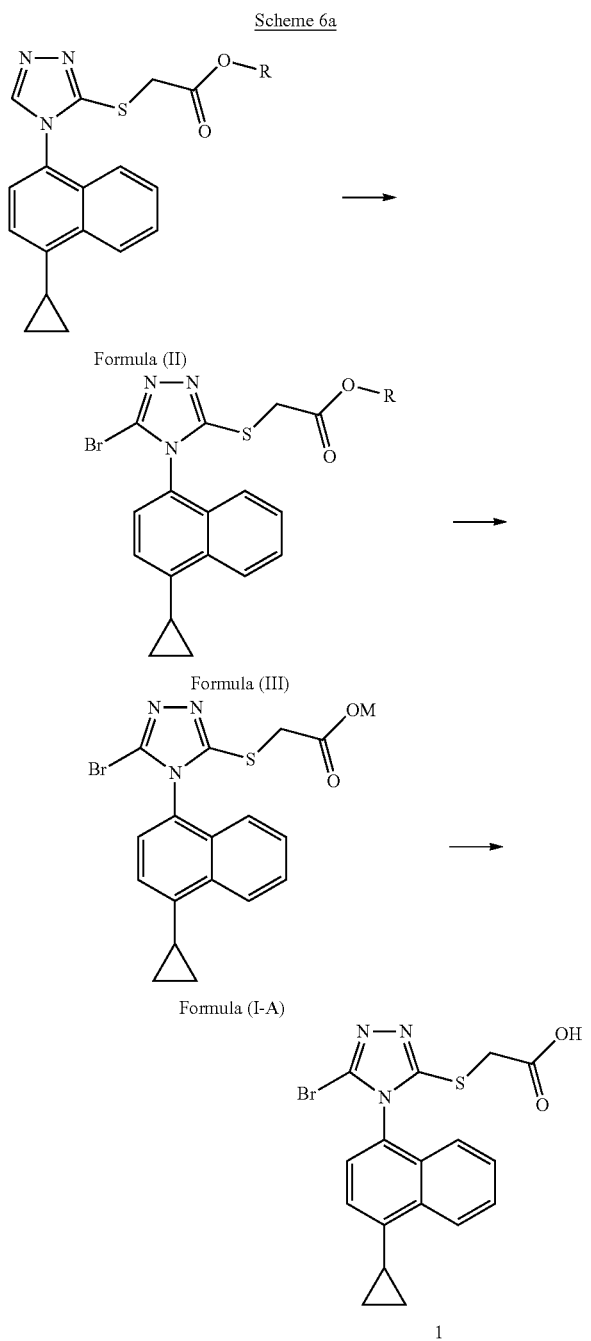

Provided herein in some embodiments is a process to synthesize Compound 1. The synthesis of compounds of formula (II) has been described above (e.g., Schemes 1, 4, and 5). In some embodiments, a compound of formula (II) is transformed to Compound 1. In some embodiments, a compound of formula (II) is transformed to a compound of formula (III). In some embodiments, a compound of formula (III) is transformed to a compound of formula (I-A). In further or additional embodiments, a compound of formula (I-A) is transformed into Compound 1.

In some embodiments, a compound of formula (II) is brominated in the presence of a brominating agent to provide a compound of formula (III). In some embodiments, bromination of a compound of formula (II) wherein R=H provides Compound 1. In certain embodiments, the brominating agent is N-bromosuccinimide (NBS), $Br_2$, $BrCl/Br_2$, tetrabutylammoniumtribromide, ammonium bromide/oxone (in methanol and/or water), selenium dibromide, $FeBr_3/Br_2$, $AlCl_3/Br_2$, $FeCl_3/Br_2$, $ZnCl_2/Br_2$, 1,2-dipyridiniumtribromide-ethane, NBS/acid (trifluoromethanesulfonic acid and $BF_3$—$H_2O$), NBS/concentrated sulfuric acid, NBS/tetrabutylammonium bromide, LiBr/PhI/m-chloroperbenzoic acid/TsOH, $AuCl_3$/NBS, $NBS/Pd(OAc)_2$, N,N,N',N'-tetrabromobenzene-1,3-disulfonylamide/poly[N-bromobenzene-1,3-disulfonylamide], $LiTMP/ZnCl_2/Br_2$, $[Ir(COD)(OMe)]_2/B_2pin_2/dtbpy/CuBr_2$ or $[Ir(COD)(OMe)]_2/B_2pin_2/dtbpy/CuCl_2$. Any suitable solvent may be used for the bromination. In some embodiments, the solvent is water, acetonitrile, DMF, THF, toluene, xylenes, dioxane, butanol, methanol, ethanol, diethyl ether, acetone, hexane, pentane, heptane, ethyl acetate, dichloromethane, dichloroethane, dichlorobenzene, NMP or combinations thereof.

In some embodiments, a compound of formula (III) is optionally hydrolyzed in the presence of a base to provide a compound of formula (I-A) wherein M is a cation. In certain embodiments, M is selected from $Na^+$, $Li^+$, $K^+$, $Cs^+$, $Ba^+$, $Ca^+$ or any other suitable cation. In some embodiments, the base is sodium hydroxide, lithium hydroxide, potassium hydroxide, cesium hydroxide, barium hydroxide, ferrous hydroxide, calcium hydroxide, ammonia, or any other suitable base. In certain embodiments, the base is potassium bicarbonate, potassium carbonate, potassium acetate, potassium hydroxide, sodium acetate, sodium benzoate, sodium bicarbonate, sodium carbonate, sodium hydroxide, sodium metasilicate, sodium sesquicarbonate, trisodium phosphate, calcium carbonate, calcium hydroxide, cesium carbonate, or potassium phosphate. Any suitable solvent may be used for the bromination. In some embodiments, the solvent is water, acetonitrile, DMF, THF, toluene, xylenes, dioxane, butanol, methanol, ethanol, diethyl ether, acetone, hexane, pentane, heptane, ethyl acetate, dichloromethane, dichloroethane, dichlorobenzene, NMP or combinations thereof. In some embodiments, the solvent is water.

In some embodiments, a compound of formula (I-A) is optionally treated with an acid to provide Compound 1. In some embodiments, the acid is hydrobromic acid, sulfuric acid, hydrochloric acid, hydroiodic acid, nitric acid, phosphoric acid, fluoroantimonic acid, fluoroboric acid, hexafluorophosphoric acid, trifluoroacetic acid, acetic acid, methanesulfonic acid, ethanesulfonic acid, benzenesulfonic acid, p-toluenesulfonic acid, trifluoromethanesulfonic acid, citric acid, formic acid, gluconic acid, lactic acid, oxalic acid, maleic acid, malonic acid, tartaric acid, or any suitable acid. Any suitable solvent may be used for providing the free acid Compound 1. In some embodiments, the solvent is water, acetonitrile, DMF, THF, toluene, xylenes, dioxane, butanol, methanol, ethanol, diethyl ether, acetone, hexane, pentane, heptane, ethyl acetate, dichloromethane, dichloroethane, dichlorobenzene, NMP or combinations thereof. In some embodiments, the solvent is ethyl acetate and heptane.

In some embodiments of the process discussed above (Scheme 6a), the compounds (e.g., compounds of formula (III), (I-A) and Compound 1) are isolated and used in subsequent synthetic steps without any further purification steps. In certain embodiments, the compounds (e.g., compounds of formula (III), (I-A) and Compound 1) are used without intermediate isolation or purification steps. In some embodiments, the compounds (e.g., compounds of formula (III), (I-A) and Compound 1) are purified before used in further synthetic steps. In certain embodiments, the compounds (e.g., compounds of formula (III), (I-A) and Compound 1) are purified by crystallization. In some embodiments, the compounds (e.g., compounds of formula (III), (I-A) and Compound 1) are purified by distillation, column chromatography, reverse phase chromatography, preparative thin layer chromatography, or combinations thereof.

Scheme 6b describes an exemplary synthesis of compounds of Formula (I), including Compound 1 and Compound 4.

Reaction of a compound of Formula (II) with N-bromosuccinimide (NBS) in a suitable solvent furnishes a compound of Formula (III). Solvents suitable for the NBS-mediated reaction include DMF, acetonitrile, MTBE or any other suitable solvent. The ester group in a compound of Formula (III) is optionally hydrolyzed to provide an acid salt of a compound of Formula (I), i.e., a compound of Formula (I-A) wherein M is selected from Na$^+$, Li$^+$, K$^+$, Cs$^+$ or any other suitable cation. The acid salt is optionally isolated and/or crystallized. The compound of Formula (I-A) is converted to Compound 1 in the presence of an acid. Compound 1 is optionally crystallized from a suitable solvent or mixture of solvents.

In a specific embodiment, Scheme 7 describes the synthesis of Compound 1 and Compound 4.

Scheme 6b

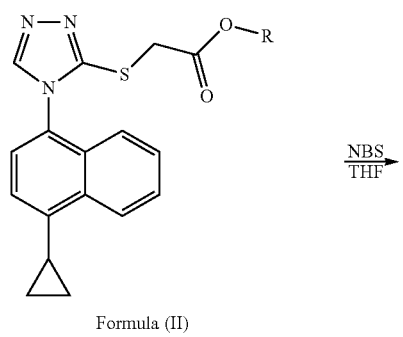

Formula (II)

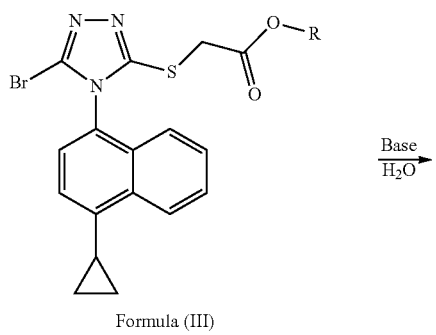

Formula (III)

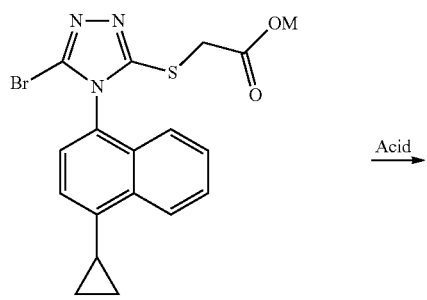

Formula (I-A)

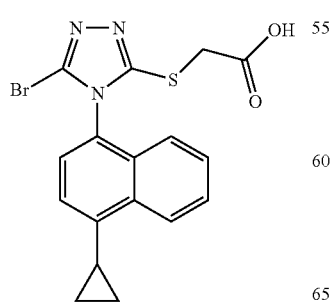

1

Scheme 7

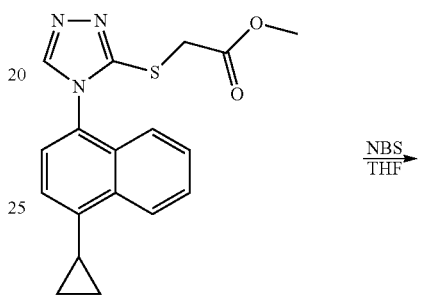

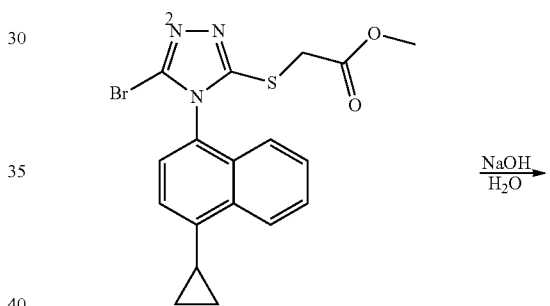

3

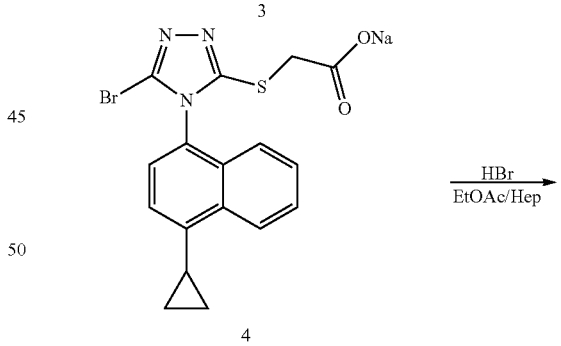

4

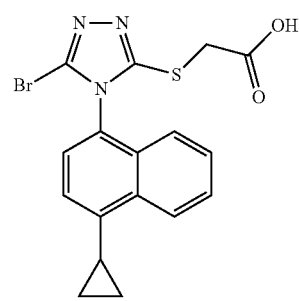

1

Accordingly, provided herein is a process (Process 8) for preparing Compound 1 having the following structure:

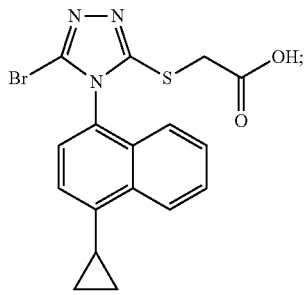

(Compound 1)

the improvement in the process being contacting a compound of structure

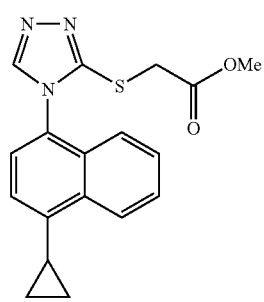

(Compound 2)

with a brominating agent (e.g., N-bromosuccinimide (NBS)) and a solvent.

In one embodiment, the solvent is THF. In alternate embodiments, the solvent is DMF, acetonitrile or any other suitable solvent.

In one instance, the NBS is added to a solution of Compound 2 in THF while the THF solution is maintained at a temperature of between about room temperature and about 32° C. In one embodiment, the reaction mixture is then stirred for at least 12 hours at a temperature of between about room temperature and about 32° C. In alternate embodiments, the reaction mixture is stirred for at least 2 hours, 4 hours, 6 hours, 8 hours, 10 hours, 12 hours, 14 hours, 20 hours, 24 hours or longer. In one case, if the content of Compound 2 in the reaction mixture assay is ≥1.5% area by High Performance Liquid Chromatography (HPLC), an additional quantity of NBS is added to the reaction mixture. In one embodiment, after stirring the reaction mixture for at least 12 hours, and/or optionally adding an additional quantity of NBS, the reaction mixture assay shows ≤1.5% area by HPLC of Compound 2. In another embodiment, after stirring the reaction mixture for at least 12 hours, and/or optionally adding an additional quantity of NBS, the reaction mixture assay shows ≤0.2% area by HPLC of Compound 2.

In one embodiment, a process for synthesis of Compound 1 further comprises
(1-i) extracting the reaction mixture with a solvent (e.g., toluene) while maintaining the mixture at a temperature of between about 2° C. and about 7° C.;
(1-ii) back-extracting the organic phase from step (1-i) with a sodium disulfite solution one or more times until NBS is undetectable in the aqueous phase by HPLC assay;
(1-iii) washing the organic phase from step (1-ii) with water,
(1-iv) washing the organic phase from step (1-iii) with a sodium bicarbonate solution one or more times until the aqueous phase has a pH of at least 8; and
(1-v) collecting the organic phase comprising a compound of structure:

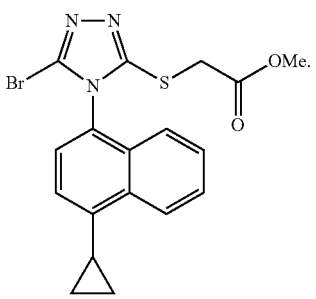

(Compound 3)

In one case, the process further comprises optionally concentrating the organic phase of step (1-v) under reduced pressure to obtain Compound 3.

In one case, the process further comprises the steps of
(1-vi) contacting the organic phase in step (1-v) of claim 7 with a solution of a base (e.g., sodium hydroxide) until the peak area of Compound 3 in the organic phase is lower than 50 mAU by HPLC assay; and
(1-vii) collecting the aqueous phase comprising a compound of structure:

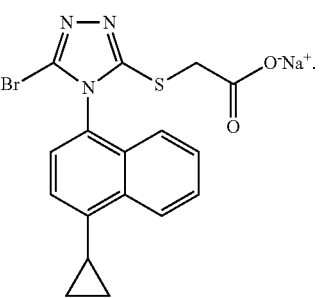

(Compound 4)

In one case the process further comprises the steps of
(1-viii) concentrating the aqueous phase in step (1-vii) of claim 8 under reduced pressure;
(1-ix) adding water to adjust the volume of the mixture in step (1-viii) to about 5.5±5% the calculated HPLC assay weight of Compound 1 in the aqueous phase of step (1-viii);
(1-x) cooling the mixture of step (1-ix) to obtain a suspension comprising crystalline Compound 4; and
(1-xi) filtering the suspension of step (1-x) to obtain a wet cake comprising crystalline Compound 4.

In one case, the process further comprises optionally drying the wet cake of step (1-xi) to obtain Compound 4.

In one case, the process further comprises the steps of
(1-xii) dissolving the wet cake comprising Compound 4 of step (1-xi) of claim 10 in water;
(1-xiii) adding a solvent (e.g. ethyl acetate) to the solution of step (1-xii);
(1-xiv) adding an acid (e.g., 24% hydrobromic acid) while maintaining the temperature of the reaction mixture below 35° C., and maintaining the pH of the reaction mixture between about 2.0 and about 4.0; and (1-xv) separating the organic phase comprising Compound 1.

In one case, the process further comprises (1-xvi) concentrating the organic phase of step (1-xv) of claim 10 under reduced pressure;

(1-xvii) stirring the mixture of step (1-xvi) between about 32° C. and about 38° C. for at least 8 hours;

(1-xviii) adding a co-solvent (e.g., n-heptane) to the mixture of step (1-xvii) and cooling the mixture; and (1-xix) filtering the suspension of step (1-xviii) to obtain Compound 1.

In one embodiment, step (1-xix) above yields crystalline Compound 1. Crystalline polymorphs of Compound 1 are described in PCT International Appl. No. PCT/US11/20233, and PCT International Appl. No. PCT/US11/67657 and the disclosure of polymorphs of Compound 1 and/or Compound 4 described in PCT International Appl. No. PCT/US11/20233, and PCT International Appl. No. PCT/US11/67657 is incorporated herein by reference.

In one aspect, provided herein is Compound 1, having no more than 0.1% of Compound 3 by area on an HPLC assay. In one embodiment, Compound 1 having no more than 0.1% of Compound 3 is obtained by the processes described above. In a further aspect, provided herein is Compound 1, having no more than 0.1% of Compound 2, and no more than 0.1% of Compound 3 by area on an HPLC assay. In yet another aspect, provided herein is Compound 1 having a purity of ≥98%. In a further aspect, provided herein is Compound 1 having a purity of ≥99%. In any of the aforementioned embodiments, the purity is determined by an HPLC assay. In any of the aforementioned embodiments, Compound 1 is prepared by Process 1, Process 2, Process 3, Process 4, Process 5, Process 6, Process 7, or Process 8, or any combination thereof.

Further Forms of Compounds of the Compounds Disclosed Herein

Isomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate, metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, Q-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of the invention and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, $N^+(C_{1-4}$ alkyl$)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization. The compounds described herein can be prepared as pharmaceutically acceptable salts formed when an acidic proton present in the parent compound either is replaced by a metal ion, for example an alkali metal ion, an alkaline earth ion, or an aluminum ion; or coordinates with an organic base. Base addition salts can also be prepared by reacting the free acid form of the compounds described herein with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like. In addition, the salt forms of the disclosed compounds can be prepared using salts of the starting materials or intermediates.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Polymorphs

In some embodiments, the compounds described herein exist as polymorphs. The invention provides for methods of treating diseases by administering such polymorphs. The invention further provides for methods of treating diseases by administering such polymorphs as pharmaceutical compositions.

Thus, the compounds described herein include all their crystalline forms, known as polymorphs. Polymorphs include the different crystal packing arrangements of the same elemental composition of a compound. In certain instances, polymorphs have different X-ray diffraction patterns, infrared spectra, melting points, density, hardness, crystal shape, optical and electrical properties, stability, and solubility. In certain instances, various factors such as the recrystallization solvent, rate of crystallization, and storage temperature cause a single crystal form to dominate.

Polymorph Form 1

In one embodiment, 2-(5-bromo-4-(4-cyclopropylnaphthalen-1-yl)-4H-1,2,4-triazol-3-ylthio)acetate polymorph Form 1 exhibits an x-ray powder diffraction pattern characterized by the diffraction pattern summarized in Table 1A or Table 1B. In some embodiments, provided herein is a polymorph of 2-(5-bromo-4-(4-cyclopropylnaphthalen-1-yl)-4H-1,2,4-triazol-3-ylthio)acetate comprising at least 3 peaks of (±0.1°2θ) of Table 1A or 1B. In certain embodiments, provided herein is a polymorph of 2-(5-bromo-4-(4-cyclopropylnaphthalen-1-yl)-4H-1,2,4-triazol-3-ylthio)acetate comprising at least 4 peaks of (±0.1°2θ) of Table 1A or 1B, at least 5 peaks of (±0.1°2θ) of Table 1A or 1B, at least 6 peaks of (±0.1°2θ) of Table 1A or 1B, at least 8 peaks of (±0.1°2θ) of Table 1A or 1B, at least 10 peaks of (±0.1°2θ) of Table 1A, at least 15 peaks of (±0.1°2θ) of Table 1A, at least 20 peaks of (±0.1°2θ) of Table 1A, at least 25 peaks of (±0.1°2θ) of Table 1A, or at least 30 peaks of (±0.1°2θ) of Table 1A.

TABLE 1A form 1

| °2θ | d space (Å) | Intensity (%) |
|---|---|---|
| 10.32 | 8.562 | 100 |
| 18.84 | 4.706 | 32.7 |
| 20.75 | 4.277 | 23.2 |
| 27.28 | 3.266 | 13.6 |
| 27.60 | 3.229 | 11 |
| 21.54 | 4.123 | 10.4 |
| 25.53 | 3.487 | 9.8 |
| 6.80 | 12.989 | 9.4 |
| 24.97 | 3.563 | 9.1 |
| 28.43 | 3.137 | 8.4 |
| 19.98 | 4.441 | 6.9 |
| 29.35 | 3.040 | 6.7 |
| 15.88 | 5.577 | 5.4 |
| 23.13 | 3.842 | 4.8 |
| 26.34 | 3.381 | 4.8 |
| 18.56 | 4.777 | 4.1 |

TABLE 1B form 1

| °2θ | d space (Å) | Intensity (%) |
|---|---|---|
| 10.32 | 8.562 | 100 |
| 18.84 | 4.706 | 32.7 |
| 20.75 | 4.277 | 23.2 |
| 27.28 | 3.266 | 13.6 |

In one embodiment provided herein, the polymorph form 1 of 2-(5-bromo-4-(4-cyclopropylnaphthalen-1-yl)-4H-1,2,4-triazol-3-ylthio)acetate is characterized by x-ray powder diffraction pattern peaks at 10.32, 18.84, and 20.75°2θ±0.1°2θ. In further embodiments, the polymorph form 1 is further characterized by at least one peak appearing at 6.80, 21.54, 24.97, 25.53, 27.28 and 27.60°2θ±0.1°2θ. In further embodiments, the polymorph form 1 is further characterized by at least two peaks appearing at 6.80, 21.54, 24.97, 25.53, 27.28 and 27.60°2θ±0.1°2θ. In yet still further embodiments, the polymorph exhibits an x-ray powder diffraction pattern substantially the same as the x-ray powder diffraction pattern shown in FIG. 1.

Polymorph Form 2

In one embodiment, 2-(5-bromo-4-(4-cyclopropylnaphthalen-1-yl)-4H-1,2,4-triazol-3-ylthio)acetate polymorph Form 2 exhibits an x-ray powder diffraction pattern characterized by the diffraction pattern summarized in Table 2A or Table 2B. In some embodiments, provided herein is a polymorph of 2-(5-bromo-4-(4-cyclopropylnaphthalen-1-yl)-4H-1,2,4-triazol-3-ylthio)acetate comprising at least 3 peaks of (±0.1°2θ) of Table 2A or 2B. In certain embodiments, provided herein is a polymorph of 2-(5-bromo-4-(4-cyclopropylnaphthalen-1-yl)-4H-1,2,4-triazol-3-ylthio)acetate comprising at least 4 peaks of (±0.1°2θ) of Table 2A or 2B, at least 5 peaks of (±0.1°2θ) of Table 2A or 2B, at least 6 peaks of (±0.1°2θ) of Table 2A or 2B, at least 8 peaks of (±0.1°2θ) of Table 2A or 2B, at least 10 peaks of (±0.1°2θ) of Table 2A, at least 15 peaks of (±0.1°2θ) of Table 2A, at least 20 peaks of (±0.1°2θ) of Table 2A, at least 25 peaks of (±0.1°2θ) of Table 2A, or at least 30 peaks of (±0.1°2θ) of Table 2A.

TABLE 2A form 2 Observed

| °2θ | d space (Å) | Intensity (%) |
|---|---|---|
| 7.97 | 11.086 | 13.8 |
| 9.66 | 9.148 | 26.1 |
| 10.46 | 8.449 | 83.8 |
| 11.96 | 7.394 | 41.3 |
| 12.55 | 7.046 | 16.7 |
| 12.94 | 6.836 | 15.7 |
| 13.82 | 6.402 | 41.6 |
| 16.19 | 5.471 | 49.8 |
| 18.21 | 4.867 | 74.0 |
| 18.76 | 4.727 | 81.4 |
| 19.02 | 4.662 | 35.6 |
| 19.51 | 4.548 | 15.9 |
| 19.83 | 4.474 | 100.0 |
| 20.40 | 4.349 | 13.4 |
| 21.36 | 4.157 | 12.3 |
| 22.50 | 3.948 | 36.7 |
| 22.88 | 3.884 | 30.6 |
| 23.08 | 3.850 | 56.1 |
| 24.01 | 3.704 | 42.1 |
| 25.15 | 3.539 | 35.2 |
| 25.46 | 3.496 | 20.5 |
| 26.06 | 3.417 | 13.4 |
| 26.51 | 3.360 | 35.7 |
| 27.97 | 3.187 | 26.8 |
| 29.93 | 2.983 | 37.0 |
| 30.42 | 2.936 | 12.4 |
| 31.77 | 2.814 | 17.1 |
| 32.35 | 2.765 | 38.2 |
| 34.26 | 2.615 | 12.8 |
| 38.01 | 2.366 | 16.5 |
| 38.88 | 2.314 | 10.0 |

TABLE 2B form 2 Representative

| °2θ | d space (Å) | Intensity (%) |
|---|---|---|
| 19.83 | 4.474 | 100.0 |
| 10.46 | 8.449 | 83.8 |
| 18.76 | 4.727 | 81.4 |
| 18.21 | 4.867 | 74.0 |
| 23.08 | 3.850 | 56.1 |

In one embodiment provided herein, the polymorph form 2 of 2-(5-bromo-4-(4-cyclopropylnaphthalen-1-yl)-4H-1,2,4-triazol-3-ylthio)acetate is characterized by x-ray powder diffraction pattern peaks at 10.46, 18.76, and 19.83°2θ±0.1°2θ. In further embodiments, the polymorph form 2 is further characterized by at least one peak appearing at 18.21, or 23.08°2θ±0.1°2θ. In further embodiments, the polymorph form 2 is further characterized by two peaks appearing at 18.21, or 23.08°2θ±0.1°2θ. In yet still further embodiments, the polymorph form 2 exhibits an x-ray powder diffraction pattern substantially the same as the x-ray powder diffraction pattern shown in FIG. 5.

In certain instances, the crystalline polymorphs of 2-(5-bromo-4-(4-cyclopropylnaphthalen-1-yl)-4H-1,2,4-triazol-3-ylthio)acetate were found to exhibit increased stability in comparison to the amorphous solid state form of the carboxylic acid. In some instances, improved stability of the crystalline polymorphs of 2-(5-bromo-4-(4-cyclopropylnaphthalen-1-yl)-4H-1,2,4-triazol-3-ylthio)acetate provides for the preparation of pharmaceutical dosage forms displaying reduced variability in the dosage present in a given dosage form, reduction in the presence of impurities in the final pharmaceutical product, and an improved shelf life of formulated dosage forms when compared to the pharmaceutical dosage form prepared with the amorphous solid state form of the carboxylic acid. In some embodiments, a polymorph described herein (e.g., Form 1 or Form 2) demonstrates no degradation (e.g., less than 0.01%, less than 0.1%, less than 0.5% by wt.) for at least 3 months under accelerated conditions (e.g., 40° C.-75% RH), for at least 4 months under accelerated conditions (e.g., 40° C.-75% RH), for at least 5 months under accelerated conditions (e.g., 40° C.-75% RH), for at least 6 months under accelerated conditions (e.g., 40° C.-75% RH), for at least 9 months under accelerated conditions (e.g., 40° C.-75% RH), for at least 12 months under accelerated conditions (e.g., 40° C.-75% RH), and/or (ii) for at least 12 months under long-term conditions (e.g., 25° C.-60% RH), for at least 18 months under long-term conditions (e.g., 25° C.-60% RH), for at least 24 months under long-term conditions (e.g., 25° C.-60% RH).

Figure 12:
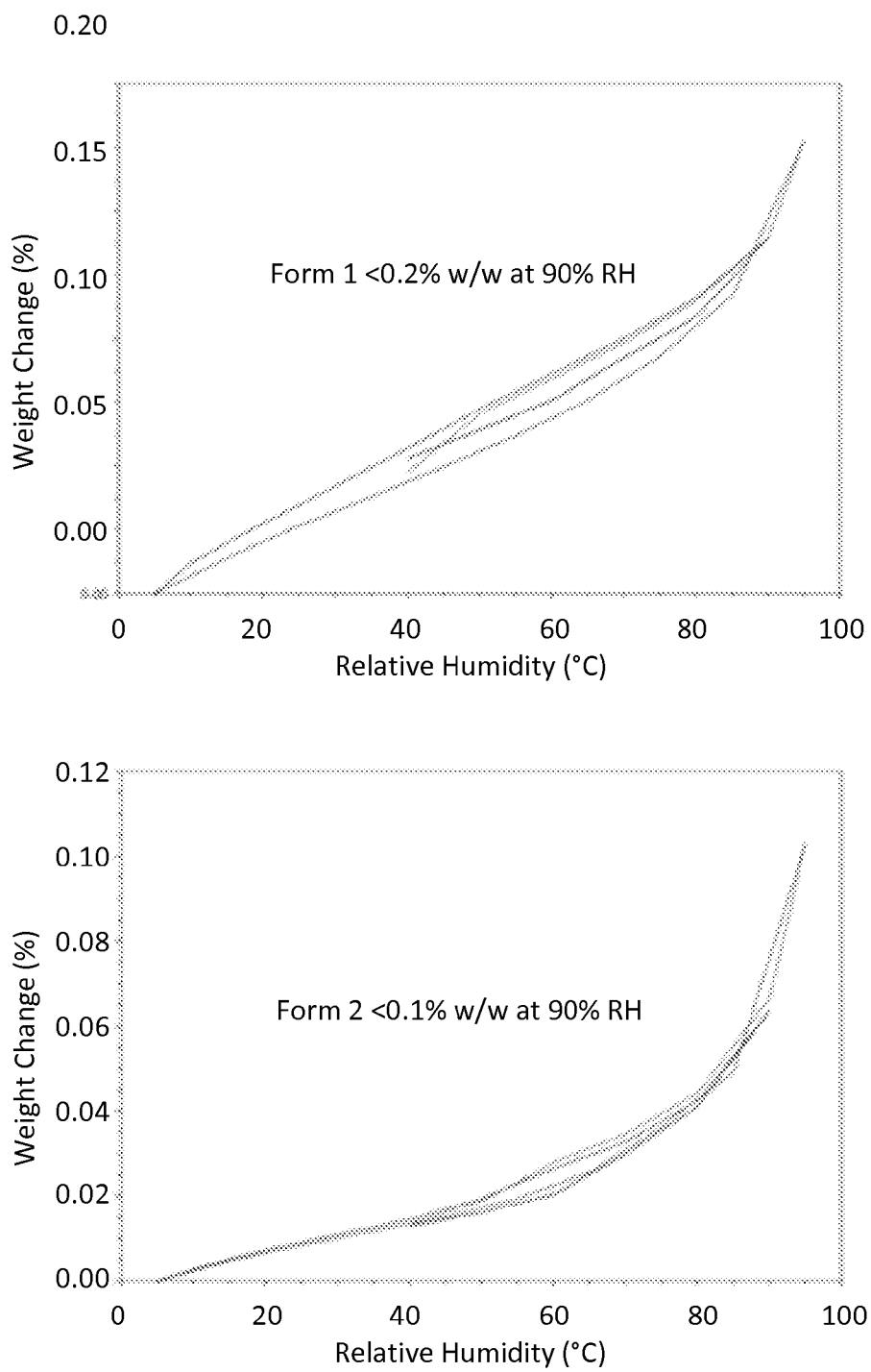
FIG. 12 represents an illustrative Gravimetric Vapor Sorption study of Polymorph form 1 and 2.

Additionally, in certain instances, the crystalline polymorphs of 2-(5-bromo-4-(4-cyclopropylnaphthalen-1-yl)-4H-1,2,4-triazol-3-ylthio)acetate were found to exhibit decreased hygroscopicity compared to other solid state forms as determined by gravimetric vapor sorption (GVS) studies. FIG. 12 illustrates a GVS study of form 1 and form 2. Form 1 was found to adsorb <0.2% w/w at high humidity and Form 2 was found to adsorb <0.1% w/w at high humidity. This property of decreased hygroscopicity greatly aids in the preparation of solid pharmaceutical dosage forms.

Polymorph Form A

In one embodiment, sodium 2-(5-bromo-4-(4-cyclopropylnaphthalen-1-yl)-4H-1,2,4-triazol-3-ylthio)acetate polymorph Form A exhibits an x-ray powder diffraction pattern characterized by the diffraction pattern summarized in Table 1A or Table 1B. In some embodiments, provided herein is a polymorph of sodium 2-(5-bromo-4-(4-cyclopropylnaphthalen-1-yl)-4H-1,2,4-triazol-3-ylthio)acetate comprising at least 3 peaks of (±0.1°2θ) of Table 1A or 1B. In certain embodiments, provided herein is a polymorph of sodium 2-(5-bromo-4-(4-cyclopropylnaphthalen-1-yl)-4H-1,2,4-triazol-3-ylthio)acetate comprising at least 4 peaks of (±0.1°2θ) of Table 1A or 1B, at least 5 peaks of (±0.1°2θ) of Table 1A or 1B, at least 6 peaks of (±0.1°2θ) of Table 1A or 1B, at least 8 peaks of (±0.1°2θ) of Table 1A or 1B, at least 10 peaks of (±0.1°2θ) of Table 1A, at least 15 peaks of (±0.1°2θ) of Table 1A, at least 20 peaks of (±0.1°2θ) of Table 1A, at least 25 peaks of (±0.1°2θ) of Table 1A, or at least 30 peaks of (±0.1°2θ) of Table 1A.

TABLE 1A

| °2θ | d space (Å) | Intensity (%) |
|---|---|---|
| 4.90 ± 0.10 | 18.027 ± 0.375 | 71 |
| 6.86 ± 0.10 | 12.891 ± 0.191 | 100 |
| 8.41 ± 0.10 | 10.512 ± 0.126 | 61 |
| 9.83 ± 0.10 | 8.996 ± 0.092 | 63 |
| 10.13 ± 0.10 | 8.730 ± 0.087 | 97 |
| 10.60 ± 0.10 | 8.346 ± 0.079 | 16 |
| 11.92 ± 0.10 | 7.424 ± 0.063 | 45 |
| 12.32 ± 0.10 | 7.183 ± 0.059 | 45 |
| 12.57 ± 0.10 | 7.041 ± 0.056 | 45 |
| 13.07 ± 0.10 | 6.772 ± 0.052 | 42 |
| 14.01 ± 0.10 | 6.322 ± 0.045 | 21 |
| 14.48 ± 0.10 | 6.118 ± 0.042 | 35 |
| 14.80 ± 0.10 | 5.988 ± 0.041 | 23 |
| 15.15 ± 0.10 | 5.850 ± 0.039 | 52 |
| 16.28 ± 0.10 | 5.444 ± 0.033 | 18 |
| 16.70 ± 0.10 | 5.309 ± 0.032 | 20 |
| 16.90 ± 0.10 | 5.246 ± 0.031 | 22 |
| 17.92 ± 0.10 | 4.950 ± 0.028 | 70 |
| 18.64 ± 0.10 | 4.761 ± 0.025 | 36 |
| 20.88 ± 0.10 | 4.255 ± 0.020 | 42 |
| 21.35 ± 0.10 | 4.163 ± 0.019 | 25 |
| 21.68 ± 0.10 | 4.099 ± 0.019 | 18 |
| 22.42 ± 0.10 | 3.966 ± 0.018 | 38 |
| 23.10 ± 0.10 | 3.850 ± 0.017 | 55 |
| 23.54 ± 0.10 | 3.780 ± 0.016 | 20 |
| 23.95 ± 0.10 | 3.715 ± 0.015 | 37 |
| 24.67 ± 0.10 | 3.609 ± 0.014 | 44 |
| 25.29 ± 0.10 | 3.522 ± 0.014 | 68 |
| 26.38 ± 0.10 | 3.379 ± 0.013 | 33 |
| 26.96 ± 0.10 | 3.307 ± 0.012 | 33 |
| 27.63 ± 0.10 | 3.229 ± 0.012 | 22 |
| 28.36 ± 0.10 | 3.147 ± 0.011 | 29 |
| 29.07 ± 0.10 | 3.072 ± 0.010 | 35 |

TABLE 1B

| °2θ | d space (Å) | Intensity (%) |
|---|---|---|
| 4.90 ± 0.10 | 18.027 ± 0.375 | 71 |
| 6.86 ± 0.10 | 12.891 ± 0.191 | 100 |
| 8.41 ± 0.10 | 10.512 ± 0.126 | 61 |
| 9.83 ± 0.10 | 8.996 ± 0.092 | 63 |
| 10.13 ± 0.10 | 8.730 ± 0.087 | 97 |
| 17.92 ± 0.10 | 4.950 ± 0.028 | 70 |
| 23.10 ± 0.10 | 3.850 ± 0.017 | 55 |
| 25.29 ± 0.10 | 3.522 ± 0.014 | 68 |

In one embodiment provided herein, the polymorph form A of sodium 2-(5-bromo-4-(4-cyclopropylnaphthalen-1-yl)-4H-1,2,4-triazol-3-ylthio)acetate is characterized by x-ray powder diffraction pattern peaks at 4.90, 9.83, and 25.29°2θ±0.1°2θ. In further embodiments, the polymorph form A is further characterized by at least one peak appearing at 6.86, 8.41, 10.13, 17.92, and 23.10°2θ±0.1°2θ. In further embodiments, the polymorph form A is further characterized by at least two peaks appearing at 6.86, 8.41, 10.13, 17.92, and 23.10°2θ±0.1°2θ. In yet still further embodiments, the polymorph exhibits an x-ray powder diffraction pattern substantially the same as the x-ray powder diffraction pattern shown in FIG. 13.

Polymorph Form B

In one embodiment, sodium 2-(5-bromo-4-(4-cyclopropylnaphthalen-1-yl)-4H-1,2,4-triazol-3-ylthio)acetate polymorph Form B exhibits an x-ray powder diffraction pattern characterized by the diffraction pattern summarized in Table 2A or 2B. In some embodiments, provided herein is a polymorph of sodium 2-(5-bromo-4-(4-cyclopropylnaphthalen-1-yl)-4H-1,2,4-triazol-3-ylthio)acetate comprising at least 2 peaks of (±0.1°2θ) of Table 2A or 2B. In certain embodiments, provided herein is a polymorph of sodium 2-(5-bromo-4-(4-cyclopropylnaphthalen-1-yl)-4H-1,2,4-triazol-3-ylthio)acetate comprising at least 3 peaks of (±0.1°2θ) of Table 2A or 2B, at least 4 peaks of (±0.1°2θ) of Table 2A or 2B, at least 5 peaks of (±0.1°2θ) of Table 2A, at least 6 peaks of (±0.1°2θ) of Table 2A, at least 8 peaks of (±0.1°2θ) of Table 2A, at least 10 peaks of (±0.1°2θ) of Table 2A, at least 12 peaks of (±0.1°2θ) of Table 2A, at least 14 peaks of (±0.1°2θ) of Table 2A, or at least 16 peaks of (±0.1°2θ) of Table 2A.

TABLE 2

| | A | | | B | |
|---|---|---|---|---|---|
| °2θ | d space (Å) | Intensity (%) | °2θ | d space (Å) | Intensity (%) |
| 4.22 ± 0.10 | 20.939 ± 0.508 | 100 | 4.22 ± 0.10 | 20.939 ± 0.508 | 100 |
| 8.51 ± 0.10 | 10.392 ± 0.123 | 79 | 8.51 ± 0.10 | 10.392 ± 0.123 | 79 |
| 12.80 ± 0.10 | 6.917 ± 0.054 | 40 | 12.80 ± 0.10 | 6.917 ± 0.054 | 40 |
| 13.97 ± 0.10 | 6.337 ± 0.045 | 20 | 16.95 ± 0.10 | 5.231 ± 0.031 | 45 |
| 14.46 ± 0.10 | 6.126 ± 0.042 | 21 | | | |
| 16.19 ± 0.10 | 5.475 ± 0.034 | 23 | | | |
| 16.95 ± 0.10 | 5.231 ± 0.031 | 45 | | | |
| 18.40 ± 0.10 | 4.821 ± 0.026 | 22 | | | |
| 19.13 ± 0.10 | 4.639 ± 0.024 | 26 | | | |
| 19.48 ± 0.10 | 4.558 ± 0.023 | 24 | | | |
| 20.03 ± 0.10 | 4.433 ± 0.022 | 25 | | | |
| 21.28 ± 0.10 | 4.176 ± 0.019 | 23 | | | |
| 22.56 ± 0.10 | 3.942 ± 0.017 | 32 | | | |
| 22.90 ± 0.10 | 3.883 ± 0.017 | 27 | | | |
| 23.53 ± 0.10 | 3.781 ± 0.016 | 24 | | | |
| 25.64 ± 0.10 | 3.474 ± 0.013 | 28 | | | |
| 27.27 ± 0.10 | 3.271 ± 0.012 | 18 | | | |
| 28.17 ± 0.10 | 3.138 ± 0.011 | 15 | | | |
| 28.72 ± 0.10 | 3.108 ± 0.011 | 19 | | | |

In one embodiment provided herein, the polymorph form B of sodium 2-(5-bromo-4-(4-cyclopropylnaphthalen-1-yl)-4H-1,2,4-triazol-3-ylthio)acetate is characterized by x-ray powder diffraction pattern peaks at 4.22, 8.51, and 16.95°2θ±0.1°2θ. In a further embodiment, the polymorph form B is further characterized by a peak appearing at 12.80°2θ±0.1°2θ. In yet still further embodiments, the polymorph exhibits an x-ray powder diffraction pattern substantially the same as the x-ray powder diffraction pattern shown in FIG. 17.

Polymorph Form B'

In one embodiment, sodium 2-(5-bromo-4-(4-cyclopropylnaphthalen-1-yl)-4H-1,2,4-triazol-3-ylthio)acetate polymorph Form B' exhibits an x-ray powder diffraction pattern characterized by the diffraction pattern summarized in FIG. 19.

Admixture with Amorphous Solid State Forms

In certain embodiments, any of the polymorphs described herein (e.g., Form 1) optionally comprises (or is intermixed or in combination with) a certain amount of amorphous 2-(5-bromo-4-(4-cyclopropylnaphthalen-1-yl)-4H-1,2,4-triazol-3-ylthio)acetate. In some embodiments, the amorphous component of the polymorph (e.g., Form 1) or polymorph combination comprises less than 50 wt. % of the polymorph or polymorph combination, less than 25 wt. % of the polymorph or polymorph combination, less than 15 wt. % of the polymorph or polymorph combination, less than 10 wt. % of the polymorph or polymorph combination, or less than 5 wt. % of the polymorph or polymorph combination.

In certain embodiments, any of the polymorphs described herein (e.g., Form A) optionally comprises (or is intermixed or in combination with) a certain amount of amorphous sodium 2-(5-bromo-4-(4-cyclopropylnaphthalen-1-yl)-4H-1,2,4-triazol-3-ylthio)acetate. In some embodiments, the amorphous component of the polymorph (e.g., Form A) or polymorph combination comprises less than 50 wt. % of the polymorph or polymorph combination, less than 25 wt. % of the polymorph or polymorph combination, less than 15 wt. % of the polymorph or polymorph combination, less than 10 wt. % of the polymorph or polymorph combination, or less than 5 wt. % of the polymorph or polymorph combination.

Particle Size

In certain embodiments, provided herein is a 2-(5-bromo-4-(4-cyclopropylnaphthalen-1-yl)-4H-1,2,4-triazol-3-ylthio)acetate polymorph particle (e.g., crystalline, or comprising a crystalline component). In some embodiments, provided herein is a 2-(5-bromo-4-(4-cyclopropylnaphthalen-1-yl)-4H-1,2,4-triazol-3-ylthio)acetate polymorph (e.g., crystalline, or comprising a crystalline component) having a particle size of about 5-50 microns. In some embodiments, the average particle size is at least 10 microns, 15-50 microns, 15-35 microns, 35-45 microns, 35-40 microns, about 40 microns, or the like. In some embodiments, particles of 2-(5-bromo-4-(4-cyclopropylnaphthalen-1-yl)-4H-1,2,4-triazol-3-ylthio)acetate (e.g., crystalline, or comprising a crystalline component, such as a polymorph of Form 1) having an average diameter of greater than 5 or 10 microns have improved stability parameters compared to smaller diameters.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

Prodrugs are generally drug precursors that, following administration to an individual and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. They are, for instance, bioavailable by oral administration whereas the parent is not. In certain instances, the prodrug also has improved solubility in pharmaceutical compositions over the parent drug. An example, without limitation, of a prodrug would be a compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyamino acid) bonded to an acid group where the peptide is metabolized to reveal the active moiety. (See for example Bundgaard, "Design and Application of Prodrugs" in *A Textbook of Drug Design and Development*, Krosgaard-Larsen and Bundgaard, Ed., 1991, Chapter 5, 113-191, which is incorporated herein by reference).

In some embodiments, prodrugs are designed as reversible drug derivatives, for use as modifiers to enhance drug transport to site-specific tissues. The design of prodrugs to date has been to increase the effective water solubility of the therapeutic compound for targeting to regions where water is the principal solvent.

Additionally, prodrug derivatives of compounds described herein can be prepared by methods described herein are otherwise known in the art (for further details see Saulnier et al., *Bioorganic and Medicinal Chemistry Letters*, 1994, 4, 1985). By way of example only, appropriate prodrugs can be prepared by reacting a non-derivatized compound with a suitable carbamylating agent, such as, but not limited to, 1,1-acyloxy-alkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds are prodrugs for another derivative or active compound.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound of the present invention. In some embodiments, prodrugs include compounds comprising as alkyl ester. In some of such embodiments, an alkyl ester is cleave in vivo to provide Compound 1. Non-limiting examples of ester prodrugs include methyl, ethyl, propyl, isopropyl, butyl, isobutyl, tert-butyl, isoamyl, pentyl, hexyl, heptyl, octyl, nonyl, terpenyl, bornyl, allyl, linalyl or geranyl esters.

Pharmaceutically acceptable prodrugs of the compounds described herein also include, but are not limited to, esters, carbonates, thiocarbonates, N-acyl derivatives, N-acyloxy-alkyl derivatives, quaternary derivatives of tertiary amines, N-Mannich bases, Schiff bases, amino acid conjugates, phosphate esters, metal salts and sulfonate esters. Compounds having free amino, amido, hydroxy or carboxylic groups can be converted into prodrugs. For instance, free carboxyl groups can be derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

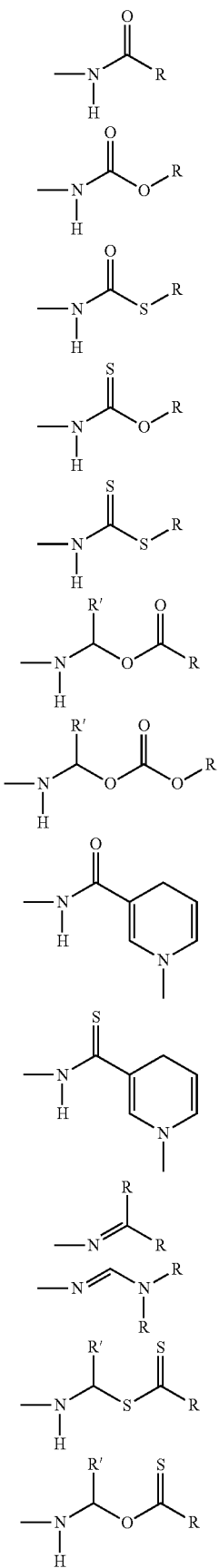

-continued

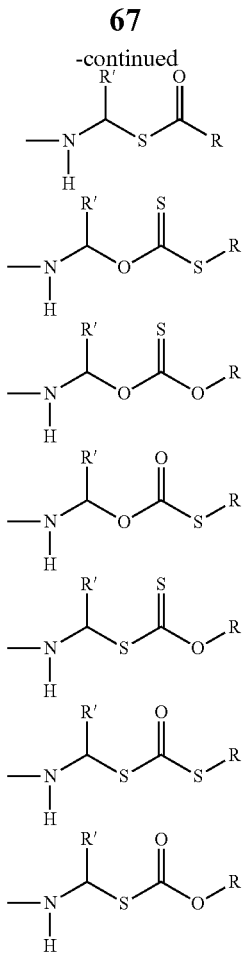

as well as sulfonamides and phosphonamides.

EXAMPLES

The examples and preparations provided below further illustrate and exemplify the compounds of the present invention and methods of preparing such compounds. It is to be understood that the scope of the present invention is not limited in any way by the scope of the following examples and preparations.

Example 1A

Synthesis of Compound 2

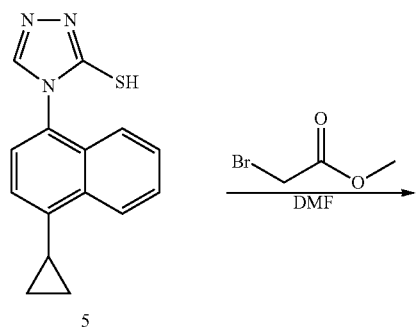

-continued

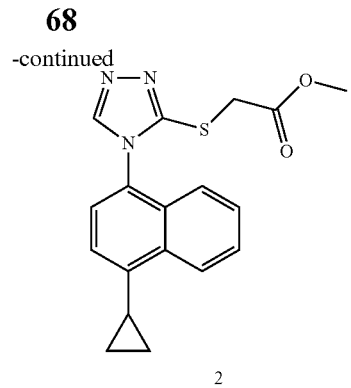

Charge dimethylformamide (2.63 kg±5%<>2.8 L±5%) to a reactor. Heat the dimethylformamide to a temperature between 27° C. and 35° C. Charge Compound 5 (1.0 kg±1%) to the same reactor in portions whilst maintaining the temperature between 27° C. and 35° C. Add methyl bromoacetate (0.6008/M×100 kg±1%<>0.3620/M×100 L±1%) to the reaction mixture whilst maintaining the temperature between 27° C. and 35° C., e.g., between 28° C. and 33° C., where M is the purity of the methyl bromoacetate by GC in % area. The methyl bromoacetate addition is slightly exothermic.

Stir the mixture for at least 10 minutes and not more than 20 minutes, at a temperature between 27° C. and 35° C., e.g., between 28° C. and 33° C.

Add to the reaction mixture sodium bicarbonate (0.314 kg±1%) in portions whilst maintaining the temperature between 27° C. and 35° C., over a period of at least 30 minutes and not more than 70 minutes. During the portion additions of sodium bicarbonate gaseous carbon dioxide is released.

Stir the mixture for at least 1 hour and not more than 4 hours, at a temperature between 27° C. and 35° C., e.g., between 28° C. and 33° C. Cool the reaction mixture to a temperature between 5° C. and 10° C., and then sample for HPLC analysis.

The reaction is considered complete if the content of Compound 5 is below 0.50% area by HPLC, preferentially below 0.20% area by HPLC. If reaction completion is not achieved after the second sample, heat the reaction mixture to a temperature between 27° C. and 35° C. Add methyl bromoacetate (0.0172/M×100 kg±1%<>0.0103/M×100 L±1%) to the reaction mixture whilst maintaining the temperature between 27° C. and 35° C., e.g., between 28° C. and 33° C. Stir the mixture for at least 30 minutes and not more than 2 hours, at a temperature between 27° C. and 35° C., e.g., between 28° C. and 33° C., then sample for HPLC analysis.

If reaction is complete, add to the reaction mixture over at least 15 minutes, while maintaining the temperature between 5° C. and 20° C., ozonated deionised water (9.0 L±5%). During the addition the gaseous carbon dioxide can be released. The ozonated deionised water addition is slightly exothermic. Stir the mixture for at least 30 minutes while maintaining the temperature between 5° C. and 10° C.

Add to the mixture, over at least 10 minutes, while maintaining the temperature between 5° C. and 20° C., a solution previously prepared by dissolution of sodium bicarbonate (0.105 kg±1%) in ozonated deionised water (1.47 L±5%), until a pH of the mixture between 6.7 and 8.0, e.g., between 6.9 and 7.3. Stir the suspension for at least 60 minutes while maintaining the temperature between 5° C. and 10° C. Filter the suspension. Wash the wet cake with ozonated deionised water (2.0 L±5%) previously cooled to a temperature between 5° C. and 10° C., twice.

Wash the wet cake with a mixture of ethyl acetate (0.09 kg±5%< >0.1 L±5%) and isopropyl alcohol (0.79 kg±5%< >1.0 L±5%) previously cooled to a temperature between 0° C. and 5° C., twice.

Dry the wet cake under vacuum at a temperature below 45° C., until the water content (by Karl Fischer analysis) is lower than, or equal to, 0.5% w/w, preferentially lower than, or equal to, 0.1% w/w, the content of ethyl acetate by GC is lower than, or equal to, 200 ppm, the content of isopropyl alcohol by GC is lower than, or equal to, 600 ppm and the content of dimethylformamide by GC is lower than, or equal to, 10000 ppm.

Example 1B

Synthesis of Compound 2

Large-Scale Preparation of Methyl 2-((4-(4-cyclopropylnaphthalen-1-yl)-4H-1,2,4-triazol-3-yl)thio)acetate The batch size for the large-scale preparation methyl 2-((4-(4-cyclopropylnaphthalen-1-yl)-4H-1,2,4-triazol-3-yl)thio)acetate is 1.0 kg. The stoichiometric yield is calculated to be 126.95% w/w, with the expected yield being 120±6% w/w (95±5% molar).

Step 1

Charge dimethylformamide (2.86 kg±5%; 3.05 L±5%) to a reactor, and heat to 15-23° C. Add 4-(4-cyclopropylnaphthalen-1-yl)-4H-1,2,4-triazole-3-thiol (1.0 kg±1.5%) to the reactor in portions, maintaining the temperature between 15° C. and 23° C. Add sodium bicarbonate (0.161 kg±1%) to the reactor, maintaining the temperature between 15° C. and 23° C. Add methyl bromoacetate (0.6095 kg±1%; 0.3672 L±1%) to the reactor, maintaining the temperature between 15° C. and 30° C., preferably between 17° C. and 21° C.

If methyl bromoacetate purity is <99.0%, (by GC) then add the quantity according to the formula: 0.6065/M×100 kg±1%; 0.3654/M×100 L±1%, where M is the purity of the methyl bromoacetate (by GC in % area). The methyl bromoacetate addition is slightly exothermic. Rinse the charging line with dimethylformamide (0.19 kg±5%; 0.2 L±5%), adding the rinse to the reactor, maintaining the temperature between 15° C. and 30° C., preferably between 17° C. and 21° C.

Stir the mixture for at least 20 minutes and not more than 40 minutes, maintaining the temperature between 15° C. and 30° C., preferably between 17° C. and 21° C. Add sodium bicarbonate (0.161 kg±1%) to the reactor in portions, over at least 20 minutes but not more than 120 minutes, maintaining the temperature between 15° C. and 30° C. Note, the addition of sodium bicarbonate is endothermic, and gaseous carbon dioxide is released. Stir the mixture for at least 1 hour and not more than 8 hours, maintaining the temperature between 15° C. and 30° C., preferably between 17° C. and 21° C.

The reaction is considered complete when the content of 4-(4-cyclopropylnaphthalen-1-yl)-4H-1,2,4-triazole-3-thiol is below 1.0% area by HPLC, preferably below 0.50% area by HPLC. If reaction is complete, proceed with STEP 3. If reaction is not complete, take another sample for HPLC analysis; if reaction is still not complete, proceed with STEP 2.

Step 2

Add methyl bromoacetate (0.01146 kg±1%; 0.00683 L±1%) to the reactor, maintaining the temperature between 15° C. and 30° C., preferably between 17° C. and 21° C.

If methyl bromoacetate purity is <99.0%, (by GC) then add the quantity according to the formula: 0.0114/M×100 kg±1%; 0.0068/M×100 L±1%, where M is the purity of the methyl bromoacetate (by GC in % area). Rinse the charging line with dimethylformamide (4.7 kg±5%; 5 L±5%–fixed quantity), adding the rinse to the reactor, maintaining the temperature between 15° C. and 30° C., preferably between 17° C. and 21° C.

Stir the mixture for at least 30 minutes but not more than 2 hours, maintaining the temperature between 15° C. and 30° C., preferably between 17° C. and 21° C. The reaction is considered complete when the content of 4-(4-cyclopropylnaphthalen-1-yl)-4H-1,2,4-triazole-3-thiol is below 1.0% area by HPLC, preferably below 0.50% area by HPLC.

If reaction is complete, proceed with STEP 3. If reaction is not complete, take another sample for HPLC analysis. If reaction is still not complete after the second sample, repeat STEP 2.

Step 3

Add ozonated, deionised water (0.5 L±5%) to the reaction mixture over at least 15 minutes, maintaining the temperature between 10° C. and 30° C. The addition is slightly exothermic and may release gaseous carbon dioxide. Stir the mixture for at least 30 minutes, maintaining the temperature between 10° C. and 30° C., during which time a precipitate may form, which is slightly exothermic.

Add a second portion of ozonated deionised water (8.5 L±5%) to the reaction mixture over at least 30 minutes, maintaining the temperature between 10° C. and 30° C., during which time the product precipitates. The addition is exothermic and carbon dioxide may be released.

Cool the suspension to 5-10° C. Measure the pH of the suspension. If necessary, adjust the pH to between 6.3 and 8.3, preferably between 6.9 and 7.3, by adding over at least 10 minutes, a previously prepared solution of sodium bicarbonate (0.105 kg±1%) in ozonated deionised water (1.47 L±5%), maintaining the temperature between 5° C. and 10° C.

Add ozonated deionised water (1.0 L±5%) over at least 10 minutes, maintaining the temperature between 5° C. and 10° C. Stir the suspension for at least 60 minutes, maintaining the temperature between 5° C. and 10° C.

Step 4

Filter the suspension. Wash the wet cake with ozonated, deionised water (2.0 L±5%) previously cooled to between 5° C. and 10° C. Wash the wet cake a second time with ozonated, deionised water (2.0 L±5%) previously cooled to 5-10° C. Wash the wet cake with a solution of ethyl acetate (0.09 kg±5%; 0.1 L±5%) and isopropyl alcohol (0.79 kg±5%; 1.0 L±5%) previously cooled to 0-5° C. Wash the wet cake with a solution of ethyl acetate (0.09 kg±5%; 0.1 L±5%) and isopropyl alcohol (0.79 kg±5%; 1.0 L±5%) previously cooled to 0-5° C.

Dry the wet cake under vacuum below 60° C., until the water content (by Karl Fischer analysis) is ≤0.2% w/w, preferably ≤0.1% w/w; the ethyl acetate content (by GC) is ≤200 ppm; the isopropyl alcohol content (by GC) is ≤600 ppm; and the dimethylformamide content (by GC) is ≤10000 ppm.

Example 2A

Synthesis of Compound 1 and Compound 4

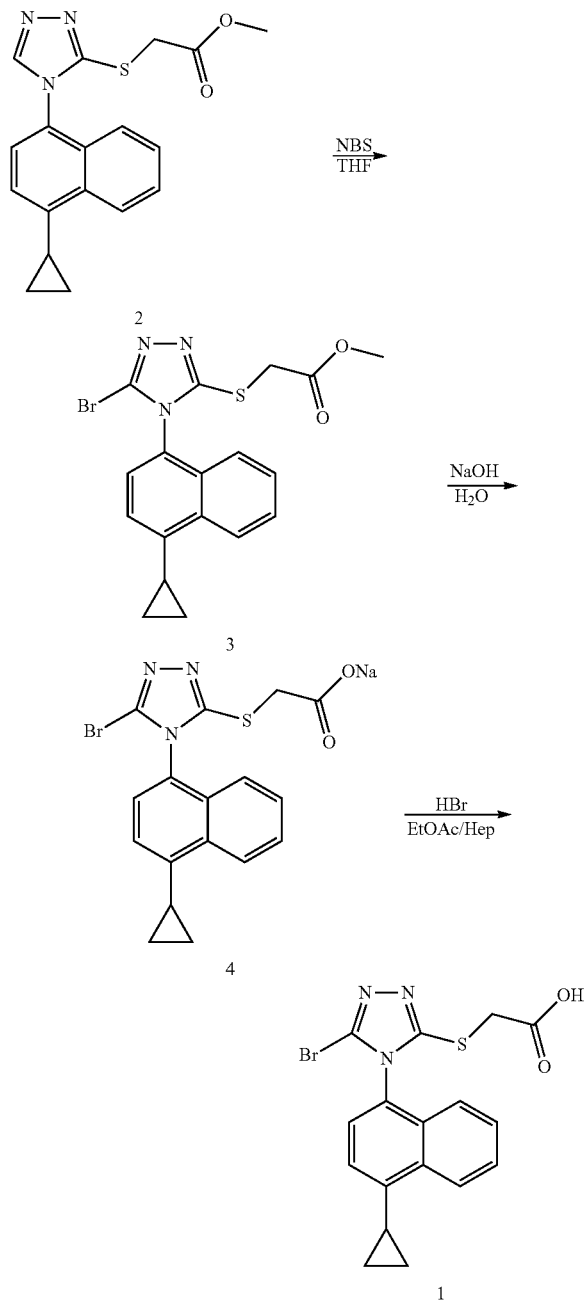

Charge Compound 2 (1.0 kg±1%) to a reactor. Add tetrahydrofuran (6.2 kg±1%< >7.0 L±1%) to the same reactor. Heat the mixture to a temperature between 35° C. and 42° C. Stir the mixture for at least 10 minutes at a temperature between 35° C. and 42° C. to obtain a clear solution. Cool the reaction mixture to a temperature between 27° C. and 32° C.

Add N-bromosuccinimide (0.734 kg±1%) to the reaction mixture whilst maintaining the temperature between 27° C. and 32° C., e.g., between 27° C. and 30° C. Stir the mixture at a temperature between 27° C. and 32° C., e.g., between 27° C. and 30° C., until the reaction is complete.

The reaction is considered complete when the content of Compound 2 is lower than 1.5% area by HPLC, preferentially lower than 0.2% area by HPLC.

The reaction is sampled for HPLC analysis after 20 to 40 minutes of stirring for the determination of the Compound 2 content. Based on HPLC analysis, optionally add extra quantity of N-bromosuccinimide (0.105 kg±1%) while maintaining the temperature between 27° C. and 32° C., e.g., 27° C. and 30° C. Otherwise, continue with the stirring at a temperature between 27° C. and 32° C., e.g., between 27° C. and 30° C., until the reaction is complete.

Cool the reaction mixture to a temperature between 2° C. and 7° C., e.g., between 2° C. and 5° C. Add toluene (4.33 kg±5%) to the mixture, while maintaining the temperature between 2° C. and 7° C., e.g., between 2° C. and 5° C.

Add to the reaction mixture, over at least 10 minutes, while maintaining the temperature between 2° C. and 7° C., e.g., between 2° C. and 5° C., ozonated deionised water (5.0 L±5%). The addition of the ozonated deionised water is exothermic and during the addition gaseous release may occur. Stir the mixture for at least 30 minutes maintaining the temperature between 2° C. and 7° C., e.g., between 4° C. and 6° C.

Stop stirring and allow layers to separate for at least 30 minutes. Discharge the aqueous (lower phase). Add to the organic phase, over at least 10 minutes, while maintaining the temperature between 2° C. and 7° C., a solution previously prepared by dissolution of sodium disulfite (0.112 kg±1%) in ozonated deionised water (5.0 L±5%). The addition of the sodium disulfite solution is exothermic. During the addition gaseous release may occur.

Stir the suspension for at least 30 minutes maintaining the temperature between 2° C. and 7° C. Take a sample of the mixture. If the aqueous phase of the sample is pale yellow, conduct another wash step with sodium disulfite. If the aqueous phase of the sample is colorless then send sample for HPLC analysis. If the peak of N-bromosuccinimide is detected by HPLC then conduct another wash with sodium disulfite and repeat the HPLC analysis till the NBS is not longer detectable by HPLC.

Stop stirring and allow layers to separate for at least 15 minutes. Discharge the aqueous phase (lower phase) and combine with the previous aqueous phase. Heat the organic phase comprising Compound 3 to a temperature between 18° C. and 25° C. Add to the organic phase, maintaining the temperature between 18° C. and 25° C., ozonated deionised water (5.0 L±5%). Stir the mixture for at least 15 minutes maintaining the temperature between 18° C. and 25° C. Stop stirring and allow layers to separate for at least 15 minutes. Discharge the aqueous phase (lower phase).

Add to the organic phase, maintaining the temperature between 18° C. and 25° C., a solution previously prepared by dissolution of sodium bicarbonate (0.35 kg±1%) in ozonated deionised water (5.0 L±5%). Stir the mixture for at least 15 minutes maintaining the temperature between 18° C. and 25° C. Stop stirring and allow layers to separate for at least 15 minutes. Discharge the aqueous phase (lower phase).

If the pH of the discharged aqueous phase is below 8.0, repeat the wash step with sodium bicarbonate until the pH of the aqueous phase is above 8.0.

Add to the organic phase, comprising Compound 3, over at least 10 minutes, while maintaining the temperature between 18° C. and 25° C., a solution previously prepared by dissolution of sodium hydroxide (pure) (0.1473 kg±1%) in ozonated deionised water (3.61 L±5%).

Stir the mixture at a temperature between 18° C. and 25° C. for at least 2 hours until the reaction is complete. The reaction is considered complete when the peak area by HPLC of Compound 3 in the organic phase is lower than 50 mAU. If reaction is incomplete then stir the reaction mixture an extra 2 hours before re-sampling. If reaction completion is not achieved after 6 hours stirring, add extra quantity of sodium hydroxide aqueous solution and re-sample 3 hours after the addition. The reaction mixture has two phases at this point. Stop stirring and allow layers to separate for at least 30 minutes. Discharge the aqueous phase (lower phase) to a reactor or receiver. Repeat this step and combine the aqueous layers. Discharge the organic phase (upper phase) for disposal.

Concentrate the aqueous phases under a vacuum at a temperature lower than, or equal to, 40° C. until no distillates are collected using a vacuum pressure not lower than 75 mbar.

Take a sample of the aqueous phase for determination of the content of Compound 4 in the concentrated aqueous phase. Adjust the volume of the concentrated aqueous phase to a volume of about 5.5×W L±5% where W is the amount of Compound 1 in Kg calculated from the assay sample.

Cool the mixture to a temperature between 5° C. and 0° C. over at least 2 hours. Stir the mixture for at least 2 hours maintaining the temperature between 0° C. and 5° C. Crystallization of the sodium salt, i.e., Compound 4, occurs at this point.

Heat the suspension to a temperature between 17° C. and 19° C. Stir the mixture for at least 1 hour maintaining the temperature between 17° C. and 19° C. Compound 4 sodium salt remains crystallized after this stirring period.

Cool the mixture to a temperature between 15° C. and 13° C. over at least 4 hours. Cool the mixture to a temperature between 5° C. and 0° C. over at least 2 hours. Stir the mixture for at least 2 hours, and preferentially not more than 4 hours, maintaining the temperature between 0° C. and 5° C.

Filter the suspension. Wash the wet cake up to 3 times with ozonated deionised water (0.50 L±5%) previously cooled to a temperature between 0° C. and 5° C. under nitrogen flow combined with vacuum Dissolve the wet cake comprising Compound 4 with ozonated deionised water (4.5 L±5%) at a temperature not higher than 35° C., and transfer the solution to a reactor or a receiver. Take a sample of the aqueous solution for determination of the Compound 1 content (W2). W2 is the amount of Compound 1 in Kg calculated from the assay sample.

Add to the aqueous solution ethyl acetate (9.0×W2 kg±5%< >10.0×W2 L±5%) Add to the mixture, while maintaining the temperature below or equal to 35° C., hydrobromic acid 24% in water (variable quantity), until a pH of the mixture is between 2.0 and 4.0, e.g., between 3.0 and 4.0. Add sodium hydroxide aqueous solution to mixture if pH drops below 2.0. Stir the mixture for at least 30 minutes maintaining the temperature between 30° C. and 35° C. Stop stirring and allow layers to separate for at least 30 minutes.

Discharge the organic phase (upper phase) to a reactor or a receiver and take a sample of the aqueous phase for HPLC analysis. If the peak area by HPLC of Compound 1 is higher than 500 mAU then repeat the wash with hydrobromic acid and combine the aqueous phases comprising Compound 1.

Add to the aqueous phase ethyl acetate (0.9×W2 kg± 5%< >1.0×W2 L±5%) while maintaining the temperature between 30° C. and 35° C. Stir the mixture for at least 30 minutes maintaining the temperature between 30° C. and 35° C. Stop stirring and allow layers to separate for at least 30 minutes.

Discharge the organic phase (upper phase) to a reactor or a receiver and take a sample of the aqueous phase for HPLC analysis. If the peak area by HPLC of Compound 1 is higher than 500 mAU then repeat the extraction with ethyl acetate Discharge the aqueous phase (lower phase) for disposal. Add to the combined organic phase, while maintaining the temperature between 30° C. and 35° C., ozonated deionised water (2.0×W2 L±5%). Stir the mixture for at least 30 minutes maintaining the temperature between 30° C. and 35° C. Stop stirring and allow layers to separate for at least 30 minutes. Discharge the aqueous phase (lower phase) for disposal.

Filter the organic phase through a filter with porosity not higher than 1 micron, and transfer the filtrate to a reactor or a receiver. Concentrate the filtered organic phase under vacuum at a temperature below or equal to 38° C., e.g., at a temperature between 18° C. and 25° C., until a final volume between 7.3×W2 L and 7.7×W2 L. Compound 1 can crystallize at this point.

Heat the mixture to a temperature between 35° C. and 42° C., e.g., between 38° C. and 40° C. and stir over at least 3 hours, and not more than 8 hours, e.g., between 3 and 5 hours, while maintaining the temperature.

Optionally free acid seed of Compound 1 is added as a solid or suspended in n-heptane (0.5×W2 L–fixed quantity) previously filtered through a filter with porosity not higher than 1 micron.

Concentrate the filtered organic phase under vacuum at a temperature below or equal to 38° C., e.g., at a temperature between 18° C. and 25° C., until a final volume between 3.8×W2 L and 4.2×W2 L.

Add to the suspension, while maintaining the temperature between 35° C. and 42° C., e.g., between 38° C. and 40° C., n-heptane (0.68×W2 kg±5%< >1.0×W2 L±5%) previously filtered through a filter with porosity not higher than 1 micron. Stir the mixture for at least 1 hour maintaining the temperature between 35° C. and 42° C., preferably between 38° C. and 40° C. Cool the mixture to a temperature between 10° C. and 5° C. over at least 2 hours. Filter the suspension.

Wash the wet cake with a solution of ethyl acetate (0.63× W2 kg±5%< >0.7×W2 L±5%) and n-heptane (0.48×W2 kg±5%<>0.7×W2 L±5%) previously cooled to a temperature between 5° C. and 10° C. and filtered through a filter with porosity not higher than 1 micron. Dry the wet cake under vacuum at a temperature lower or equal to 50° C., until the content of n-heptane by GC is lower than, or equal to, 5000 ppm, the content of ethyl acetate by GC is lower than, or equal to, 2500 ppm, and water content (by Karl Fischer analysis) is lower than, or equal to, 0.5% w/w.

Example 2B

Synthesis of Compound 1 and Compound 4

Large-Scale Preparation of 2-(5-Bromo-4-(4-cyclopropylnaphthalen-1-yl)-4H-1,2,4-triazol-3-ylthio) acetate The batch size for the large-scale preparation of 2-(5-bromo-4-(4-cyclopropylnaphthalen-1-yl)-4H-1,2,4-triazol-3-ylthio)acetate is 1.0 kg. The stoichiometric yield is calculated to be 119.1% w/w, with the expected yield being 89±24% w/w (75±20% molar).

Step 1

Charge methyl 2-((4-(4-cyclopropylnaphthalen-1-yl)-4H-1,2,4-triazol-3-yl)thio)acetate (1.0 kg±2%) to a reactor. Add tetrahydrofuran (6.0 kg±1%; 6.8 L±1%) to the reactor. Heat the mixture to a temperature between 25° C. and 35° C., preferably between 29° C. and 31° C.

Add N-bromosuccinimide (0.8128 kg±1%) to the reactor in <3 hours, maintaining the temperature between 25° C. and 40° C., preferably between 31° C. and 34° C. Rinse the charging line with tetrahydrofuran (0.18 kg±1%; 0.20 L±1%) adding the rinse to the reactor, maintaining the temperature between 25° C. and 40° C., preferably between 31° C. and 34° C.

Stir the mixture at a temperature between 25° C. and 40° C., preferably between 31° C. and 34° C., until the reaction is complete. The reaction is considered complete when the content of methyl 2-((4-(4-cyclopropyl naphthalen-1-yl)-4H-1, 2,4-triazol-3-yl)thio)acetate is <1.5% area by HPLC, preferably <0.2% area by HPLC. If reaction is not complete after 3 hours consider adding extra N-bromosuccinimide (0.052 kg±1%) at 25-40° C., preferably between 31° C. and 34° C., rinsing the charging line with tetrahydrofuran (0.18 kg±1%; 0.20 L±1%) and adding the rinse to the reactor while maintaining the temperature at 25-40° C., preferably between 31° C. and 34° C. Age after the additional N-bromosuccinimide charge before re-sampling.

Step 2

Cool the reaction mixture to 2-7° C., preferably between 2° C. and 5° C. Add toluene (5.20 kg±5%; 6.0 L±5%) to the reactor, maintaining the temperature between 2° C. and 7° C., preferably between 2° C. and 5° C.

Add ozonated, deionised water (5.0 L±5%) to the reactor over at least 10 minutes, maintaining the temperature between 2° C. and 7° C., preferably between 2° C. and 5° C. The addition is exothermic and gaseous release may occur. Stir for at least 30 minutes maintaining the temperature between 2° C. and 7° C., preferably between 4° C. and 6° C. Stop stirring and allow layers to separate for at least 30 minutes. If an emulsion is obtained add toluene (0.43 kg±5%; 0.5 L±5%), maintaining the temperature between 2° C. and 7° C., preferably between 4° C. and 6° C., and stir the mixture for 15 minutes before re-settling the phases. Discharge the aqueous, lower phase.

To the organic phase, add a previously prepared solution of sodium disulfite (0.154 kg±1%) in ozonated, deionised water (5.0 L±5%), over at least 10 minutes, maintaining the temperature between 2° C. and 7° C. The addition is exothermic and gaseous release may occur. During sodium disulfite solution preparation, add extra sodium disulfite (0.028 kg±1%) for each extra quantity of N-bromosuccinimide (0.052 kg±1%) added during the bromination reaction, up to a maximum charged quantity of sodium disulfite (0.196 kg±1%).

Stir the suspension for at least 30 minutes maintaining the temperature between 2° C. and 7° C. Stop stirring and allow layers to separate for at least 15 minutes. Discharge the aqueous phase, lower phase and combine with the previously discharged aqueous phase.

Heat the organic phase to 18-25° C. Add ozonated, deionised water (5.0 L±5%) to the organic phase, maintaining the temperature between 18° C. and 25° C. Stir for at least 15 minutes maintaining the temperature between 18° C. and 25° C. Stop stirring and allow layers to separate for at least 15 minutes. Discharge the aqueous phase, lower phase.

Add a previously prepared solution of sodium bicarbonate (0.42 kg±1%) in ozonated deionised water (6.01±5%) to the organic phase, maintaining the temperature between 18° C. and 25° C. Gaseous release may occur during the addition. Stir for at least 15 minutes maintaining the temperature between 18° C. and 25° C. Stop stirring and allow layers to separate for at least 15 minutes. Discharge the aqueous phase, lower phase. Measure the pH of the discharged aqueous phase. If it is below 8.0 proceed with STEP 3. If it is above 8.0 proceed with STEP 4.

Step 3

Add a previously prepared solution of sodium bicarbonate (0.42 kg±1%) in ozonated deionised water (6.0 L±5%) to the organic phase, maintaining the temperature between 18° C. and 25° C. Gaseous release may occur during the addition. Stir for at least 15 minutes maintaining the temperature between 18° C. and 25° C. Stop stirring and allow layers to separate for at least 15 minutes. Discharge the aqueous phase, lower phase. Measure the pH of the discharged aqueous phase. If pH is below 8.0 repeat STEP 3. If pH is above 8.0 proceed with STEP 4.

Step 4

Add a previously prepared solution of pure sodium hydroxide (0.1473 kg±1%) in ozonated, deionised water (3.61 L±5%) to the organic phase, over at least 10 minutes, maintaining the temperature between 20° C. and 30° C. Stir the mixture at a temperature between 20° C. and 30° C. for at least 2 hours until the reaction is complete. The reaction is considered complete when the peak area by HPLC of methyl 2-((5-bromo-4-(4-cyclopropylnaphthalen-1-yl)-4H-1,2,4-triazol-3-yl)thio)acetate in the organic phase is lower than 150 mAU* (at 292 nm). Measure the pH after 2 hours of stirring. If the pH is ≥12.0, analyze the sample by HPLC for peak area of methyl 2-((5-bromo-4-(4-cyclopropylnaphthalen-1-yl)-4H-1,2,4-triazol-3-yl)thio)acetate in the organic phase. If the pH of the reaction mixture is ≤12.0 add a previously prepared solution of pure sodium hydroxide (0.0118 kg±1%) in ozonated, deionised water (0.29 L±5%), and re-sample for pH and/or HPLC after 2 hours of stirring. The extra addition of sodium hydroxide solution is repeated until the HPLC peak area of methyl 2-((5-bromo-4-(4-cyclopropylnaphthalen-1-yl)-4H-1,2,4-triazol-3-yl)thio)acetate is ≤12.0

The reaction mixture has two phases at this point; stop stirring and allow layers to separate for at least 30 minutes. Discharge the aqueous, lower phase to a reactor or receiver.

Add a previously prepared solution of pure sodium hydroxide (0.002 kg±1%) in ozonated, deionised water (2.0 L±5%) to the organic phase, maintaining the temperature between 18° C. and 25° C. Stir for at least 30 minutes maintaining the temperature between 18° C. and 25° C. Stop stirring and allow layers to separate for at least 30 minutes. Discharge the lower aqueous phase and combine with the previous aqueous phase. Discharge the upper organic phase for disposal.

Take a sample of the combined aqueous phases for determination of 2-((5-bromo-4-(4-cyclopropylnaphthalen-1-yl)-4H-1,2,4-triazol-3-yl)thio)acetic acid content. Concentrate the aqueous phases under vacuum at ≤50° C., preferably between 35° C. and 45° C., until a final volume between 5.0 and 5.6×W L, (where W is the amount of 2-((5-bromo-4-(4-cyclopropylnaphthalen-1-yl)-4H-1,2,4-triazol-3-yl)thio) acetic acid ("free acid") in kg calculated from the assay sample. The jacket temperature of the reactor should not exceed 55° C.

Step 5

Cool to 0-5° C., over at least 2 hours, and stir for at least an additional 2 hours, maintaining the temperature between 0° C. and 5° C. Crystallization of sodium 2-((4-(4-cyclopropyl naphthalen-1-yl)-4H-1,2,4-triazol-3-yl)thio)acetate should occur at this point. Heat the suspension to 17-19° C., and stir for at least an additional 1 hour, maintaining the temperature between 17° C. and 19° C. The salt Na should remain crystallized during this stirring period. Cool to 13-15° C. over at least 4 hours. Cool further to 0-5° C. over at least 2 hours. Stir for at least 2 hours, and preferably not more than 4 hours, maintaining the temperature at 0-5° C.

Step 6

Filter the suspension at 0-5° C. Part of the mother liquors may be used to rinse the product from the reactor walls. If required, wash the wet cake up to three times with ozonated, deionised water (0.45×W L±5%) previously cooled to 0-5° C. Use nitrogen flow combined with vacuum. Upon transfer, material should be on hold in the filter prior to filtration for a minimum of 30 minutes.

Step 7

Dissolve the wet cake in ozonated deionised water (4.0×W L±5%) at a temperature≤50° C., preferably between 35° C. and 45° C., and transfer the solution to a reactor or receiver. The jacket temperature of the reactor and/or filter should be <55° C. Wash the reactor and filter with ozonated deionised water (0.5×W L±5%) and combine the wash with the previous aqueous solution. Again, wash the reactor and filter with ozonated deionised water (0.5×W L±5%) and combine the wash with the previous aqueous solution.

Remove a sample of the dissolved sodium salt solution for determination of 2-((5-bromo-4-(4-cyclopropylnaphthalen-1-yl)-4H-1,2,4-triazol-3-yl)thio)acetic acid ("free acid"; W2) content. If W2 is 5% lower in relation W, than use W2 instead of W in STEPS 10 and 11.

Add ethyl acetate (9.9×W kg±5%; 11.0×W L±5%). Add hydrobromic acid 24% in water (variable quantity), to achieve a pH of between 2.0 and 4.0, preferably between 2.5 and 3.5, maintaining the temperature≤38° C., preferably between 28° C. and 33° C. The expected quantity required is about 0.80×W kg; 0.66×W L of hydrobromic acid solution. Add aqueous sodium hydroxide solution if pH drops below 2.0.

Stir for at least 30 minutes maintaining the temperature≤38° C., preferably between 28° C. and 33° C. Stop stirring and allow layers to separate for at least 30 minutes. Discharge the upper organic phase to a reactor or a receiver and remove a sample of the aqueous phase for HPLC analysis. If the peak area by HPLC of the free acid is >500 mAU* (292 nm) proceed with STEP 8. If the peak area by HPLC of the free acid is <500 mAU* (292 nm) proceed with STEP 9.

Step 8

Add ethyl acetate (0.9×W2 kg±5%; 1.0×W2 L±5%) to the aqueous phase, maintaining the temperature≤38° C., preferably between 28° C. and 33° C. Stir the mixture for at least 30 minutes maintaining the temperature≤38° C., preferably between 28° C. and 33° C. Stop stirring and allow layers to separate for at least 30 minutes. Discharge the upper organic phase to a reactor or a receiver, combining with the previous organic phase, and remove a sample of the aqueous phase for HPLC analysis. If the peak area by HPLC of the free acid is >500 mAU* (292 nm) repeat STEP 8. If the peak area by HPLC of the free acid is >500 mAU* (292 nm) proceed with STEP 9.

Step 9

Add ozonated, deionised water (2.0×W 1±5%) to the combined organic phase, maintaining the temperature between 30° C. and 35° C. Stir for at least 30 minutes maintaining the temperature between 30° C. and 35° C. Stop stirring and allow layers to separate for at least 30 minutes. Discharge the lower, aqueous phase for disposal.

Add ozonated deionised water (2.0×W 1±5%) to the organic phase, maintaining the temperature between 30° C. and 35° C., Stir for at least 30 minutes maintaining the temperature between 30° C. and 35° C. Stop stirring and allow layers to separate for at least 30 minutes. Discharge the lower, aqueous phase for disposal. Filter the organic phase (filter porosity<1 µm) and transfer the filtrate to a reactor or a receiver. Wash the reactor and filter with ethyl acetate (0.45×W kg±5%; 0.5×W L±5%) and transfer the filtrate to a reactor or a receiver.

Step 10

Concentrate the filtered organic phase under vacuum at ≤38° C., preferably between 18° C. and 25° C. (jacket temperature of the reactor should not exceed 42° C.), to a final volume of 7.3-7.7×W L, during which time the product may crystallize. Heat to 35-42° C. for at least 3 hours, preferably 3-5 hours. Stir the mixture for at least 4 hours, preferably <8 hours, maintaining the temperature between 35° C. and 42° C., preferably between 38° C. and 40° C. The product should have crystallized by the beginning of this step. If crystallization is not observed after 1 hour stirring at 35-42° C., the batch may be seeded, added as a solid (variable quantity) or suspended in n-heptane (0.5×W L–fixed quantity) previously filtered (filter porosity<1 µm).

Concentrate the filtered organic phase under vacuum at ≤38° C., preferably at a temperature between 18° C. and 25° C. (jacket temperature<42° C.), to a final volume between 3.5×W L and 3.8×W L. Heat to 35-42° C. for at least 1 hour, preferably not more than 4 hours. Add n-heptane (0.85×W kg±5%; 1.25×W L±5%) previously filtered (filter porosity<1 µm) to the suspension over at least 1 hour, maintaining the temperature between 35° C. and 42° C., preferably between 38° C. and 40° C. Stir for at least 1 hour maintaining the temperature between 35° C. and 42° C., preferably between 38° C. and 40° C. Cool to 5-10° C. over at least 2 hours. Stir for at least 2 hours at 5-10° C.

Step 11

Filter the suspension. If necessary use part of the mother liquors to rinse the product from the reactor walls prior to n-heptane wash. Wash the wet cake with a solution of ethyl acetate (0.63×W kg±5%; 0.7×W L±5%) and n-heptane (0.48×W kg±5%; 0.7×W L±5%) previously cooled to between −5 and 10° C., preferably 0-5° C., and filtered (filter porosity<1 µm). Dry the wet cake under vacuum at ≤60° C., until the content of: n-heptane by GC is ≤5000 ppm; ethyl acetate by GC is ≤2500 ppm; and water (by Karl Fischer analysis) is ≤0.5% w/w.

Example 2C

Synthesis of Compound 1 and Compound 4

Optimization of Bromination Step: Bromination of Compound 2 to Yield Compound 3

Several combinations of brominating agents, solvents, reaction times & temperatures were attempted to determine the optimal conditions for the bromination step. The results are summarized in the table below.

| Solvent | Brominating agent | Time h | Temperature °C. | Starting Material HPLC % | Product HPLC % |
|---|---|---|---|---|---|
| THF | NBS | 4 | 30 | 0.0 | 99.4 |
| THF TEMPO | NBS | 0.25 | 30 | 0.0 | 99.2 |
| THF | NBS + Br$_2$ | 3 | 30 | 1.7 | 91.6 |
| THF MTBE (1:1) | NBS | 24 | 30 | 0.6 | 90.1 |
| Toluene | NBS | 30 | 20 | 0.0 | 79.2 |
| DCM | NBS | 30 | 20 | 0.0 | 76.2 |
| Acetonitrile | NBS | 24 | 29 | 0.9 | 55.6 |
| DMF | NBS | 30 | 20 | 34.2 | 45.7 |
| Acetone | NBS | 30 | 20 | 41.6 | 29.2 |
| Methanol | NBS | 30 | 20 | 46.5 | 29.2 |
| IPAC | NBS | 30 | 20 | 52.2 | 29.2 |
| ACIP | NBS | 24 | 30 | 88.6 | 3.7 |
| Ethyl Acetate | NBS | 24 | 29 | 92.8 | 4.2 |
| MTBE | NBS | 24 | 29 | 94.3 | 4.7 |
| Cyclohexane | NBS | 24 | 30 | 96.1 | 3.3 |
| THF 1% water | NBS | 4 | 30 | 96.2 | 2.1 |
| THF | Br$_2$ | 3 | 30 | 97.2 | 0.0 |
| Ethyl Acetate 1% Acetic acid | NBS | 3 | 20 | 0.0 | 0.0 |

Example 3

Preparation of Compound 5 from Compound 8—Thiocyanate Method

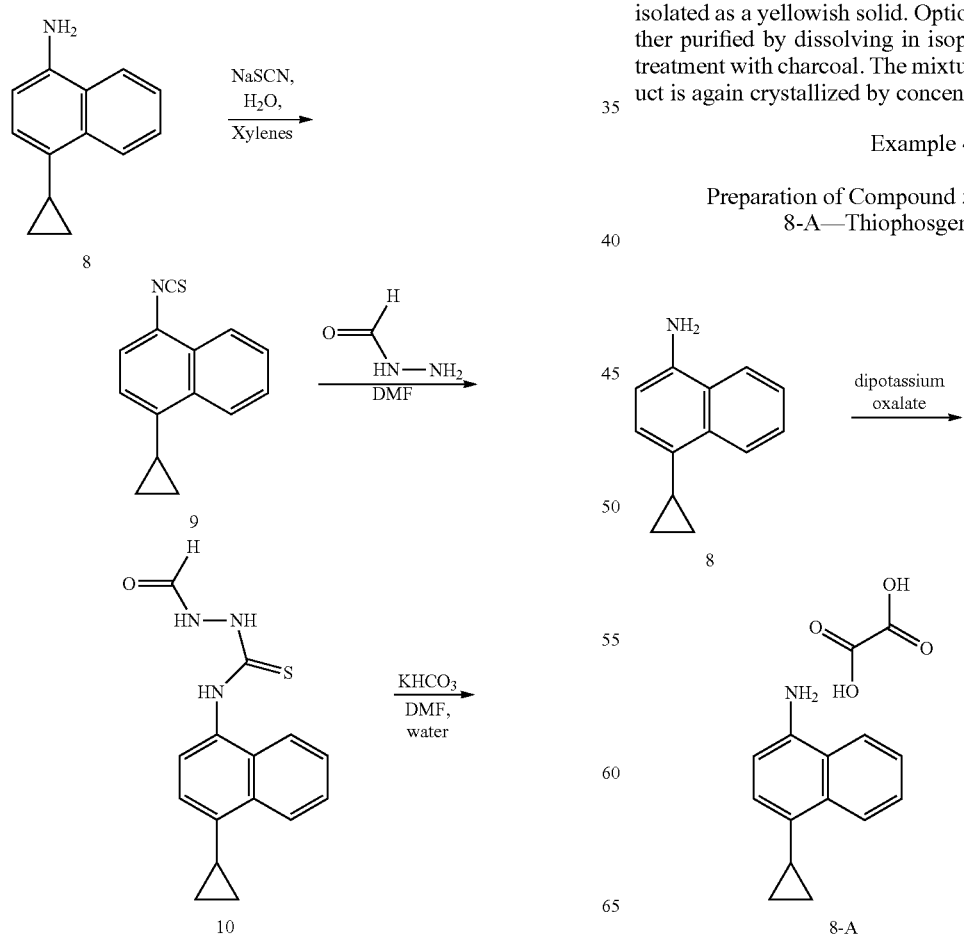

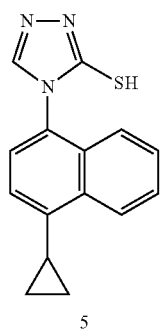

Compound 8 is suspended in xylenes together with sodium thiocyanate and water is added. The mixture is heated to 90° C. until Compound 8 is consumed. The mixture is further heated to 140° C., while water is distilled off, until the isothiocyanate Compound 9 is formed. Silicagel is added and the suspension is filtered. The solids are washed with xylenes and the filtrate is extracted twice with aqueous HCl. Subsequently the solution is concentrated in vacuo as much as possible and the residue is dissolved in DMF. A solution of formyl hydrazine in DMF is added. The mixture is stirred at 50-55° C. and an aqueous solution of potassium carbonate is added. Subsequently the mixture is stirred until complete conversion, cooled and the pH is adjusted to 6-7 by addition of sulfuric acid. The product is isolated by filtration, washed with isopropanol and water. After drying the product Compound 5 is isolated as a yellowish solid. Optionally Compound 5 is further purified by dissolving in isopropanol under reflux and treatment with charcoal. The mixture is filtered and the product is again crystallized by concentration in vacuo.

Example 4

Preparation of Compound 5 from Compound 8-A—Thiophosgene Method

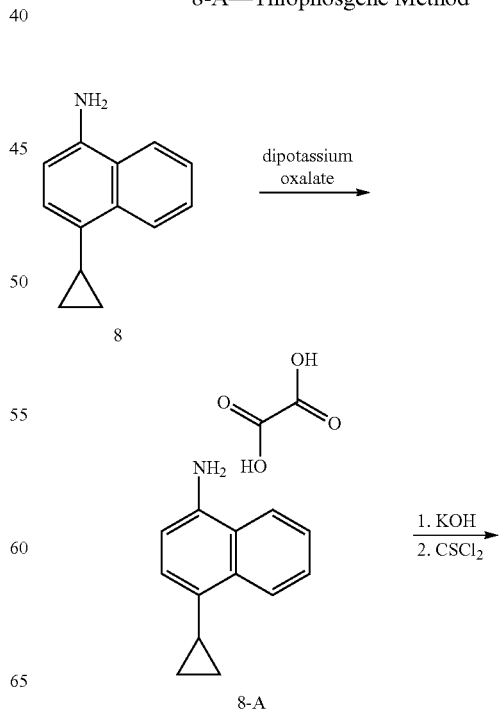

81

-continued

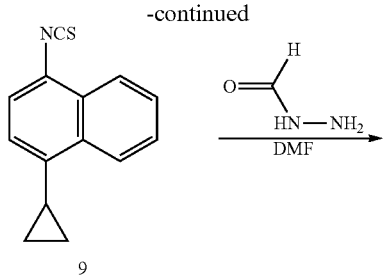

82

Example 5

Synthesis of Compound 1 from Compound 11

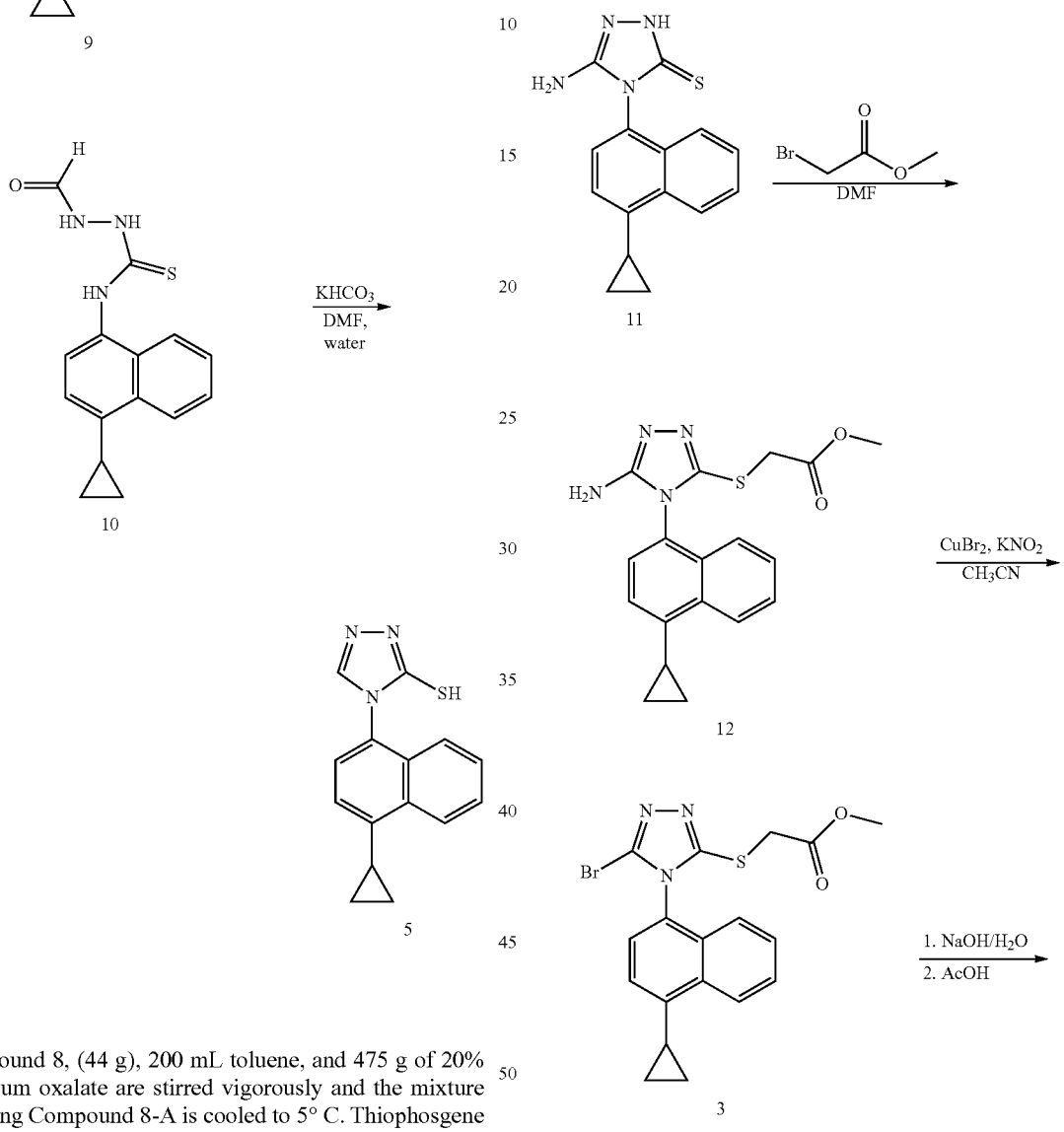

Compound 8, (44 g), 200 mL toluene, and 475 g of 20% dipotassium oxalate are stirred vigorously and the mixture comprising Compound 8-A is cooled to 5° C. Thiophosgene (1.5 L) is added over 1 hour. The mixture is filtered through celite and the cake is washed with toluene. The filtrate is collected and the toluene is removed in vacuo. The residue is dissolved in 16:1 Hexanes: Ethyl acetate and the mixture is filtered through silica gel. The filtrate is collected and the solvents removed in vacuo to provide Compound 9 as a solid (69 g).

6 g of Compound 9 is suspended in 12 mL acetonitrile and the mixture is heated to 35° C. 1.68 g of formyl hydrazide is added in three portions over twenty minutes and the mixture is stirred for 2 h at 35° C., then cooled to 4° C. and stirred overnight. The reaction mixture is filtered, the cake is washed with 5:1 hexane:ethyl acetate and dried at 40° C. to provide 5.85 g of Compound 5.

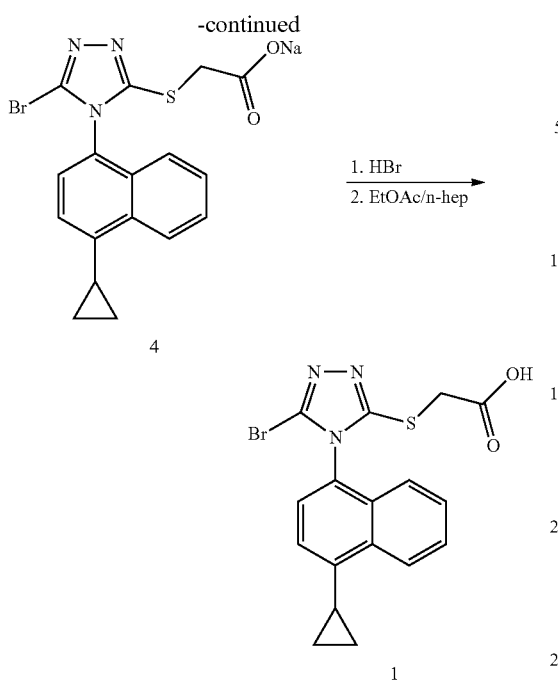

Compound 11 and methyl bromoacetate were dissolved in DMF and stirred at a temperature between 14 and 22° C. to give Compound 12. The product was isolated by cooling the reaction mixture to a temperature of 10-15° C. followed by an adjustment of the pH with aqueous sodium bicarbonate. The resulting solid, Compound 12, was filtered and was washed with water first, then with cold (0-5° C.) ethyl acetate.

Compound 12 was mixed with copper (II) bromide and potassium nitrite in acetonitrile and stirred at a temperature between 14 and 20° C. until reaction completion. After addition of aqueous sodium hydroxide and citric acid to the reaction mixture, the product, Compound 3, was extracted using toluene and the organic layer was washed several times with aqueous solutions of ammonium hydroxide and sodium citrate to remove copper salts.

Crude Compound 3 in solution underwent base-mediated hydrolysis with the addition of an aqueous sodium hydroxide solution. The biphasic mixture was stirred at 18-25° C. until completion of the ester hydrolysis then the pH of the aqueous layer was adjusted to between 8 and 9 using an aqueous solution of hydrobromic acid. After separation of the two phases, ethyl acetate was added to the aqueous layer, and the pH was adjusted to between 5.15 and 5.35 to extract the product, Compound 1, into the organic layer. This process was repeated several times until all of Compound 1 was extracted. The combined organic layers were heated at 30-35° C. then circulated through a bed of activated carbon and then through a filter with porosity lower than 0.5 micron. An aqueous solution of sodium bicarbonate was added to extract Compound 1 into the aqueous layer, the layer was concentrated under reduced pressure at a temperature below 40° C. and acetic acid was added while maintaining the temperature between 40 and 60° C.

The mixture was heated to a temperature between 73 and 77° C. and crude free acid of Compound 1 crystallized, at which point water was added. The crude free acid was filtered at 7-13° C., washed with a cold mixture of acetic acid and water, and dried under reduced pressure at a temperature below 50° C.

The sodium salt (Compound 4) was formed by addition of an equimolar aqueous solution of sodium hydroxide to a suspension of crude Compound 1 in water stirred at 18-25° C. Compound 4 crystallized upon cooling of the aqueous mixture, was filtered and washed with cold water, then was dissolved in warm water and filtered through a filter with porosity no higher than 1 micron. Ethyl acetate was added, the biphasic mixture was heated to 30-35° C. and an aqueous solution of hydrobromic acid was added. Compound 1 was extracted into the organic layer after addition of ethyl acetate. The organic layer containing the product was washed with water then concentrated under reduced pressure. Compound 1 crystallized from the solution. Variations in the amount of n-heptane are added to complete the crystallization. The crystalline Compound 1 was filtered and washed with a mixture of ethyl acetate and n-heptane and dried under reduced pressure while maintaining the temperature of the drier below 50° C.

Example 6

Synthesis of Compound 11—Method 1

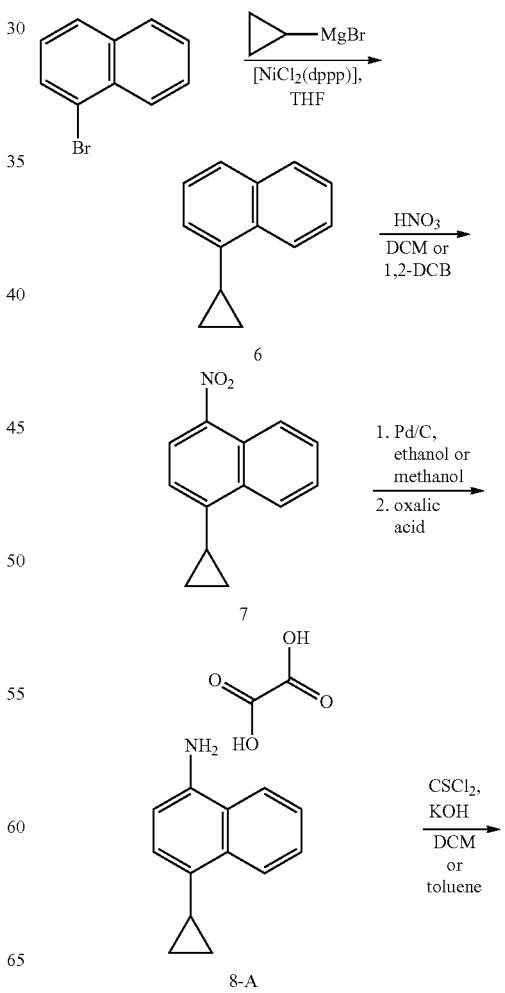

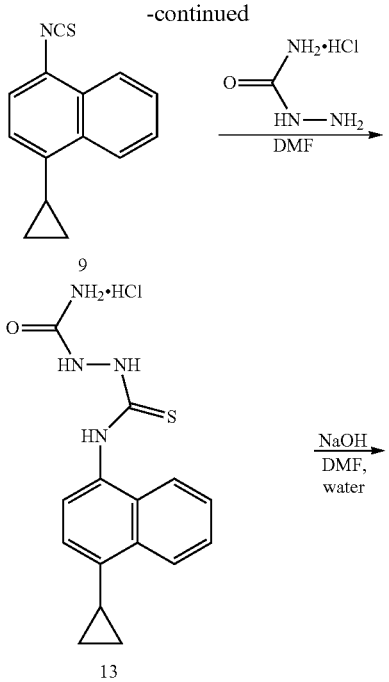

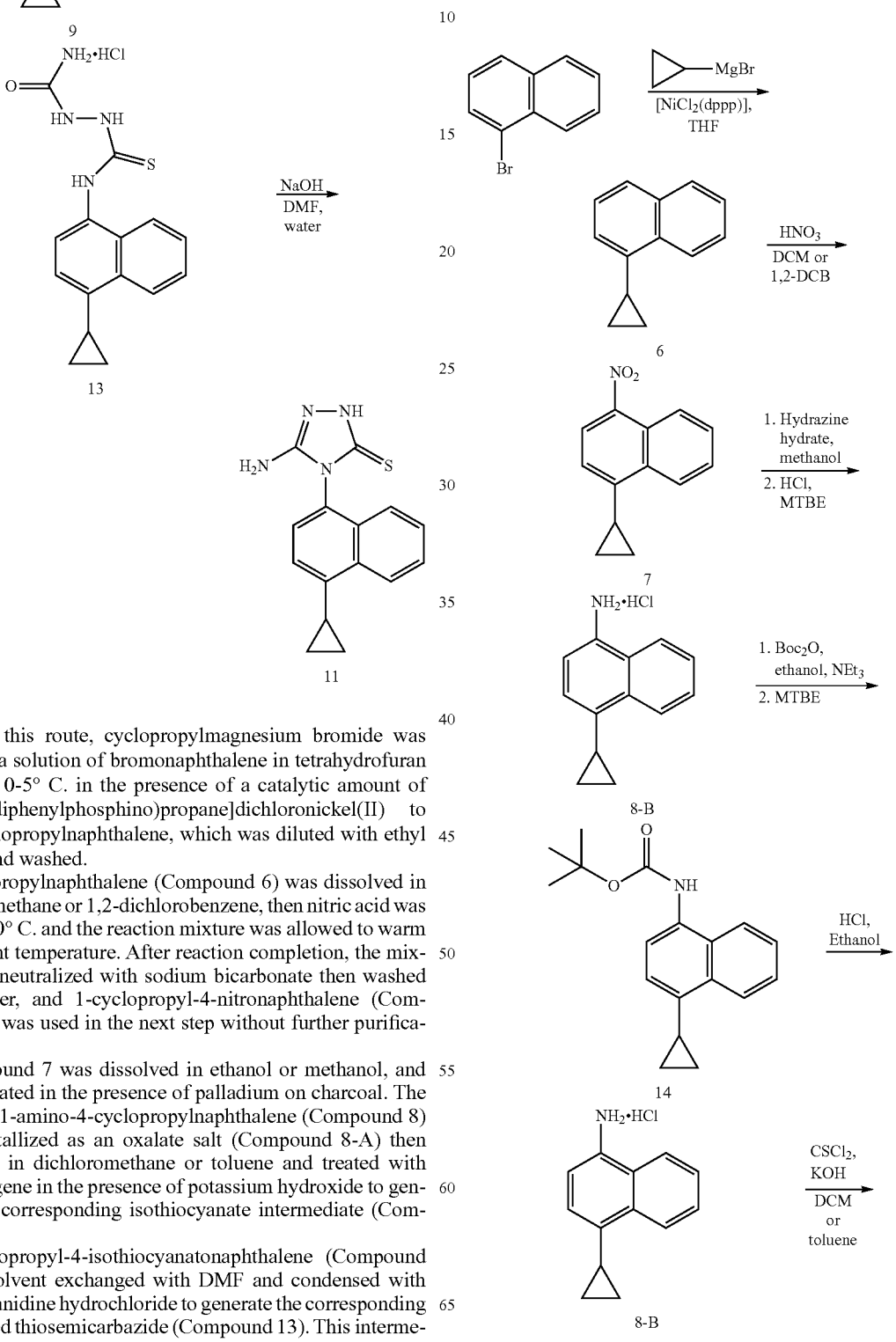

Under this route, cyclopropylmagnesium bromide was added to a solution of bromonaphthalene in tetrahydrofuran stirred at 0-5° C. in the presence of a catalytic amount of [1,3-bis(diphenylphosphino)propane]dichloronickel(II) to form cyclopropylnaphthalene, which was diluted with ethyl acetate and washed.

Cyclopropylnaphthalene (Compound 6) was dissolved in dichloromethane or 1,2-dichlorobenzene, then nitric acid was added at 0° C. and the reaction mixture was allowed to warm to ambient temperature. After reaction completion, the mixture was neutralized with sodium bicarbonate then washed with water, and 1-cyclopropyl-4-nitronaphthalene (Compound 7) was used in the next step without further purification.

Compound 7 was dissolved in ethanol or methanol, and hydrogenated in the presence of palladium on charcoal. The resulting 1-amino-4-cyclopropylnaphthalene (Compound 8) was crystallized as an oxalate salt (Compound 8-A) then dissolved in dichloromethane or toluene and treated with thiophosgene in the presence of potassium hydroxide to generate the corresponding isothiocyanate intermediate (Compound 9).

1-Cyclopropyl-4-isothiocyanatonaphthalene (Compound 9) was solvent exchanged with DMF and condensed with aminoguanidine hydrochloride to generate the corresponding substituted thiosemicarbazide (Compound 13). This intermediate Compound 13 was heated in the presence of aqueous sodium hydroxide to form Compound 11, which was purified by crystallization from a mixture of ethanol and water or a mixture of methanol, DMF and water.

Example 7

Synthesis of Compound 11—Method 2

-continued

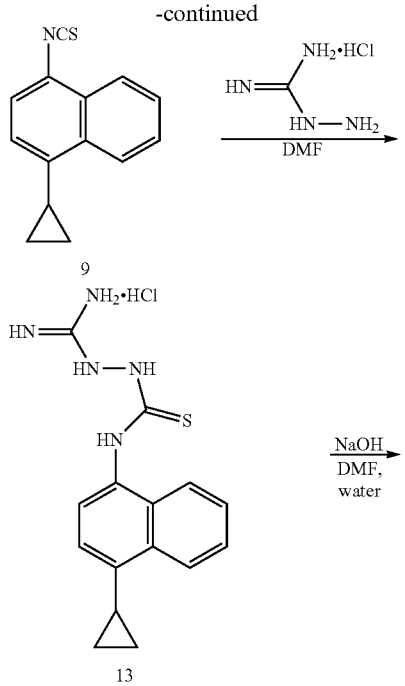

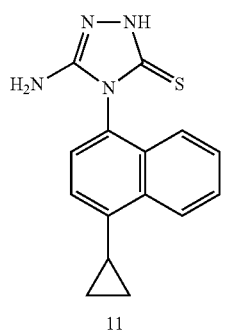 [SMILES: Nc1n[nH]c(=S)n1-c1ccc(C2CC2)c2ccccc12]

Cyclopropylmagnesium bromide was added to a solution of bromonaphthalene in tetrahydrofuran stirred at 0-5° C. in the presence of catalytic amount of [1,3-bis(diphenylphosphino)propane]dichloronickel(II) to form cyclopropylnaphthalene, which was diluted with ethyl acetate and washed.

Cyclopropylnaphthalene (Compound 6) was dissolved in dichloromethane, then nitric acid was added at 0° C. and the reaction mixture was allowed to warm to ambient temperature. After reaction completion, the mixture was neutralized with sodium bicarbonate then washed with water, and 1-cyclopropyl-4-nitronaphthalene (Compound 7) was used in the next step without further purification.

Compound 7 was dissolved in methanol, and hydrogenated with hydrazine hydrate at reflux temperature. The crude 1-amino-4-cyclopropylnaphthalene (Compound 8) was dissolved in ethanol and reacted with di-tert-butyl dicarbonate in the presence of triethylamine to give tert-butyl 4-cyclopropylnaphthalen-1-ylcarbamate (Compound 14) which was precipitated from methyl tert-butyl ketone.

The protecting group in Compound 14 was removed by hydrochloric acid in ethanol to afford amino-4-cyclopropylnaphthalene which crystallized as an hydrochloride salt (compound 8-B).

4-Cyclopropylnaphthalen-1-amine hydrochloride (Compound 8-B) was dissolved in dichloromethane and treated with thiophosgene in the presence of sodium hydroxide to generate the corresponding isothiocyanate intermediate Compound 9.

1-Cyclopropyl-4-isothiocyanatonaphthalene was solvent exchanged with DMF and condensed with aminoguanidine hydrochloride to generate the corresponding substituted thiosemicarbazide (Compound 13). Compound 13 was heated in the presence of aqueous sodium hydroxide to form Compound 11, which was purified by crystallization from a mixture of ethanol and water, then recrystallized from a mixture of dimethylformamide and water.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 8

Preparation of 2-(5-bromo-4-(4-cyclopropylnaphthalen-1-yl)-4H-1,2,4-triazol-3-ylthio)acetic acid-polymorph form 1

2-(5-Bromo-4-(4-cyclopropylnaphthalen-1-yl)-4H-1,2,4-triazol-3-ylthio)acetic acid-form 1 is prepared from crude sodium 2-(5-bromo-4-(4-cyclopropylnaphthalen-1-yl)-4H-1,2,4-triazol-3-ylthio)acetate as described below:

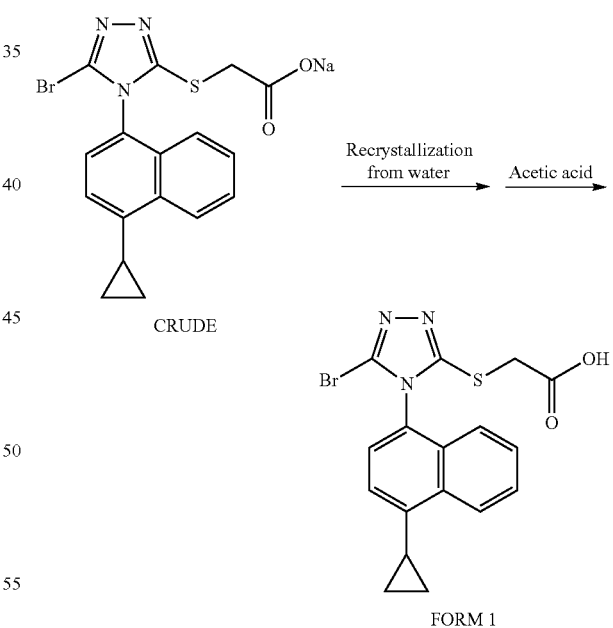

Step 1

Sodium 2-(5-bromo-4-(4-cyclopropylnaphthalen-1-yl)-4H-1,2,4-triazol-3-ylthio)acetate (60 g) and water (300 mL) were stirred and briefly heated (40-50° C.) until all solids dissolved. The solution was cooled and stirred in an ice bath for 1-2 hrs, after which time crystals began to form (or if crystallization had not begun, the solution was seeded with a small amount of sodium 2-(5-bromo-4-(4-cyclopropylnaphthalen-1-yl)-4H-1,2,4-triazol-3-ylthio)acetate crystals). Stirring in the ice bath was continued until crystallization was complete, and then the solid isolated by filtration through a sintered filter funnel (medium porosity) under vacuum. The filter cake was washed with ice-cold water (sufficient to cover the filter cake) and the liquid completely drained under vacuum to provide wet filter cake (126.5 g).

Step 2

The filter cake was dissolved in water (~70 g present in the filter cake plus 130 mL; concentration 200-250 mg/mL) at 60-70° C., and slowly added to acetic acid (200 mL). The acetic acid/water (1:1 v/v) solution was cooled to room temperature under continuous stirring, and then further cooled to 0° C., resulting in the formation of crystals which were isolated by vacuum filtration over a medium porosity sintered filter funnel. The solids were washed with ice-cold acid/water (1:1 v/v) and dried in a vacuum oven to provide 2-(5-bromo-4-(4-cyclopropylnaphthalen-1-yl)-4H-1,2,4-triazol-3-ylthio)acetic acid (39.5 g, 78%).

Example 9

Preparation of 2-(5-bromo-4-(4-cyclopropylnaphthalen-1-yl)-4H-1,2,4-triazol-3-ylthio)acetic acid-polymorph form 2

2-(5-Bromo-4-(4-cyclopropylnaphthalen-1-yl)-4H-1,2,4-triazol-3-ylthio)acetic acid-form 2 is prepared from sodium 2-(5-bromo-4-(4-cyclopropylnaphthalen-1-yl)-4H-1,2,4-triazol-3-ylthio)acetate as described below:

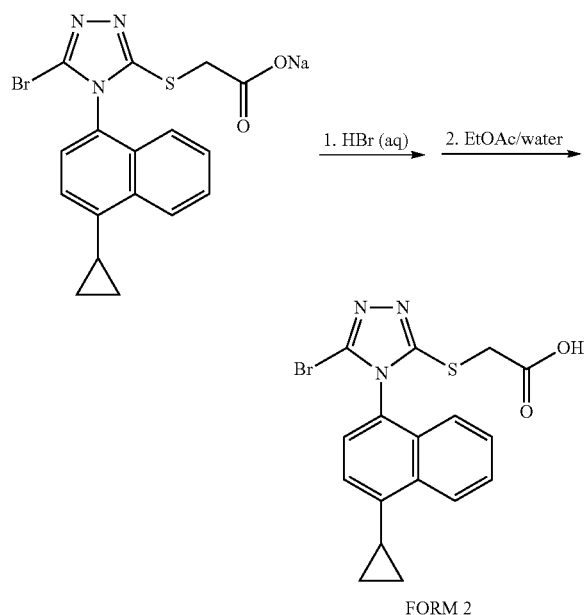

A suspension of sodium 2-(5-bromo-4-(4-cyclopropylnaphthalen-1-yl)-4H-1,2,4-triazol-3-ylthio)acetate (50.0 g of crude sample 97.6% a/a; KF=12.6%; 43.3 g calculated actual) and deionized water (217 mL) was heated (30-35° C.) with vigorous stirring for 10-15 min, during which time the slurry dissolved leaving only trace solids. The mixture was filtered through a medium-frit filter funnel and the clear filtrate cooled to 10° C. Approximately one half of a mixture of aqueous hydrogen bromide solution (48 wt %, 18 g, 106.8 mmol, 1.05 eq) and deionized water (~13 mL) was added to the filtrate over 10 min, at 10-15° C., during which time some solids were formed. Ethyl acetate (347 mL) was added with vigorous stirring resulting in dissolution of all solids. The remaining hydrogen bromide solution was added over 10 min at 10° C., and stirring continued for 5-10 min, during which time a cloudy suspension formed. Stirring was stopped, the phases allowed to separate and the aqueous layer removed. The organic layer was washed with deionized water (110 mL) with vigorous stirring for 5-10 min, and after phase separation the aqueous layer removed. The organic layer was heated to 45-50° C. and solvents removed using gentle vacuum, resulting in the formation of a slurry (final volume ~200 mL), which was warmed (45-50° C.) with moderate stirring for 1 h, gradually (3-4 h) cooled to 20-25° C., and held at 20-25° C. for an additional 12 h, and finally cooled to 5-10° C. and held for 20-30 min. The slurry was then filtered under vacuum through a Buchner funnel lined with Whatman No. 3 filter paper. There were fast filtering solids and the mother liquor was cycled through the vessel to recover residual solids which were collected with the initial batch. The solids were washed with cold (5° C.) ethyl acetate (26 mL) and allowed to dry on the funnel for at least 10 min, then soaked in n-heptane (30 mL) for at least 10 min and the vacuum reapplied for ~6 h. The solids were transferred to a drying dish and dried in a vacuum oven (25 mmHg) for at least 16 h at 35-40° C., with nitrogen sweep. 2-(5-Bromo-4-(4-cyclopropylnaphthalen-1-yl)-4H-1,2,4-triazol-3-ylthio)acetic acid-form 2 was obtained as a free flowing off-white solid (28.39 g, 69%), containing trace amounts of water (0.16 wt %) and ethyl acetate (700 ppm).

| Materials | Amount |
| --- | --- |
| Sodium 2-(5-bromo-4-(4-cyclopropyl naphthalen-1-y1)-4H-1,2,4-triazol-3-ylthio)acetate | 50.0 g crude (43.3 g corrected) |
| Hydrogen bromide (48 wt %) | 18.0 g |
| Water | 217 mL |
| Ethyl acetate | 346.7 mL |
| Water (wash 1) | 108.3 mL |
| Water (wash 2) | 108.3 mL |
| Ethyl acetate (wash) | 26 mL |
| n-Heptane (wash) | 30 mL |

Example 10

Conversion of 2-(5-bromo-4-(4-cyclopropylnaphthalen-1-yl)-4H-1,2,4-triazol-3-ylthio)acetic acid-Polymorph form 1 to Polymorph form 2

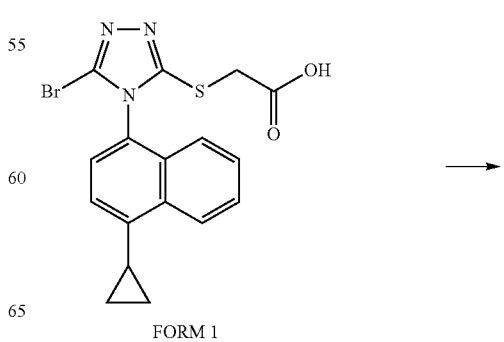

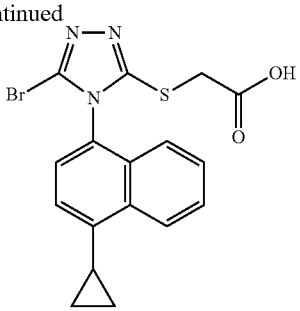

FORM 2

Method 1

Ethyl acetate (200 mL) was added to a solution of 2-(5-bromo-4-(4-cyclopropylnaphthalen-1-yl)-4H-1,2,4-triazol-3-ylthio)acetic acid-polymorph form 1 (30 g) in acetone (200 mL) at 60° C. A portion of the solvent (~200 mL) was removed under low vacuum and fresh ethyl acetate (200 mL) was added, followed by another distillation cycle, during which crystallization began. The temperature of the water bath was slowly increased to 70° C., during which time four additional ethyl acetate addition/distillation cycles were carried out to a final volume of ~200 mL. The mixture was allowed to cool slowly to room temperature and then placed in the fridge overnight. Solids were isolated by filtration, washed with ice-cold ethyl acetate and dried in a vacuum oven to provide of 2-(5-bromo-4-(4-cyclopropylnaphthalen-1-yl)-4H-1,2,4-triazol-3-ylthio)acetic acid-form 2.

Method 2

A solution of 2-(5-bromo-4-(4-cyclopropylnaphthalen-1-yl)-4H-1,2,4-triazol-3-ylthio)acetic acid-form 1 in one of the solvents listed below was slowly evaporated at room temperature to crystallize, refrigerated, the solid crystals isolated and washed with solvent to produce Solid Polymorph form 2, containing trace amounts of solvent and water, as indicated.

| Solvent | Solvent content (%) | Water content (%) | Purity | Polymorph Form |
|---|---|---|---|---|
| Butan-2-one | 0.35 | 0.36 | | 2 |
| | 0.49 | 0.53 | | |
| tent-Butanol | 0.32 | 0.17 | 94% | 2 |
| | 0.72 | 0.5 | 4% impurities | |
| Dichloromethane | 0.3 | 0.5 | | 2 |

Method 3

Solid Polymorph form 1 was held in equilibrium with its saturated acetonitrile, ethyl acetate or toluene solution at 60° C. for 6 days to produce Solid Polymorph form 2.

Solid Polymorph form 1 held in equilibrium with its saturated acetone solution at 60° C. for 6 days resulted in decomposition.

Method 4

Solid Polymorph form 1 and solvent (20 μL) were heated at 60° C. for 13 days to produce Solid Polymorph form 2.

| form 1 (mg) | Solvent | Polymorph Form Isolated |
|---|---|---|
| 928 | DMF | 2 |
| 927 | Dioxane | 2 |
| 883 | Acetic acid | 2 |
| 844 | Toluene | 2 |
| 844 | Acetonitrile/toluene (20 μL each) | 2 |
| 844 | Acetonitrile | 1 & 2 |
| 867 | iso-Propanol | 1 & 2 |
| 944 | Water | 1 |

Example 11A

Analysis of Crystalline Polymorph Form 1

X-Ray Powder Diffraction

The X-ray powder diffraction pattern of polymorph form 1 is shown in FIGS. 1 (raw data) and 2 (background subtracted and Kα2 stripped); observed and representative peaks in the XRPD pattern are shown in the tables below (generated on background corrected and Kα2 stripped file).

| form 1 Observed | | |
|---|---|---|
| °2θ | d space (Å) | Intensity (%) |
| 10.32 | 8.562 | 100 |
| 18.84 | 4.706 | 32.7 |
| 20.75 | 4.277 | 23.2 |
| 27.28 | 3.266 | 13.6 |
| 27.60 | 3.229 | 11 |
| 21.54 | 4.123 | 10.4 |
| 25.53 | 3.487 | 9.8 |
| 6.80 | 12.989 | 9.4 |
| 24.97 | 3.563 | 9.1 |
| 28.43 | 3.137 | 8.4 |
| 19.98 | 4.441 | 6.9 |
| 29.35 | 3.040 | 6.7 |
| 15.88 | 5.577 | 5.4 |
| 23.13 | 3.842 | 4.8 |
| 26.34 | 3.381 | 4.8 |
| 18.56 | 4.777 | 4.1 |

| form 1 Representative | | |
|---|---|---|
| °2θ | d space (Å) | Intensity (%) |
| 10.32 | 8.562 | 100 |
| 18.84 | 4.706 | 32.7 |
| 20.75 | 4.277 | 23.2 |
| 27.28 | 3.266 | 13.6 |

Differential Scanning calorimetry (DSC)

The differential scanning calorimetry trace for form 1 is shown in FIG. 3; a transition temperature of 150.7° C. was recorded.

Scanning Electron Microscopy (SEM)

SEM analysis showed form 1 primary crystals are composed of agglomerates (typical size ~25 μm) of plate-like crystals (size ~5 μm).

Thermogravimetric Analysis (TGA)

Figure 4:
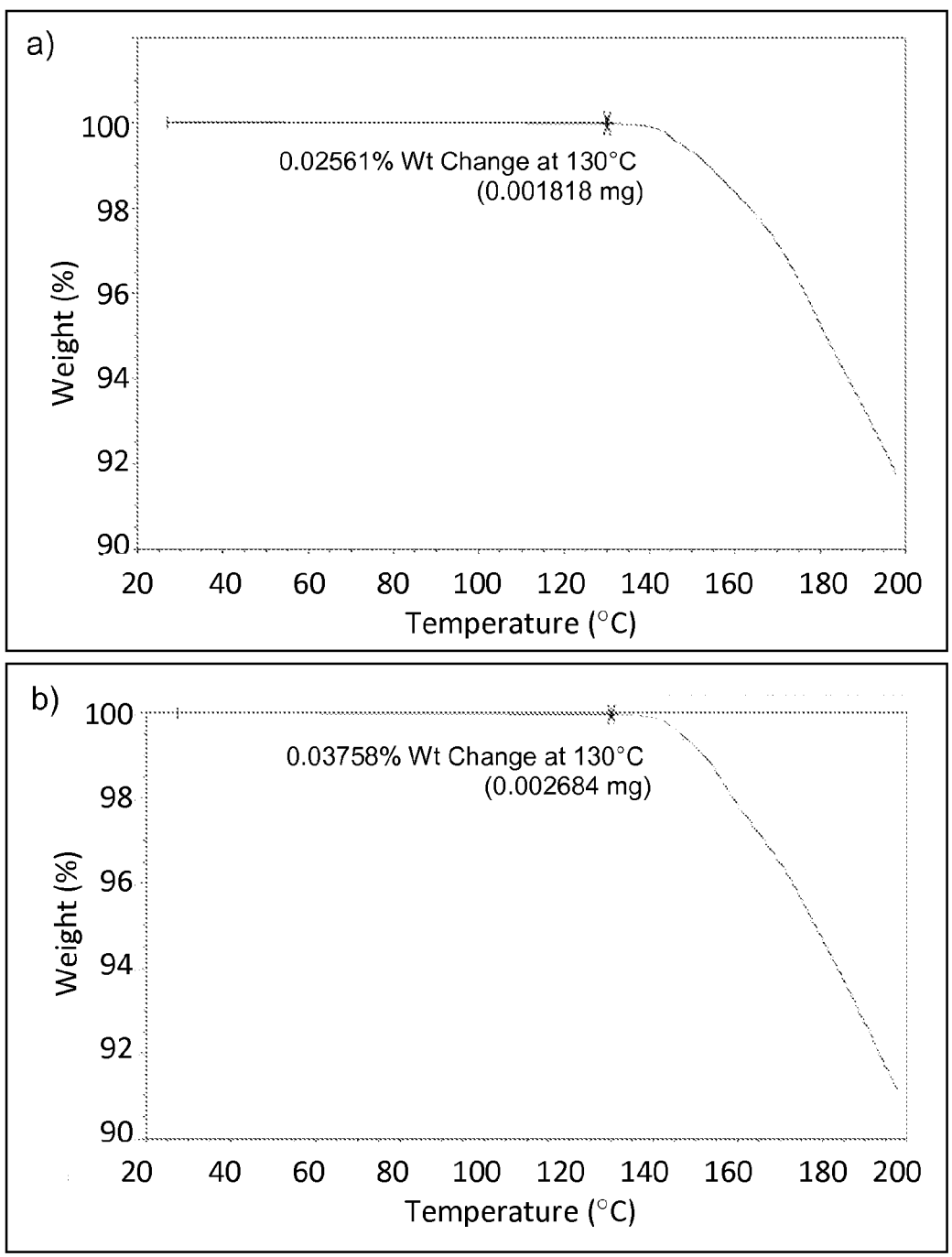
FIG. 4 represents illustrative Thermogravimetric Analyses (a) Rep 1 and (b) Rep 2 of Polymorph form 1.

Replicate TGA scans for form 1 are shown in FIG. 4 (*a*) and (*b*), indicating the material does not contain significant levels of volatiles Solubility Form 1 (~25 mg) and acetate buffer (25 mM, pH 5, 4 mL), prepared with and without sodium chloride (ionic strength adjusted to =0.1M), were placed in a glass vial which was sealed and placed on a laboratory rotator in a 25° C. incubator. After 1, 5, and 7 days the samples were filtered and assayed by HPLC. Form 1 solubility (mg/mL), at the various time points, with and without sodium chloride, is shown in the table below:

|  | Day 1 | Day 5 | Day 7 |
|---|---|---|---|
| No NaCl | 0.2652 (pH 4.95) | 0.2134 (pH 4.85) | 0.1569 (pH 4.75) |
| NaCl (I = 0.1) | 0.2995 | 0.2566 (pH 4.79) | 0.3045 (pH 4.81) |

Example 11B

Analysis of Crystalline Polymorph Form 2

X-Ray Powder Diffraction

The X-ray powder diffraction pattern of polymorph form 2 is shown in FIG. 5 (raw data) and 6 (background subtracted and Kα2 stripped); observed and representative peaks in the XRPD pattern are shown in the tables below (generated on background corrected and Kα2 stripped file).

| form 2 Observed ||| 
|---|---|---|
| °2θ | d space (Å) | Intensity (%) |
| 7.97 | 11.086 | 13.8 |
| 9.66 | 9.148 | 26.1 |
| 10.46 | 8.449 | 83.8 |
| 11.96 | 7.394 | 41.3 |
| 12.55 | 7.046 | 16.7 |
| 12.94 | 6.836 | 15.7 |
| 13.82 | 6.402 | 41.6 |
| 16.19 | 5.471 | 49.8 |
| 18.21 | 4.867 | 74.0 |
| 18.76 | 4.727 | 81.4 |
| 19.02 | 4.662 | 35.6 |
| 19.51 | 4.548 | 15.9 |
| 19.83 | 4.474 | 100.0 |
| 20.40 | 4.349 | 13.4 |
| 21.36 | 4.157 | 12.3 |
| 22.50 | 3.948 | 36.7 |
| 22.88 | 3.884 | 30.6 |
| 23.08 | 3.850 | 56.1 |
| 24.01 | 3.704 | 42.1 |
| 25.15 | 3.539 | 35.2 |
| 25.46 | 3.496 | 20.5 |
| 26.06 | 3.417 | 13.4 |
| 26.51 | 3.360 | 35.7 |
| 27.97 | 3.187 | 26.8 |
| 29.93 | 2.983 | 37.0 |
| 30.42 | 2.936 | 12.4 |
| 31.77 | 2.814 | 17.1 |
| 32.35 | 2.765 | 38.2 |
| 34.26 | 2.615 | 12.8 |
| 38.01 | 2.366 | 16.5 |
| 38.88 | 2.314 | 10.0 |

| form 2 Representative ||| 
|---|---|---|
| °2θ | d space (Å) | Intensity (%) |
| 19.83 | 4.474 | 100.0 |
| 10.46 | 8.449 | 83.8 |
| 18.76 | 4.727 | 81.4 |
| 18.21 | 4.867 | 74.0 |
| 23.08 | 3.850 | 56.1 |

Figure 7:
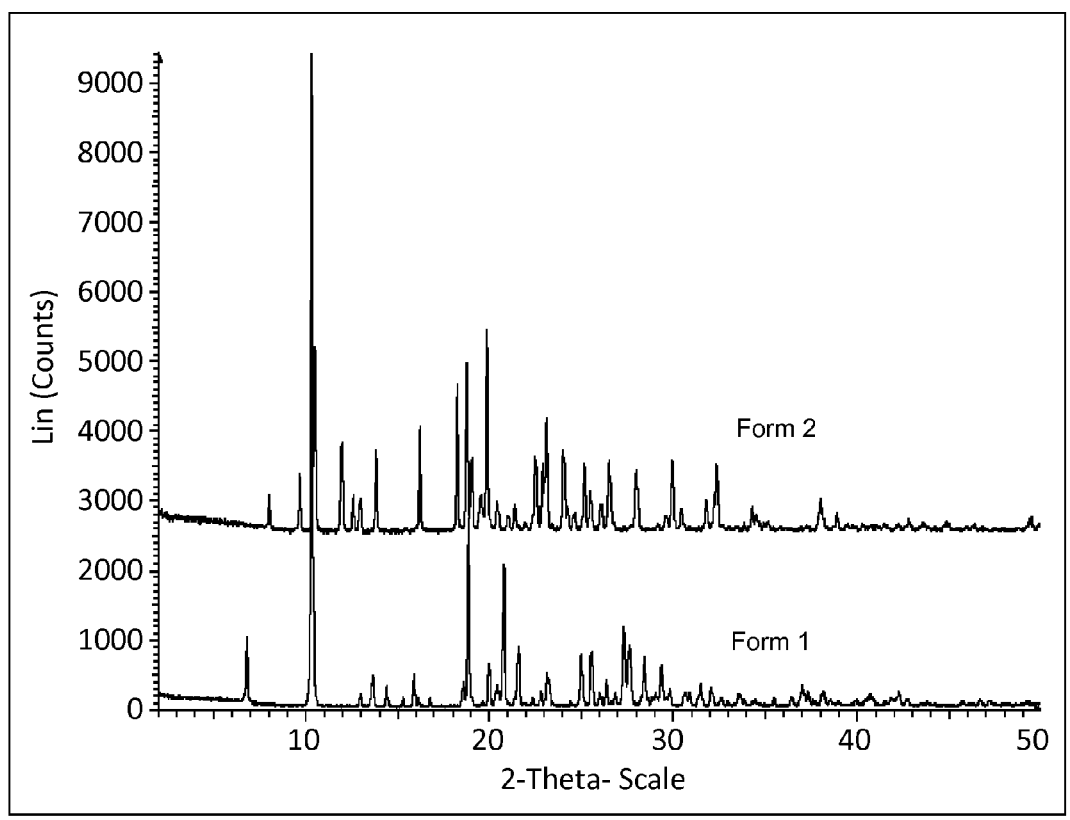
FIG. 7 represents an illustrative overlay of X-ray Powder Diffraction Patterns of Polymorph form 1 (lower) and form 2 (upper).

FIG. 7, shows an overlay of the XRPD Patterns (y-axis offset) of form 1 (lower) and form 2 (upper).

Differential Scanning calorimetry (DSC)

The differential scanning calorimetry trace for form 2 is shown in FIG. 8, a melting point at 174.7° C. was recorded.

$^1$H NMR Spectroscopy

Figure 9:
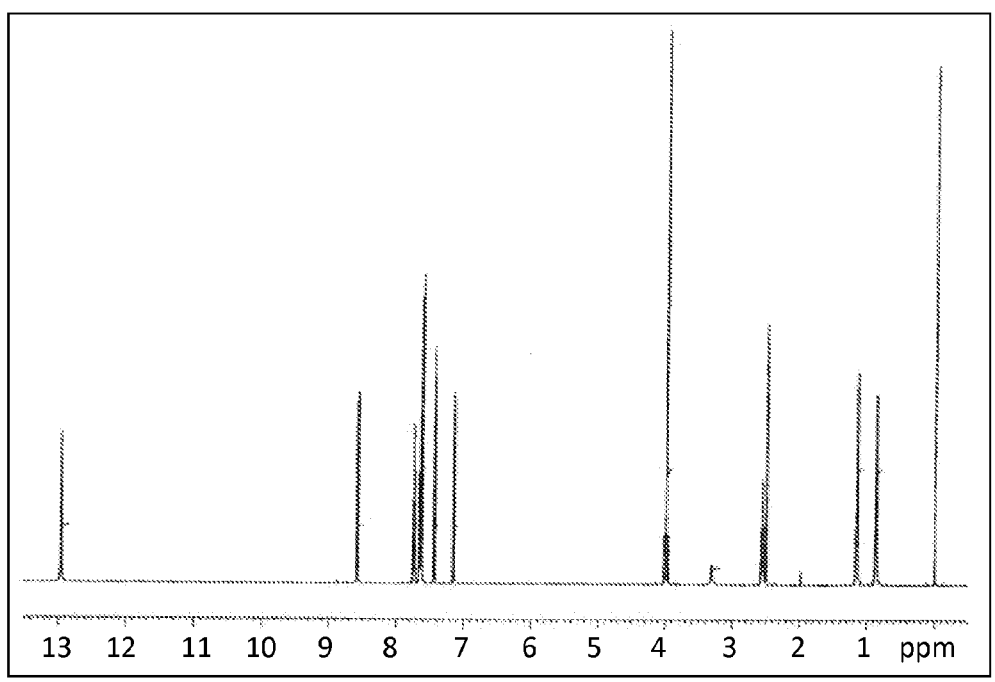
FIG. 9 represents an illustrative $^1$H NMR (DMSO-$d_6$) spectrum of Polymorph form 2.

The $^1$H NMR spectrum, taken in DMSO-$d_6$, of polymorph form 2 is shown in FIG. 9 and the major peaks listed in the table below:

| ppm | peak | integration |
|---|---|---|
| 12.96 | s | 1.00 |
| 8.58 | d | 1.01 |
| 7.74 | td | 1.01 |
| 7.65 | m | 2.02 |
| 7.44 | d | 1.01 |
| 7.16 | d | 1.00 |
| 3.99 | d | 2.02 |
| 2.49-2.58 | m | 1.00 |
| 1.16 | m | 2.03 |
| 0.88 | d | 2.01 |

HPLC

Figure 10:
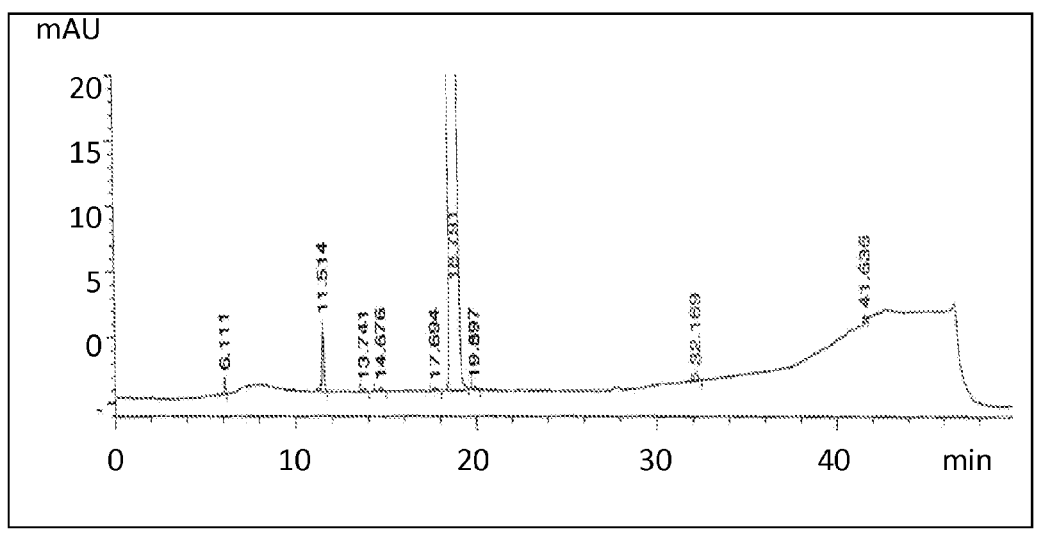
FIG. 10 represents an illustrative HPLC trace of Polymorph form 2.

The HPLC trace of polymorph form 2 is shown in FIG. 10. The peak listing for the trace is given in the table below:

| Peak # | Ret time (min) | Type | Width (min) | Area (mAU * s) | Area (%) |
|---|---|---|---|---|---|
| 1 | 6.111 | BB | 0.0621 | 5.24158 | 0.0438 |
| 2 | 11.514 | VB | 0.1157 | 39.57644 | 0.3311 |
| 3 | 13.741 | BB | 0.1436 | 2.56681 | 0.0215 |
| 4 | 143676 | BB | 0.1463 | 3.02621 | 0.0253 |
| 5 | 17.694 | BB | 0.1785 | 3.37245 | 0.0282 |
| 6 | 18.791 | BB | 0.2269 | 11,881.6 | 99.3931 |
| 7 | 19.891 | BB | 0.2502 | 5.15241 | 0.0431 |
| 8 | 32.169 | BB | 0.1785 | 8.54182 | 0.0715 |
| 9 | 41.636 | BB | 0.1163 | 5.06670 | 0.0424 |

Scanning Electron Microscopy (SEM)

SEM analysis showed form 2 primary crystals are composed of agglomerates (typical size ~25 μm) of column-like crystals (size ~10 μm).

Thermogravimetric Analysis (TGA)

Figure 11:
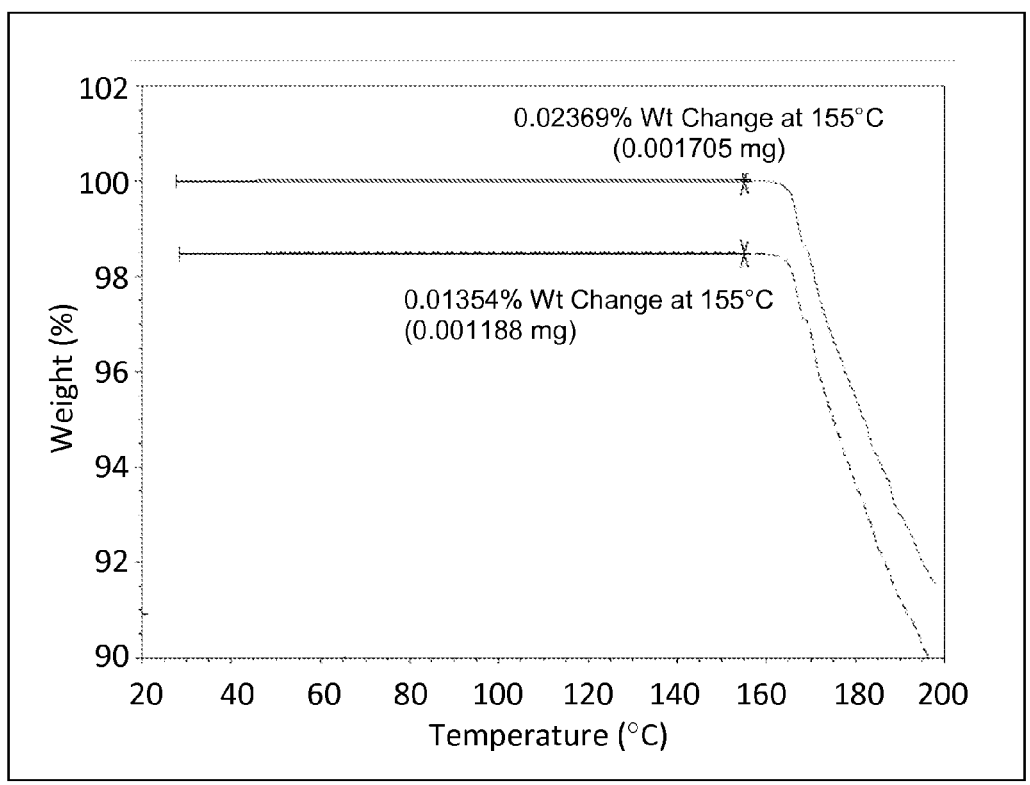
FIG. 11 represents an illustrative Thermogravimetric Analysis trace of Polymorph form 2.

Overlay of TGA scans for form 2 are shown in FIG. 11, indicating the material does not contain significant levels of volatiles.

Solubility

Form 2 (~25 mg) and acetate buffer (25 mM, pH 5, 4 mL), prepared with and without sodium chloride (ionic strength adjusted to =0.1M), were placed in a glass vial which was sealed and placed on a laboratory rotator in a 25° C. incubator. After 1, 5, and 7 days the samples were filtered and assayed by HPLC. Form 2 solubility (mg/mL), at the various time points, with and without sodium chloride, is shown in the table below:

|  | Day 1 | Day 5 | Day 7 |
|---|---|---|---|
| No NaCl | 0.1867 (pH 4.91) | 0.1957 (pH 4.73) | 0.1337 (pH 4.79) |
| NaCl (I = 0.1) | 0.2192 | 0.2441 (pH 4.83) | 0.2157 (pH 4.85) |

Form 2 of 2-(5-bromo-4-(4-cyclopropylnaphthalen-1-yl)-4H-1,2,4-triazol-3-ylthio)acetate was tested under various conditions to determine drug substance stability. No degradation of packaged Form 2 was observed for 1 month under accelerated conditions (40° C.-75% RH, or 25° C.-60% RH). Packaging was in a double low density polyethylene plastic bags inside a HDPE container.

Stability of crystalline polymorph 2-(5-bromo-4-(4-cyclopropylnaphthalen-1-yl)-4H-1,2,4-triazol-3-ylthio)acetate The crystalline polymorphs of 2-(5-bromo-4-(4-cyclopropylnaphthalen-1-yl)-4H-1,2,4-triazol-3-ylthio)acetate were found to exhibit increased stability in comparison to the amorphous solid state form of the carboxylic acid. The improved stability of the crystalline polymorphs of 2-(5-bromo-4-(4-cyclopropylnaphthalen-1-yl)-4H-1,2,4-triazol-3-ylthio)acetate provides for the preparation of pharmaceutical dosage forms displaying reduced variability in the dosage present in a given dosage form, reduction in the presence of impurities in the final pharmaceutical product, and an improved shelf life of formulated dosage forms when compared to the pharmaceutical dosage form prepared with the amorphous solid state form of the carboxylic acid.

Example 12A

X-Ray Powder Diffraction (XRPD)

XRPD patterns were collected on a Bruker D8 Advance diffractometer in the Bragg-Brentano theta/theta configuration. An incident x-ray beam was produced using a CuKα (λ=1.5418 Å) anode (tube voltage=40 kV, current=40 mA), made parallel with a 1.0 mm primary Soller slit on the source side and 1.0 mm secondary Soller slit on the detector side. CuKβ radiation was removed with a graphite monochromator slit of 1.0 mm on the detector side. A scintillation detector (NaI) was used with slit of 0.1 mm. A continuous scan of 0.02°2θ step size and 5 s per step from 2-50°2θ was used. Approximately 25 mg of material was carefully pressed onto a Si zero background wafer to ensure a flat preparation. Data were collected using Bruker Diffrac$^{plus}$ XRD Commander v2.3 software. Peak lists were generated using Bruker Diffrac$^{plus}$ EVA v9.0 software with background subtraction and Kα2 stripping. The instrument alignment check was done with a NIST alumina standard SRM1976. XRPD (Bruker D8 Advance) instrument conditions are summarized in the table below:

| Instrument Parameter | Setting |
| --- | --- |
| Configuration | Bragg-Brentano Theta/theta |
| Detector Type | Scintillation (NaI) |
| Source Type | CuKα = 1.5418 Å |
| Source Primary Soller Slit | 1.0 mm |
| Detector Secondary Soller Slit | 1.0 mm |
| Detector Slit | 0.1 mm |
| Monochromator (graphite) Slit | 1.0 mm |
| Scan Range | 2 to 50 °2θ |
| Step Size | 0.02 °2θ |
| Time per Step | 5 sec |

Example 12B

Differential Scanning Calorimetry (DSC)

Differential scanning calorimetry was performed using a TA Instruments Q2000 differential scanning calorimeter. Temperature calibration was performed using NIST traceable indium metal. Duplicate samples were prepared by sealing approximately 2-5 mg (accurately recorded) of material into a TA Tzero non-hermetic pan. A Tzero non-hermetic pan/lid was weighed and used on the reference side of the cell. Samples were heated at a rate of 10° C./min from 25° C. to 200° C., using a 50 mL/min nitrogen purge gas flow rate. The melting temperature ($T_m$) and the heat of melting ($\Delta H_m$) were measured using TA Universal Analysis software v4.4.

Example 12C

Scanning Electron Microscopy (SEM)

SEM images were collected on a JEOL SEM model JSM-6100. The sample was sprinkled onto an SEM stub containing double-sided carbon tape and was sputter coated with gold for 60 s using the Denton Desk II unit. The SEM was operated at 15 kV accelerating voltage. Images were collected using software DIPS v2.5 (Digital Imaging Processing System) with the slow scan set to 800×640 pixels and integrator at 50 us with no averaging. Images were collected at magnification ranging from 50× to 5000×.

Example 12D

Thermogravimetric Analysis (TGA)

Thermogravimetric analysis (TGA) was performed using a TA Instrument Q5000. Weight calibration was checked using a certified 50 mg weight. Duplicate samples were prepared by weighing ~5-10 mg material into a TA Pt pan. Samples were heated at a rate of 10° C./min to 200° C., using a 25 mL/min nitrogen purge gas flow rate. Weight losses were measured using TA Universal Analysis software v4.4.

Example 13A

Preparation of crystalline polymorph Form A of sodium 2-(5-bromo-4-(4-cyclopropylnaphthalen-1-yl)-4H-1,2,4-triazol-3-ylthio)acetate Deionized water (0.5 mL) was added to a stirred suspension of amorphous sodium 2-(5-bromo-4-(4-cyclopropylnaphthalen-1-yl)-4H-1,2,4-triazol-3-ylthio)acetate (1.00 g containing 1.8 wt % water) and ethyl acetate (4 mL) producing a bi-phasic mixture, which was stirred at room temperature for 18 hours. The resulting slurry was filtered under vacuum and the solids washed with ethyl acetate (2×10 mL). The filter cake was dried in vacuo at 18-20° C. with a nitrogen sweep for 4.5 hours to give 0.78 g sodium 2-(5-bromo-4-(4-cyclopropylnaphthalen-1-yl)-4H-1,2,4-triazol-3-ylthio)acetate containing 13.0 wt % water (70.3% recovery, anhydrous basis). The isolated solid was designated Form A.

Example 13B

Analysis of crystalline polymorph Form A of sodium 2-(5-bromo-4-(4-cyclopropylnaphthalen-1-yl)-4H-1,2,4-triazol-3-ylthio)acetate X-Ray Powder Diffraction One Panalytical and one Inel XRPD pattern were analyzed. The reproducibility and relative peak intensities were in good agreement between the x-ray powder diffraction patterns, indicating good particle and orientation statistics. The XRPD pattern for Form A is shown in FIG. 13; observed and representative peaks in the XRPD pattern are shown in the tables below:

| Form A Observed | | |
|---|---|---|
| °2θ | d space (Å) | Intensity (%) |
| 4.90 ± 0.10 | 18.027 ± 0.375 | 71 |
| 6.86 ± 0.10 | 12.891 ± 0.191 | 100 |
| 8.41 ± 0.10 | 10.512 ± 0.126 | 61 |
| 9.83 ± 0.10 | 8.996 ± 0.092 | 63 |
| 10.13 ± 0.10 | 8.730 ± 0.087 | 97 |
| 10.60 ± 0.10 | 8.346 ± 0.079 | 16 |
| 11.92 ± 0.10 | 7.424 ± 0.063 | 45 |
| 12.32 ± 0.10 | 7.183 ± 0.059 | 45 |
| 12.57 ± 0.10 | 7.041 ± 0.056 | 45 |
| 13.07 ± 0.10 | 6.772 ± 0.052 | 42 |
| 14.01 ± 0.10 | 6.322 ± 0.045 | 21 |
| 14.48 ± 0.10 | 6.118 ± 0.042 | 35 |
| 14.80 ± 0.10 | 5.988 ± 0.041 | 23 |
| 15.15 ± 0.10 | 5.850 ± 0.039 | 52 |
| 16.28 ± 0.10 | 5.444 ± 0.033 | 18 |
| 16.70 ± 0.10 | 5.309 ± 0.032 | 20 |
| 16.90 ± 0.10 | 5.246 ± 0.031 | 22 |
| 17.92 ± 0.10 | 4.950 ± 0.028 | 70 |
| 18.64 ± 0.10 | 4.761 ± 0.025 | 36 |
| 20.88 ± 0.10 | 4.255 ± 0.020 | 42 |
| 21.35 ± 0.10 | 4.163 ± 0.019 | 25 |
| 21.68 ± 0.10 | 4.099 ± 0.019 | 18 |
| 22.42 ± 0.10 | 3.966 ± 0.018 | 38 |
| 23.10 ± 0.10 | 3.850 ± 0.017 | 55 |
| 23.54 ± 0.10 | 3.780 ± 0.016 | 20 |
| 23.95 ± 0.10 | 3.715 ± 0.015 | 37 |
| 24.67 ± 0.10 | 3.609 ± 0.014 | 44 |
| 25.29 ± 0.10 | 3.522 ± 0.014 | 68 |
| 26.38 ± 0.10 | 3.379 ± 0.013 | 33 |
| 26.96 ± 0.10 | 3.307 ± 0.012 | 33 |
| 27.63 ± 0.10 | 3.229 ± 0.012 | 22 |
| 28.36 ± 0.10 | 3.147 ± 0.011 | 29 |
| 29.07 ± 0.10 | 3.072 ± 0.010 | 35 |

| Form A Representative | | |
|---|---|---|
| °2θ | d space (Å) | Intensity (%) |
| 4.90 ± 0.10 | 18.027 ± 0.375 | 71 |
| 6.86 ± 0.10 | 12.891 ± 0.191 | 100 |
| 8.41 ± 0.10 | 10.512 ± 0.126 | 61 |
| 9.83 ± 0.10 | 8.996 ± 0.092 | 63 |
| 10.13 ± 0.10 | 8.730 ± 0.087 | 97 |
| 17.92 ± 0.10 | 4.950 ± 0.028 | 70 |
| 23.10 ± 0.10 | 3.850 ± 0.017 | 55 |
| 25.29 ± 0.10 | 3.522 ± 0.014 | 68 |

The differential scanning calorimetry trace for Form A is shown in FIG. 14.

Figure 15:
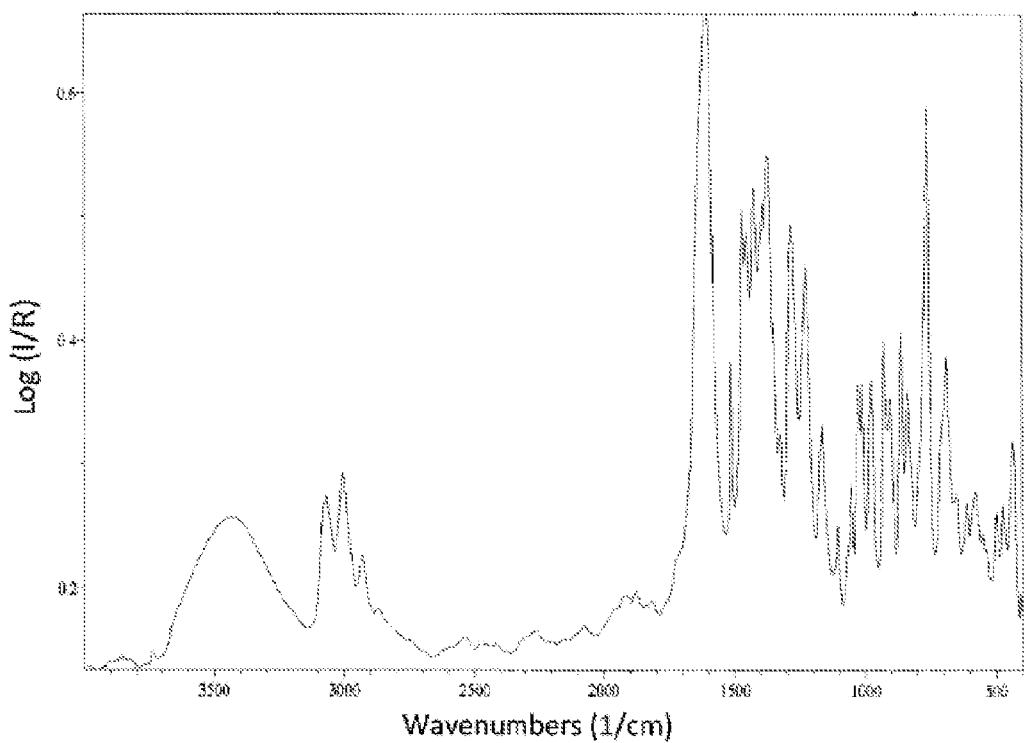
FIG. 15 represents an illustrative infrared spectrum of Polymorph Form A.

The infrared absorption spectrum of Form A is shown in FIG. 15.

Figure 16:
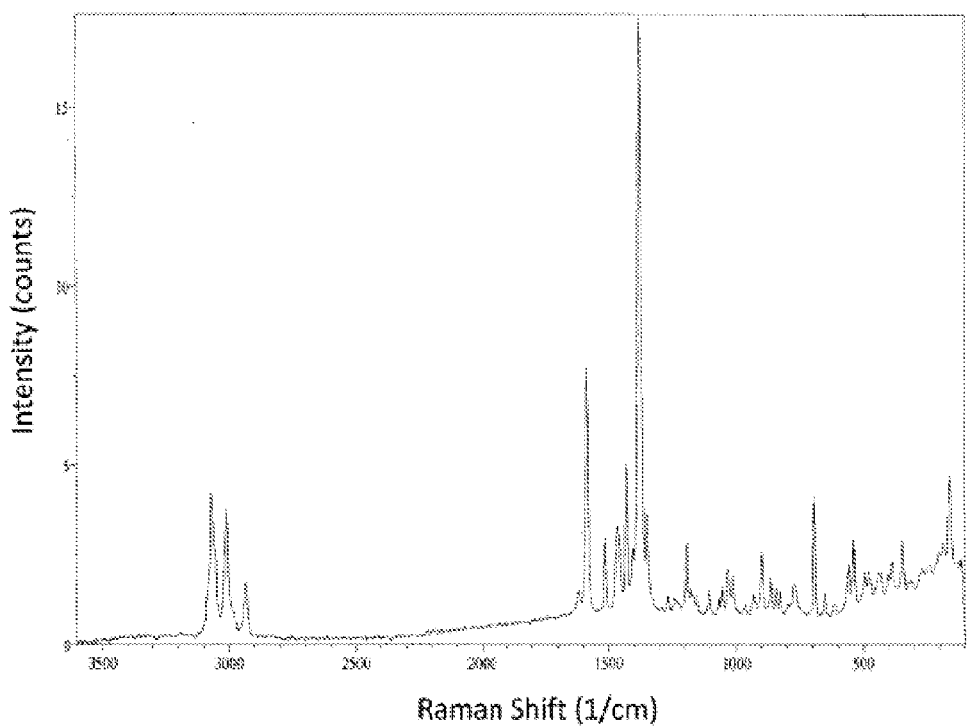
FIG. 16 represents an illustrative Raman spectrum of Polymorph Form A.

The Raman spectrum of Form A is shown in FIG. 16.

Form A of sodium 2-(5-bromo-4-(4-cyclopropylnaphthalen-1-yl)-4H-1,2,4-triazol-3-ylthio)acetate was tested under various conditions to determine thermodynamic stability. No degradation of packaged Form A was observed for 6 months under accelerated conditions (40° C.-75% RH). Moreover, no degradation of packaged Form A was observed for 12 months under long term conditions (25° C.-60% RH). Packaging was in a double low density polyethylene plastic bag inside a heat sealed anhydrous foil bag in an HDPE container. The stability results of Form A demonstrated an improvement over the solid state amorphous free acid.

Example 14A

Preparation of crystalline polymorph Form B of sodium 2-(5-bromo-4-(4-cyclopropylnaphthalen-1-yl)-4H-1,2,4-triazol-3-ylthio)acetate Preparation i A mixture of sodium 2-(5-bromo-4-(4-cyclopropylnaphthalen-1-yl)-4H-1,2,4-triazol-3-ylthio)acetate (3.02 g, Form A) and water-saturated ethyl acetate (6 mL) was stirred at 45-50° C. for 16 hours producing a bi-phasic mixture, which was gradually cooled to room temperature over 2 hours and stirred for an additional 21 hours to give a uniform suspension. The suspension was vacuum filtered, washed with ethyl acetate and the filter cake dried in vacuo at 18-20° C. with a nitrogen sweep for 2 hours to give 2.77 g sodium 2-(5-bromo-4-(4-cyclopropylnaphthalen-1-yl)-4H-1,2,4-triazol-3-ylthio)acetate containing 12.9 wt % water (91.7% recovery, anhydrous basis).

Preparation ii

Sodium 2-(5-bromo-4-(4-cyclopropylnaphthalen-1-yl)-4H-1,2,4-triazol-3-ylthio)acetate (Form A) was stirred at ~50° C. in water-saturated ethyl acetate (0.5 mL) overnight, converting the solids to oil. The oil was scratched with a dental pick and left to stir at ambient temperature. After ~3 days, optical microscopy indicated crystalline solids. The liquid was removed by decantation and the solids isolated.

The isolated solids were designated Form B.

Example 14B

Analysis of crystalline polymorph Form B of Sodium 2-(5-bromo-4-(4-cyclopropylnaphthalen-1-yl)-4H-1,2,4-triazol-3-ylthio)acetate X-Ray Powder Diffraction One Panalytical and one Inel XRPD pattern were analyzed. The reproducibility and relative peak intensities were in good agreement between the x-ray powder diffraction patterns, indicating good particle and orientation statistics. The XRPD pattern for Form B is shown in FIG. 17; observed and representative peaks in the XRPD pattern are shown in the tables below:

| Form B Observed | | |
|---|---|---|
| °2θ | d space (Å) | Intensity (%) |
| 4.22 ± 0.10 | 20.939 ± 0.508 | 100 |
| 8.51 ± 0.10 | 10.392 ± 0.123 | 79 |
| 12.80 ± 0.10 | 6.917 ± 0.054 | 40 |
| 13.97 ± 0.10 | 6.337 ± 0.045 | 20 |
| 14.46 ± 0.10 | 6.126 ± 0.042 | 21 |
| 16.19 ± 0.10 | 5.475 ± 0.034 | 23 |
| 16.95 ± 0.10 | 5.231 ± 0.031 | 45 |
| 18.40 ± 0.10 | 4.821 ± 0.026 | 22 |
| 19.13 ± 0.10 | 4.639 ± 0.024 | 26 |
| 19.48 ± 0.10 | 4.558 ± 0.023 | 24 |
| 20.03 ± 0.10 | 4.433 ± 0.022 | 25 |
| 21.28 ± 0.10 | 4.176 ± 0.019 | 23 |
| 22.56 ± 0.10 | 3.942 ± 0.017 | 32 |
| 22.90 ± 0.10 | 3.883 ± 0.017 | 27 |
| 23.53 ± 0.10 | 3.781 ± 0.016 | 24 |
| 25.64 ± 0.10 | 3.474 ± 0.013 | 28 |
| 27.27 ± 0.10 | 3.271 ± 0.012 | 18 |

-continued

Form B Observed

| °2θ | d space (Å) | Intensity (%) |
|---|---|---|
| 28.17 ± 0.10 | 3.168 ± 0.011 | 15 |
| 28.72 ± 0.10 | 3.108 ± 0.011 | 19 |

Form B Representative

| °2θ | d space (Å) | Intensity (%) |
|---|---|---|
| 4.22 ± 0.10 | 20.939 ± 0.508 | 100 |
| 8.51 ± 0.10 | 10.392 ± 0.123 | 79 |
| 12.80 ± 0.10 | 6.917 ± 0.054 | 40 |
| 16.95 ± 0.10 | 5.231 ± 0.031 | 45 |

The differential scanning calorimetry trace for Form B is shown in FIG. 18.

Example 15A

Preparation of crystalline polymorph Form B' of sodium 2-(5-bromo-4-(4-cyclopropylnaphthalen-1-yl)-4H-1,2,4-triazol-3-ylthio)acetate Sodium 2-(5-bromo-4-(4-cyclopropylnaphthalen-1-yl)-4H-1,2,4-triazol-3-ylthio)acetate (Form B containing 12.9 wt % water) was dried under vacuum at ambient temperature for 1-3 days resulting in an off-white solid, designated as form B'.

Example 15B

Analysis of crystalline polymorph Form B' of sodium 2-(5-bromo-4-(4-cyclopropylnaphthalen-1-yl)-4H-1,2,4-triazol-3-ylthio)acetate The x-ray powder diffraction pattern for Form B', shown in FIG. 19, resembles that of Form B, however with non-uniform peak shifts between the patterns, suggesting a different solvation state of the same polymorph. The differential scanning calorimetry trace of Form B' is shown in FIG. 20.

Stability of crystalline polymorph sodium 2-(5-bromo-4-(4-cyclopropylnaphthalen-1-yl)-4H-1,2,4-triazol-3-ylthio)acetate The crystalline polymorphs of sodium 2-(5-bromo-4-(4-cyclopropylnaphthalen-1-yl)-4H-1,2,4-triazol-3-ylthio)acetate were found to exhibit increased stability in comparison to the amorphous solid state form of the carboxylic acid. The improved stability of the crystalline polymorphs of sodium 2-(5-bromo-4-(4-cyclopropylnaphthalen-1-yl)-4H-1,2,4-triazol-3-ylthio)acetate provides for the preparation of pharmaceutical dosage forms displaying reduced variability in the dosage present in a given dosage form, reduction in the presence of impurities in the final pharmaceutical product, and an improved shelf life of formulated dosage forms when compared to the pharmaceutical dosage form prepared with the amorphous solid state form of the carboxylic acid.

Example 16

Impurities Identified in Samples of Compound 1 Prepared Using the Processes Described Herein The following compounds (Compounds I-X) were identified as impurities in samples of Compound 1, which was prepared using the processes described herein, including Examples 1 and 2:

2-(4-(4-cyclopropylnaphthalen-1-yl)-4H-1,2,4-triazol-3-ylthio)acetic acid;
2-(4-(4-cyclopropylnaphthalen-1-yl)-5-hydroxy-4H-1,2,4-triazol-3-ylthio)acetic acid;
2-(5-amino-4-(4-cyclopropylnaphthalen-1-yl)-4H-1,2,4-triazol-3-ylthio)acetic acid;
2-(5-bromo-4-(1-cyclopropylnaphthalen-2-yl)-4H-1,2,4-triazol-3-ylthio)acetic acid;
2-(5-bromo-4-(4-methylnaphthalen-1-yl)-4H-1,2,4-triazol-3-ylthio)acetic acid;
2-(5-bromo-4-(4-propylnaphthalen-1-yl)-4H-1,2,4-triazol-3-ylthio)acetic acid;
2-(5-bromo-4-(5-cyclopropylnaphthalen-1-yl)-4H-1,2,4-triazol-3-ylthio)acetic acid;
2-(5-bromo-4-(naphthalen-1-yl)-4H-1,2,4-triazol-3-ylthio)acetic acid;
2-(5-chloro-4-(4-cyclopropylnaphthalen-1-yl)-4H-1,2,4-triazol-3-ylthio)acetic acid; and
4-(5-(carboxymethylthio)-4-(4-cyclopropylnaphthalen-1-yl)-4H-1,2,4-triazol-3-ylamino)-4-oxobutanoic acid.

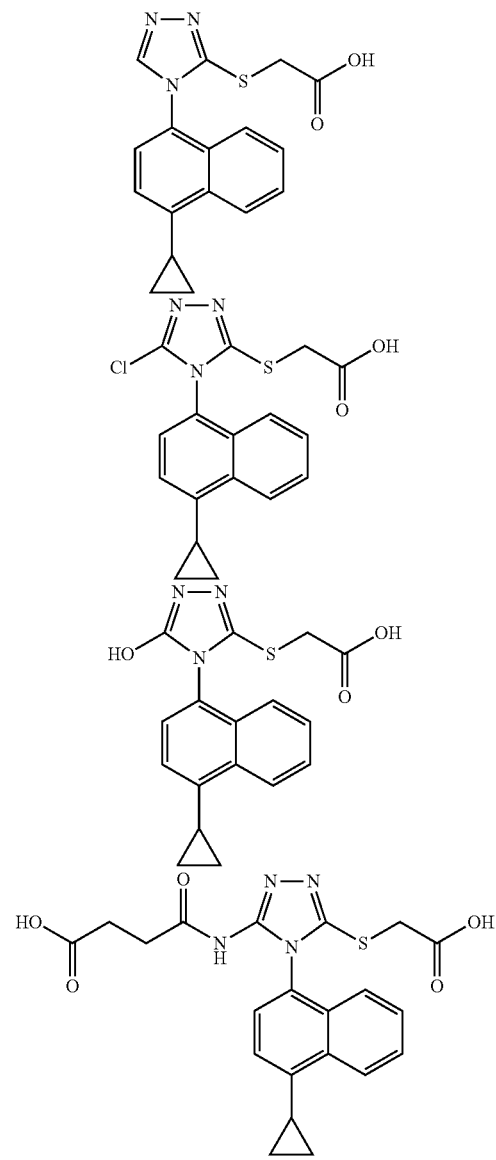

101
-continued

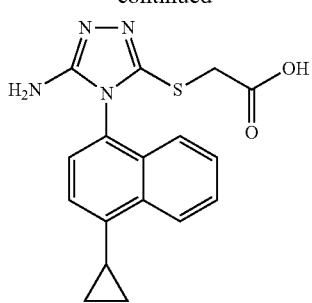

102

What is claimed is:
1. A process for preparing a compound of formula (III):

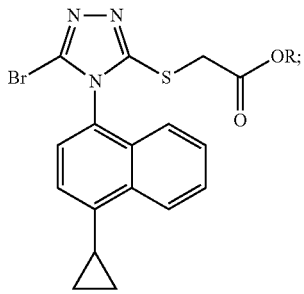
Formula (III)

comprising contacting a compound of Formula (II):

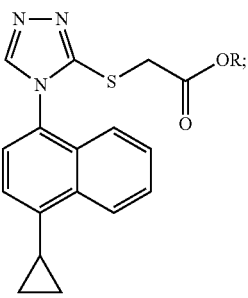
Formula (II)

wherein R is —$C_1$-$C_{20}$ alkyl, —$C_1$-$C_{20}$ alkenyl, —$C_3$-$C_{10}$ cycloalkyl, or —$C_3$-$C_{10}$ cycloalkenyl;
with N-bromosuccinimide (NBS) and a solvent.

2. The process of claim 1, wherein R is methyl, ethyl, propyl, isopropyl, butyl, isobutyl, tert-butyl, isoamyl, pentyl, hexyl, heptyl, octyl, nonyl, terpenyl, bornyl, allyl, linalyl or geranyl.

3. The process of claim 1, wherein R is methyl or ethyl.

4. The process of claim 1, wherein the compound of Formula (II), the NBS and the solvent are stirred:
for at least 12 hours; and
at a temperature of between about room temperature and about 32° C.

5. The process of claim 1, further comprising contacting the compound of Formula (III) with a sodium hydroxide solution to provide Compound 4:

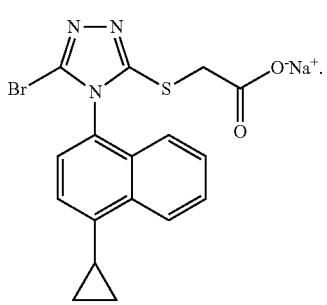
(Compound 4)

6. The process of claim 5, comprising crystallizing Compound 4 from the aqueous sodium hydroxide solution.

7. The process of claim 5, further comprising contacting Compound 4 with an acid to provide Compound 1:

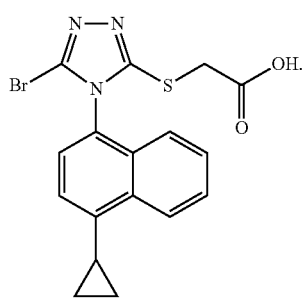
(Compound 1)
8. The process of claim 7, wherein the acid is hydrobromic acid.
9. The process of claim 5, further comprising
   (a) dissolving Compound 4 in water and adding ethyl acetate to the mixture; and
   (b) contacting the biphasic mixture of step (a) with an acid and separating the organic phase to provide Compound 1.
* * * * *